US008013014B2

(12) United States Patent
Powers et al.

(10) Patent No.: US 8,013,014 B2
(45) Date of Patent: Sep. 6, 2011

(54) AZA-PEPTIDE EPOXIDES

(75) Inventors: James C. Powers, Atlanta, GA (US);
Jonathan D. Glass, Atlanta, GA (US)

(73) Assignee: Georgia Tech Research Corporation, Atlanta, GA (US)

( * ) Notice: Subject to any disclaimer, the term of this patent is extended or adjusted under 35 U.S.C. 154(b) by 1493 days.

(21) Appl. No.: 11/338,147

(22) Filed: Jan. 24, 2006

(65) Prior Publication Data

US 2006/0172952 A1 Aug. 3, 2006

Related U.S. Application Data

(63) Continuation-in-part of application No. 10/603,054, filed on Jun. 24, 2003, now Pat. No. 7,056,947, and a continuation-in-part of application No. 10/671,360, filed on Sep. 25, 2003.

(60) Provisional application No. 60/394,221, filed on Jul. 5, 2002, provisional application No. 60/394,023, filed on Jul. 5, 2002, provisional application No. 60/394,024, filed on Jul. 5, 2002, provisional application No. 60/413,506, filed on Sep. 25, 2002.

(51) Int. Cl.
*A61K 31/335* (2006.01)

(52) U.S. Cl. ...................................... 514/475

(58) Field of Classification Search .............. 514/475
See application file for complete search history.

(56) References Cited

U.S. PATENT DOCUMENTS

| | | | |
|---|---|---|---|
| 5,770,732 A | 6/1998 | Hirschmann et al. |
| 5,998,470 A | 12/1999 | Halbert et al. |
| 6,331,542 B1 | 12/2001 | Carr et al. |
| 6,376,468 B1 | 4/2002 | Overleeft et al. |
| 6,387,908 B1 | 5/2002 | Nomura et al. |
| 6,462,078 B1 | 10/2002 | Ono et al. |
| 6,479,676 B1 | 11/2002 | Wolf |
| 6,586,466 B2 | 7/2003 | Yamashita |
| 6,689,765 B2 | 2/2004 | Baroudy et al. |
| 6,831,099 B1 | 12/2004 | Crews et al. |

OTHER PUBLICATIONS

Byrn et al., Solid-State Chemistry of Drugs, Second Edition, 1999, pp. 233-247.*
James et al., Journal of Medicinal Chemistry, 2004 (47 (6), 1553-1574.*
Canu et al., The Journal of Neuroscience, Jan. 15, 2000, 20(2), 589-599.*
Friedlander et al., Cell Death and Differentation (1998) 5, 823-831.*
Kato et al., Neurotoxicology, Aug. 2000, 21(4): 513-20. Abstract only.*
Li et al., Science, Apr. 14, 2000, 288, 5464, 335-339.*
Vukosavic et al., J. Neurosci., Dec. 15, 2000, 20(24): 9119-9125.*
Yamakawa et al., Neurological Research, Jul. 2001; 23(5); 522-30.*
Gylys et al., Neurochemical Research, vol. 27, No. 6, Jun. 2002, pp. 465-472.*
Banik et al., Ann N Y Acad Sci., Oct. 15, 1997; 825: 120-7.*
Nixon, Ann N Y Acad Sci., 2000; 924; 117-31.*
Kidwai, M., Kumar, K., Giel, T., Srivastava, K. C. "Oxiranes with quinoline substitution: steroselective synthesis and antiviral activity." CA125:33462, 1996.

* cited by examiner

*Primary Examiner* — Rebecca Anderson
(74) *Attorney, Agent, or Firm* — Thomas, Kayden, Horstemeyer & Risley, LLP

(57) ABSTRACT

Methods for treatment and/or prevention of nerve degeneration in mammals using aza-peptide epoxide caspase inhibitors are provided. Aspects of the present disclosure include aza-peptide epoxide compositions to treat or prevent diseases, for example stroke, Alzheimer's disease, Parkinson's disease, multiple sclerosis, neuropathies, Huntington's disease, dentatorubropallidoluysian atrophy, spinocerebellar atrophies, spinal bulbar muscular atrophy, diabetes, amyotrophic lateral sclerosis and other motor neuron diseases. The disclosed methods can be used in combination with calpain inhibitors to treat disease or pathological conditions related to the activity of caspases and calpain associated with a specific disease or condition. Such treatable conditions include stroke, Alzheimer's disease, Parkinson's disease, multiple sclerosis, neuropathies, Huntington's disease, dentatorubropallidoluysian atrophy, spinocerebellar atrophies, spinal bulbar muscular atrophy, nerve degeneration associated with diabetes, amyotrophic lateral sclerosis and other motor neuron diseases, nerve degeneration secondary to primary demyelinating disorders, among others.

38 Claims, 1 Drawing Sheet

SEQUENCE LISTING

```
<160> NUMBER OF SEQ ID NOS: 4

<210> SEQ ID NO 1
<211> LENGTH: 5
<212> TYPE: PRT
<213> ORGANISM: Artificial
<220> FEATURE:
<223> OTHER INFORMATION: consensus active site motif for caspases
<220> FEATURE:
<221> NAME/KEY: MISC_FEATURE
<222> LOCATION: (4)..(4)
<223> OTHER INFORMATION: X = R, Q, OR G

<400> SEQUENCE: 1

Gln Ala Cys Xaa Gly
1               5

<210> SEQ ID NO 2
<211> LENGTH: 4
<212> TYPE: PRT
```

```
<213> ORGANISM: artificial
<220> FEATURE:
<223> OTHER INFORMATION: caspase recognition sequence

<400> SEQUENCE: 2

Trp Glu His Asp
1

<210> SEQ ID NO 3
<211> LENGTH: 4
<212> TYPE: PRT
<213> ORGANISM: artificial
<220> FEATURE:
<223> OTHER INFORMATION: caspase group II recognition sequence
<220> FEATURE:
<221> NAME/KEY: misc_feature
<222> LOCATION: (3)..(3)
<223> OTHER INFORMATION: Xaa can be any naturally occurring amino acid

<400> SEQUENCE: 3

Asp Glu Xaa Asp
1

<210> SEQ ID NO 4
<211> LENGTH: 4
<212> TYPE: PRT
<213> ORGANISM: artificial
<220> FEATURE:
<223> OTHER INFORMATION: caspase group III recognition sequence
<220> FEATURE:
<221> NAME/KEY: MISC_FEATURE
<222> LOCATION: (1)..(1)
<223> OTHER INFORMATION: X = V OR L
<220> FEATURE:
<221> NAME/KEY: misc_feature
<222> LOCATION: (3)..(3)
<223> OTHER INFORMATION: Xaa can be any naturally occurring amino acid

<400> SEQUENCE: 4

Xaa Glu Xaa Asp
1
```

AZA-PEPTIDE EPOXIDES

CROSS-REFERENCED TO RELATED APPLICATIONS

This application is a continuation-in-part of U.S. Utility patent application Ser. No. 10/603,054 entitled "Aza-Peptide Epoxides," filed on Jun. 24, 2003 now U.S. Pat. No. 7,056,947 (which claims the benefit of U.S. Provisional Patent Application No. 60/394,221 filed on Jul. 5, 2002, U.S. Provisional Patent Application No. 60/394,023, filed on Jul. 5, 2002, and U.S. Provisional Patent Application No. 60/394,024 filed on Jul. 5, 2002) and of U.S. Utility patent application Ser. No. 10/671,360 entitled "Ketoamide Inhibitors in Chronic Nerve Disease," filed on Sep. 25, 2003 (which claims the benefit of U.S. Provisional Patent Application No. 60/413,506 filed on Sep. 25, 2002), all of which are incorporated herein by reference in their entirety.

STATEMENT REGARDING FEDERALLY SPONSORED RESEARCH OR DEVELOPMENT

Aspects of the work described herein were supported by grant No. GM061964 from the National Institutes of Health. Therefore, the U.S. government has certain rights in the disclosure.

BACKGROUND

1. Field of the Disclosure

This disclosure relates generally to protease inhibitors and applications thereof, more specifically to peptide inhibitors of cysteine proteases, even more specifically to aza-peptide epoxides, methods of their use, and methods of their production. Other aspects of the present disclosure relate to the use of the above compositions for the treatment of neurodegeneration and conditions associated with neurodegeneration.

2. Related Art

Protease inhibitors are important therapeutics in the treatment of a variety of disease conditions including viral infections such as HIV infection. Proteases are enzymes that cleave proteins or peptides and are classified into several groups. For example, cysteine proteases form a group of enzymes involved in numerous disease states, and inhibitors of these enzymes can be used therapeutically for the treatment of diseases involving cysteine proteases.

To date, a structurally diverse variety of cysteine protease inhibitors have been identified. Palmer, (1995) J. Med. Chem., 38, 3193, discloses certain vinyl sulfones which act as cysteine protease inhibitors for cathepsins B, L, S, O2 and cruzain. Other classes of compounds, such as aldehydes, nitriles, α-ketocarbonyl compounds, halomethyl ketones, diazomethyl ketones, (acyloxy)methyl ketones, ketomethylsulfonium salts and epoxy succinyl compounds have also been reported to inhibit cysteine proteases. See Palmer, id, and references cited therein. Many irreversible cysteine protease inhibitors have been described in the review by Powers, Asgian, Ekici, and James (2002) Chemical Reviews, 102, 4639. See Powers, id, and references cited therein. However, most of these known inhibitors are not considered suitable for use as therapeutic agents in animals, especially humans, because they suffer from various shortcomings. These shortcomings include lack of selectivity, cytotoxicity, poor solubility, and overly rapid plasma clearance.

In addition, epoxides also have been shown to inhibit cysteine proteases. The first epoxysuccinyl peptide discovered was E-64, a natural inhibitor, which was initially isolated from *Aspergillus japonicus* by Hanada et al. in 1978. The chemical structure was determined by optical rotation, NMR, IR, MS, elemental analysis, and amino acid analysis to be N-(N-(L-3-trans-carboxyoxiran-2-carbonyl)-L-leucyl)agmatine. Hanada and his coworkers showed that E-64 would inactivate the plant cysteine proteases papain, ficin, and bromelain.

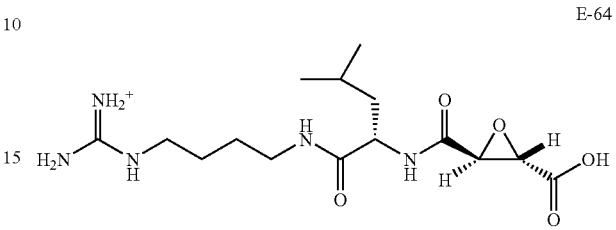

E-64

Once the E-64 structure was elucidated, the research groups of Katunuma, Barrett, and others discovered E-64's inhibitory potency toward a large number of other cysteine proteases. E-64 inhibits papain, ficin, bromelain, cathepsin B, H, F, K, L, O, S, V, X, calpain, calpain II, cruzain, and other cysteine proteases. Cathepsin J and streptococcal cysteine protease are slowly inhibited by E-64.

Unlike many other microbial inhibitors, E-64 is a potent and specific irreversible inhibitor of cysteine proteases, and is used as a diagnostic reagent for identification of cysteine proteases. The compound E-64 does not inhibit serine proteases, aspartic proteases, or metalloproteases. However, not all cysteine proteases are inhibited by E-64. Examples of non-inhibited cysteine proteases are legumain and caspases. Caspases and legumain are members of the CD clan of cysteine proteases, while papain, cathepsins, and calpains are members of clan CA. The following table lists those enzymes which are inactivated by E-64 and those which are not inactivated.

| Enzymes Inactivated or Not Inactivated by E-64. | | |
|---|---|---|
| enzymes inactivated | rate ($M^{-1} s^{-1}$) | enzymes not inactivated |
| ficin | 0.084 ($ID_{50}$) | trypsin |
| fruit bromelain | 0.110 ($ID_{50}$) | α-chymotrypsin |
| stem bromelain | 0.025 ($ID_{50}$) | kallikrein |
| papain | 0.104 ($ID_{50}$) | pepsin |
| cathepsin B | 89,400 | plasmin |
| cathepsin H | 4,000 | elastase |
| cathepsin L | 96,250 | Mold acid protease |
| cathepsin K | 1.8 nM ($K_i$) | LDH |
| cathepsin S | 99,000 | thermolysin |
| cathepsin X | 775 | collagenase |
| cathepsin O | >100 μM ($IC_{50}$) | clostripain |
| cathepsin F | | caspase 1 (ICE) |
| cathepsin V | >0.1 μM ($IC_{50}$) | legumain |
| cathepsin J | | |
| DPPI | 100 | |
| streptococcal proteinase | 624 | |
| papaya proteinase IV | 58,000 | |
| calpain II | 7,500 | |
| bleomycin hydrolase | >160 μM ($IC_{50}$) | |
| cruzain | 70,600 | |
| vignain | 32,500 | |

Therefore, because of the aforementioned deficiencies in the art, there is a need for new compounds and methods for inhibiting proteases, in particular cysteine proteases.

There is also a need for compositions and methods for treating nerve degeneration in patients, particularly since peripheral neuropathy is a major dose-limiting complication of commonly used anti-cancer agents, including vincristine, cisplatin, and paclitaxel (Taxol®). Paclitaxel, a microtubule toxin derived from the western yew tree, is particularly effective against solid tumors, but causes a predominantly sensory neuropathy that may be severe enough to necessitate cessation of treatment. The neuropathy is characterized by degeneration of sensory axons, manifesting clinically as numbness, pain, and loss of balance [Lipton, R. B., S. C. Apfel, J. P. Dutcher, R. Rosenberg, J. Kaplan, A. Berger, A. I. Einzig, P. Wiernik and H. H. Schaumburg (1989). "Taxol produces a predominantly sensory neuropathy." *Neurology* 39 (3): 368-73]. Paclitaxel causes a similar sensory neuropathy in rodents that provides a useful experimental model for the treatment of peripheral neuropathies.

Because neuronal pathologies, in particular neuropathy, can have a dramatic impact on quality of life of patients, there is also a need for compositions and methods for treating these disorders, in particular, compositions and methods for treating pathologies with little or reduced side effects such as neuropathy. There is also a need for methods and compositions for treating axonal degeneration.

SUMMARY

The present disclosure is directed to providing compositions and methods for meeting the aforementioned needs. Aspects of the present disclosure provide compositions for inhibiting proteases, methods for synthesizing the compositions, and methods of using the disclosed protease inhibitors. The compositions described herein can inhibit proteases, for example cysteine proteases, either in vivo or in vitro, by contacting a cysteine protease with an aza-peptide epoxide. The disclosed compounds, pharmaceutically acceptable salts, pharmaceutically acceptable derivatives, prodrugs, or combinations thereof can be used to treat disease or pathological conditions related to the activity of proteases associated with a specific disease or condition. Such treatable conditions include viral infections, stroke, neurodegenerative disease, and inflammatory disease, among others. Methods disclosed herein for treating diseases include administering an effective amount of an aza-peptide epoxide to a host in need thereof to inhibit or reduce protease activity in the host, particularly cysteine protease activity, more particularly activity of caspases, calpains, cathepins, papain, gingipain, clostripain, separin, or legumain. One or more aza-peptide epoxides of the present disclosure can also be used alone or in combination with each other, other protease inhibitors, or another therapeutic agent including anti-viral compounds such as anti-viral nucleosides including nucleoside analogs.

One aspect of the present disclosure provides aza-peptide epoxide compositions, for example a compound or pharmaceutically acceptable salt or pharmaceutically acceptable derivative thereof according to Formula I below. In some aspects of the present disclosure, aza-peptide epoxide inhibitors are specific for cysteine proteases and do not inhibit serine proteases or aspartyl proteases. In another aspect of the present disclosure, these aza-peptide epoxide compounds potently and specifically inhibit clan CD of cysteine proteases and are also inhibitors of clan CA. Exemplary differences between aza-peptide epoxides disclosed herein and other cysteine proteases inhibitors include different mechanisms of inhibition of the cysteine residue and the binding modes.

Some aza-peptide epoxides of the present disclosure can be constructed to selectively inhibit individual cysteine proteases or groups of cysteine proteases. These aza-peptide epoxides can, for example, contain acidic aza-amino acid residues in the P1 site. Such aza-peptide epoxides are potent inhibitors of caspases. Aza-peptide epoxide caspase inhibitors are useful for the treatment of stroke and inflammatory diseases, and as inhibitors of apoptosis. Thus, another aspect provides a method of treating stroke, inflammatory disease, or inhibiting apoptosis including administering an effective amount of a aza-peptide epoxide to a patient in need thereof. Such patients can include any mammal, for example a mammal exhibiting symptoms characteristic protease related pathology or disease condition such as stroke, inflammatory disease, or pathology related to apoptosis.

Another aspect of the present disclosure provides an aza-peptide epoxide composition containing an aza-asparagine residue at the P1 position. Aza-peptide epoxides having an aza-asparagine residue at the P1 position inhibit legumain and can, therefore, modulate the immune system through such inhibition. Cleavage of antigens by proteases such as legumain and related proteases is a step in antigen presentation including the display of MHC class II peptides. Thus, another aspect of the present disclosure provides a method of modulating the immune system of a patient by administering to a host an effective amount of an aza-peptide epoxide composition. The aza-peptide epoxide can modulate the immune system by inhibiting the cleavage of antigens in the patient and thereby reducing the display of antigen peptides on cell surfaces.

Yet another aspect of the present disclosure provides a method of treating autoimmune disease by administering an effective amount of an aza-peptide epoxide to a host in need thereof. The host can be any mammal, including primates, which demonstrate symptoms associated with any number of autoimmune diseases including but not limited to lupus, for example lupus erythematosus, and cancers.

Another aspect of the present disclosure provides aza-peptide epoxides containing basic residues at the P1 position. Such aza-peptide epoxides inhibit proteases such as gingipain, separin, and clostripain. Aza-peptide epoxide inhibitors of gingipain can be used for treatment of periodontal diseases. Aza-peptide epoxide inhibitors of separin are useful for stopping, modulating, or interfering with cell division.

Yet another aspect of the present disclosure provides aza-peptide epoxide protease inhibitors with hydrophobic amino acid residues in the P2 site. These aza-peptide epoxide protease inhibitors inhibit proteases such as cathepsins, including cathepsin B, and papain. Aza-peptide epoxide inhibitors of cathepsin B are useful for treating hyperproliferative conditions including cancer.

Another aspect provides aza-peptide epoxides having small hydrophobic alkyl amino acid residues at P2 are good inhibitors of calpain I and II. These inhibitors are useful as neuroprotectants and can be used as therapeutics for the treatment or prevention of neurodegeneration and stroke and pathologies of the peripheral nervous system such as neuropathy, axonal degeneration, or calcium-induced cell injury. Exemplary neuodegenerative disorders that can be treated with the disclosed aza-peptide epoxides include but are not limited to stroke, Alzheimer's disease, Parkinson's disease, Huntington's disease, multiple sclerosis and other demyelinating diseases, neuropathies including those due to genetic mutations and peripheral neuropathies induced by anti-cancer agents, axonal degeneration, metabolic derangements (eg diabetes, uremia) and idiopathic disorders, spinocerebellar atrophies, amyotrophic lateral sclerosis (ALS) and other motor neuron diseases, and traumatic injuries to the central and peripheral nervous systems.

In another aspect, the present disclosure provides methods for the treatment and/or prevention of nerve degeneration induced by neurotoxic agents and/or anti-cancer agents. Such methods include administration of a composition including an aza-peptide epoxide, and in particular aza-peptide epoxides having small hydrophobic alkyl amino acid residues at P2 and/or aza-peptides having acidic amino acid residues at P1 and/or aza-peptide epoxides that are effective caspase inhibitors. In other aspects, the methods include administration of a composition including an aza-peptide epoxide and a calpain inhibitor. In yet other aspects, the methods include administration of a composition including an aza-peptide epoxide prior to or simultaneous with administration of an anti-cancer drug.

In another aspect, the present disclosure provides a method to identify proteolytic enzymes and a method to prevent proteolysis.

DETAILED DESCRIPTION

Figure 1:
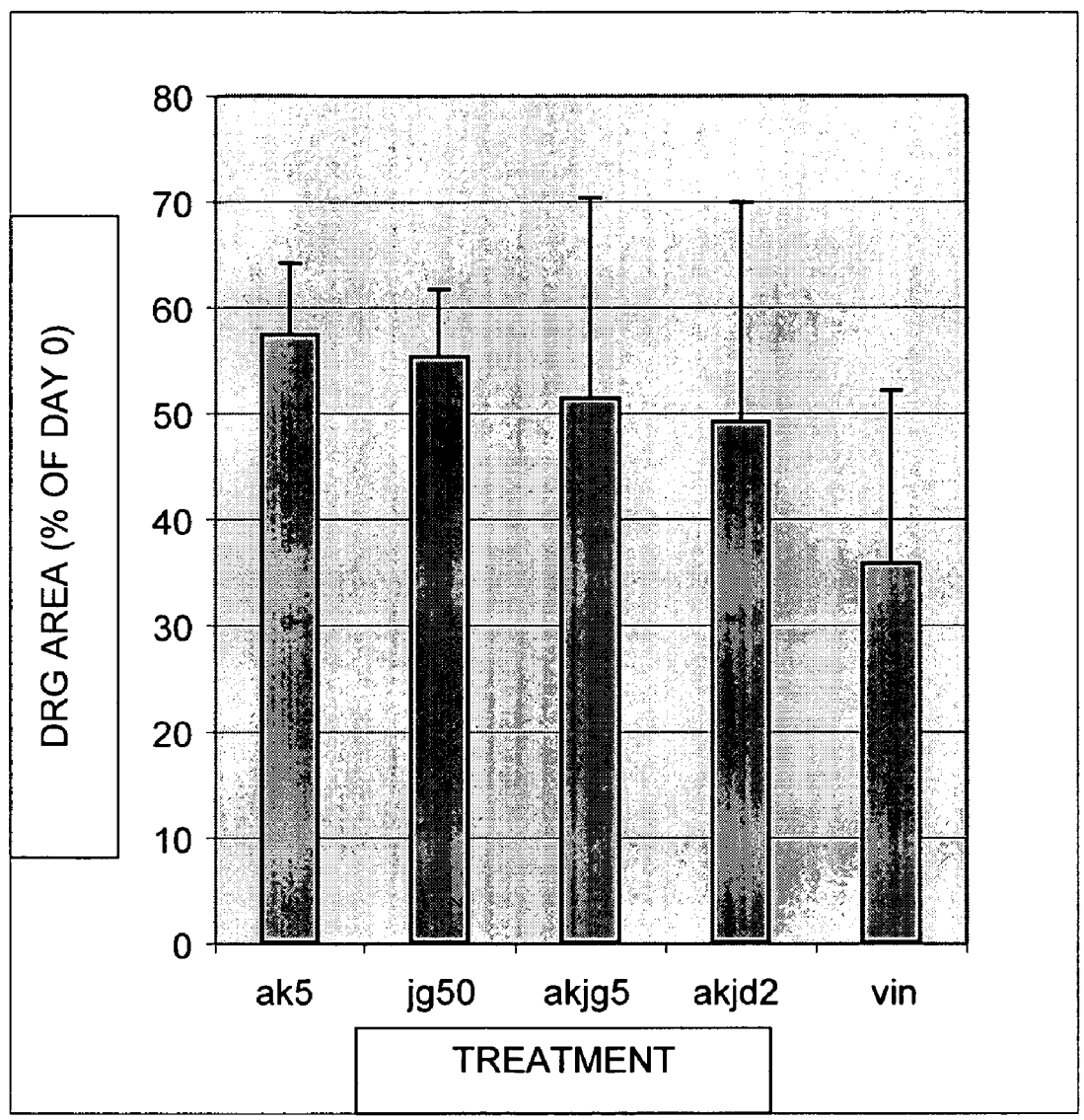
FIG. 1 is a bar graph showing quantitative measure of relative protection of calpain inhibitor AK295, aza-peptide epoxide JG36, and a combination of AK295 and JG36 against vincristine-induced axonal degeneration at 6 days after treatment.

The present disclosure may be understood more readily by reference to the following detailed description and the Examples included therein.

Before the present compounds, compositions and methods are disclosed and described, it is to be understood that this disclosure is not limited to specific synthetic methods, specific pharmaceutical carriers, or to particular pharmaceutical formulations or administration regimens, as such may, of course, vary. It is also to be understood that the terminology used herein is for the purpose of describing particular embodiments only and is not intended to be limiting.

Cysteine Proteases. The aza-peptide epoxide compositions provided herein inhibit enzymatic cleavage of proteins or peptides, or a combination thereof. Exemplary enzymes inhibited by aza-peptide epoxides include cysteine proteases, for example, calpain. Calpain uses a cysteine residue in the catalytic mechanism in contrast to serine proteases which utilize a serine residue. Exemplary cysteine proteases include papain, cathepsin B, calpains, caspases, gingipain, clostripain, legumain, and several viral enzymes.

Caspases are a recently discovered family of cysteine endoproteases, which are highly selective for Asp at the P1 residue. As a result, this newly emerging family of proteases has been called caspases (cysteinyl aspartate-specific protease). All caspases contain the conserved pentapeptide active site motif Gln-Ala-Cys-X-Gly (QACXG)(SEQ. ID NO. 1), where X=Arg, Gln, Gly (R, Q, G), and are synthesized as inactive proenzymes. The only other mammalian protease with specificity for Asp is the lymphocyte serine protease, granzyme B. Many of the proteolytic cleavages that are observed during apoptosis and cytokine maturation are due to the action of various caspases. Indeed, many of the procaspases are activated by other caspases, which selectively cleave at P1 Asp residues in their recognition sites.

At present, there are 14 homologous members of the caspase family in humans. Some caspases are important mediators of inflammation, where they are involved in the production of inflammatory cytokines, and others are involved in apoptosis, where they participate in signaling and effector pathways. Group I (1, 4, 5, 11, 12, 13, and 14) caspases are primarily mediators of inflammation and are involved in proteolytic activation of proinflammatory cytokines. Caspase-1 is also involved in the Fas and TNFR apoptotic pathway. Group II (2, 3, and 7) caspases are late phase effectors of apoptosis and are involved in the cleavage of key structural and homeostatic proteins. Caspase-3, also known as CPP32 (cysteine protease protein 32-kDa), Yama or apopain, is believed to be one of the major effectors in apoptosis. This enzyme is a key executioner because it is responsible either partially or totally for proteolytic cleavage of key apoptotic proteins. It functions to decrease or destroy essential homeostatic pathways during the effector phase of apoptosis. Caspase-3 cleaves or activates nuclear enzymes, such as poly (ADP-ribose) polymerase (PARP), the 70 kDa subunit of the U1 small ribonucleoprotein, the catalytic subunit of DNA-dependent protein kinase, and protein kinase Cδ. Group III (6, 8, 9, 10) caspases are involved in the upstream early activation of effector caspases. Studies have shown that caspase-8 and 10 can cleave radiolabeled precursors for caspase-3. Caspase-6 is the only known caspase that cleaves the lamins, the major structural proteins in the nuclear envelope. Proteolysis of lamins is observed in cells undergoing apoptosis. Caspase-8 (MACH/FLICE), which can cleave all other known caspases, is suggested to lie in the pinnacle of the apoptotic cascade, at least when apoptosis is initiated by some stimuli such as Fas-L and TNF. Accordingly, the present disclosure encompasses compositions and methods of altering, inhibiting, or reducing the formation of enzymatic reaction products involving cysteine proteases. Inhibiting the formation of cysteine protease reaction products in vivo can provide therapeutic effects to patients suffering from unregulated or Caspases have a specificity for at least the four amino acids to the left of the cleavage site (P side). The S4 subsite is the single most important determinant of specificity among caspases after the P1 Asp. The optimal sequences of the caspases were obtained using a positional-scanning combinatorial substrate library (PS-CSL). The optimal recognition sequences for these enzymes are closely related to the sequences found in known macromolecular substrates. Group I caspases' optimal sequence is Trp-Glu-His-Asp (WEHD) (SEQ. ID NO. 2) with S4 favoring hydrophobic amino acids. Group II caspases' optimal sequence is Asp-Glu-X-Asp (DEXD) (SEQ. ID NO. 3) with a requirement for Asp in S4. Group III caspases' optimal sequence is N-Glu-X-Asp where N=Val or Leu and X can be any amino acid ((V,L)EXD) (SEQ. ID NO. 4) with a preference for branched, aliphatic side chains in S4. The S3 subsite prefers glutamic acid (E) in most of the caspases which could be explained by the salt link between Arg-341 (involved in stabilization of the P1 aspartic acid) and the glutamic acid in P3.

Neural tissues, including brain, are known to possess a large variety of proteases, including at least two calcium stimulated proteases termed calpains. Calpains are present in many tissues in addition to the brain. Calpain I is activated by micromolar concentrations of calcium while calpain II is activated by millimolar concentrations. In the brain, calpain II is the predominant form, but calpain I is found at synaptic endings and is thought to be the form involved in long term potentiation, synaptic plasticity, and cell death. Other $Ca^{2+}$ activated cysteine proteases may exist, and the term "calpain" is used to refer to all $Ca^{2+}$ activated cysteine proteases, including calpain I and calpain II. The terms "calpain I" and "calpain II" are used herein to refer to the micromolar and millimolar activated calpains, respectively, as described above. While calpains degrade a wide variety of protein substrates, cytoskeletal proteins seem to be particularly susceptible to attack. In some cases, the products of the proteolytic digestion of these proteins by calpain are distinctive and persistent over time. Since cytoskeletal proteins are major components of certain types of cells, this provides a simple method of detecting calpain activity in cells and tissues. Activation of calpains and/or accumulation of breakdown products of cytoskeletal elements have been observed in neural tissues of mammals exposed to a wide variety of neurodegenerative diseases and conditions. For example, these phenomena have been observed following ischemia in gerbils and rats, following stroke in humans, following administration of the toxins kainate, trimethyltin, or colchicine in rats, and in human Alzheimer's disease.

Cathepsin B is involved in muscular dystrophy, myocardial tissue damage, tumor metastasis, and bone resorption. In addition, a number of viral processing enzymes, which are essential for viral infection, are cysteine proteases. Inhibitors of cysteine proteases would have multiple therapeutic uses.

Other important cysteine proteases are the bacterial enzymes clostripain and gingipain. Gingipain causes tissue destruction during periodontal diseases. Legumain is a related cysteine proteases which is involved in inflammatory diseases. Separin is involved in separation of sister chromatids during cell division.

The present disclosure includes all hydrates, solvates, complexes and prodrugs of the compounds of this disclosure. The term prodrug refers to a pharmacologically inactive compound that is converted to an active drug by a metabolic biotransformation. Prodrugs include compounds wherein an amino acid residue, or a polypeptide chain of two or more (e.g., two, three or four) amino acid residues is covalently joined through an amide or ester bond to a free amino, hydroxy or carboxylic acid group of compounds of Formula I. Additional types of prodrugs are also encompassed. For instance, free carboxyl groups can be derivatized as amides or alkyl esters. The amide and ester moieties may incorporate groups including but not limited to ether, amine and carboxylic acid functionalities. Free hydroxy groups may be derivatized using groups including but not limited to hemisuccinates, phosphate esters, dimethylaminoacetates, and phosphoryloxymethyloxycarbonyls, as outlined in D. Fleisher, R. Bong, B. H. Stewart, Advanced Drug Delivery Reviews (1996) 19, 115. Carbamate prodrugs of hydroxy and amino groups are also included, as are carbonate prodrugs and sulfate esters of hydroxy groups. Derivatization of hydroxy groups as (acyloxy)methyl and (acyloxy)ethyl ethers wherein the acyl group may be an alkyl ester, optionally substituted with groups including but not limited to ether, amine and carboxylic acid functionalities, or where the acyl group is an amino acid ester as described above, are also encompassed. Prodrugs of this type are described in R. P. Robinson et al., J. Medicinal Chemistry (1996) 39, 10.

The subject disclosure also includes isotopically-labelled compounds, and the pharmaceutically acceptable salts thereof, which are identical to those recited in Formula I, but for the fact that one or more atoms are replaced by an atom having an atomic mass or mass number different from the atomic mass or mass number usually found in nature. Examples of isotopes that can be incorporated into compounds of the present disclosure include isotopes of hydrogen, carbon, nitrogen, oxygen, phosphorous, fluorine and chlorine. Compounds of the present disclosure, prodrugs thereof, and pharmaceutically acceptable salts of said compounds or of said prodrugs which contain the aforementioned isotopes and/or other isotopes of other atoms are within the scope of this disclosure. Certain isotopically-labelled compounds of the present disclosure, for example those into which radioactive isotopes such as $^3H$ and $^{14}C$ are incorporated, are useful in drug and/or substrate tissue distribution assays. Tritiated, i.e., $^3H$, and carbon-14, i.e., $^{14}C$, isotopes are particularly preferred for their ease of preparation and detectability. Further, substitution with heavier isotopes such as deuterium, i.e., $^2H$, can afford certain therapeutic advantages resulting from greater metabolic stability, for example increased in vivo half-life or reduced dosage requirements and, hence, may be preferred in some circumstances. Isotopically labelled compounds of Formula 1 of this disclosure and prodrugs thereof can generally be prepared by carrying out the procedures disclosed in the Schemes and/or in the Examples and Preparations below, by substituting a readily available isotopically labelled reagent for a non-isotopically labelled reagent.

If a chiral center or another form of an isomeric center is present in a compound of the present disclosure, all forms of such isomer or isomers, including enantiomers and diastereomers, are intended to be covered herein. Inventive compounds containing a chiral center may be used as a racemic mixture, an enantiomerically enriched mixture, or the racemic mixture may be separated using well-known techniques and an individual enantiomer may be used alone. An enantiomerically enriched mixture means a mixture having greater than about 50% of a single enantiomer. In cases in which compounds have unsaturated carbon-carbon double bonds, both the cis (Z) and trans (E) isomers are within the scope of this disclosure. The compositions of the present disclosure can be substantially optically pure. Substantially optically pure means a composition having greater than 90%, preferably greater than 95%, most preferably greater than 98% of a single optical isomer.

It must be noted that, as used in the specification and the appended claims, the singular forms "a," "an" and "the" include plural referents unless the context clearly dictates otherwise. Thus, for example, reference to "an aromatic compound" includes mixtures of aromatic compounds, reference to "a pharmaceutical carrier" includes mixtures of two or more stitch carriers, and the like.

In discussing the interactions of peptides with cysteine proteases, we have utilized the nomenclature of Schechter and Berger [Biochem. Biophys. Res. Commun. 27, 157-162 (1967); incorporated herein by reference]. The individual amino acid residues of a substrate or inhibitor are designated P1, P2, etc. and the corresponding subsites of the enzyme are designated S1, S2, etc. The scissile bond of the substrate is S1-S1'. The most important recognition subsites of cysteine proteases are S1 and S2.

Amino acid residues and blocking groups are designated using standard abbreviations [see J. Biol. Chem. 260, 14-42 (1985) for nomenclature rules; incorporated herein by reference]. An amino acid residue (AA) in a peptide or inhibitor structure refers to the part structure —NH—$CHR_1$—CO—, where $R_1$ is the side chain of the amino acid residue AA. It will be appreciated that at least one of the amino acid residues of the aza-peptide epoxides of the present disclosure may be substituted by one of the well known non-naturally occurring amino acid residues. Alterations such as these may serve to increase the stability, bioavailability and/or inhibitory action of the peptides of the present disclosure. Moreover, any of the aza-peptide epoxides described herein may, additionally, have a non-peptide macromolecular carrier group covalently attached to their amino and/or carboxy termini. Such macromolecular carrier groups may include, for example, lipid-fatty acid conjugates, polyethylene glycol, or carbohydrates.

The following figure shows the structure of an aza-peptide epoxide. An aza-amino acid residue is an alpha-amino acid residue where the alpha-carbon has been replaced by a nitrogen atom. It will be abbreviated as the three letter code for the amino acid preceded by an "A". Therefore, aza-alanine will be abbreviated as AAla and aza-aspartic acid as AAsp. The epoxide will be abbreviated as EP for the $C_2H_2O$ residue.

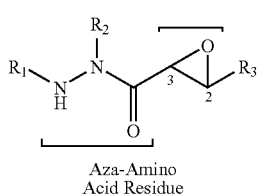

epoxide (EP)

Aza-Amino Acid Residue

The complete structures of several aza-peptide epoxides and their abbreviated structures are shown in the following figure.

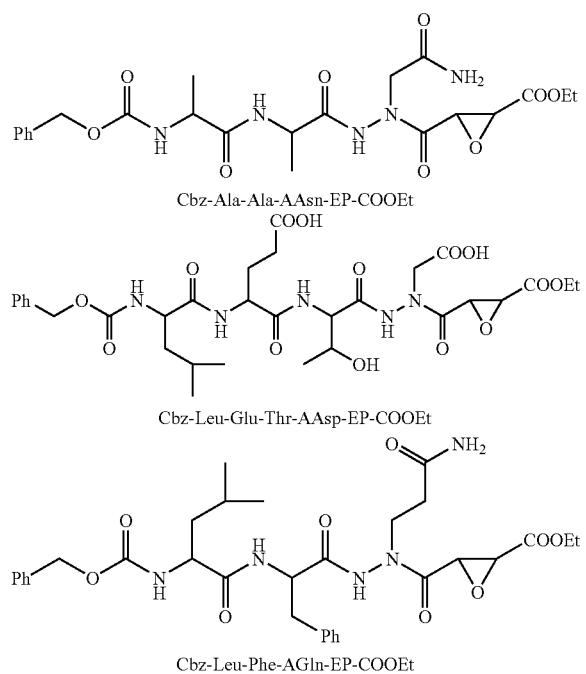

Cbz-Ala-Ala-AAsn-EP-COOEt

Cbz-Leu-Glu-Thr-AAsp-EP-COOEt

Cbz-Leu-Phe-AGln-EP-COOEt

The $R_3$ group would be abbreviated as $CO_2H$, $CO_2Et$, $CO_2R$, CONHR, CONRR', or CO-AA-T if the aza-peptide epoxide has an epoxysuccinate moiety in its structure. Otherwise, the structure of the $R_3$ group would be drawn or abbreviated.

There are four structural isomers at the epoxide moiety, two trans isomers (2S,3S and 2R,3R) and two cis isomers (2R,3S and 2S,3R). The numbering of the carbons of the epoxide is shown above. The epoxide ring is also known as an oxirane ring.

The term "amino," as used herein, refers to $-NH_2$ or derivatives thereof formed by independent replacement of one or both hydrogen atoms thereon with a substituent or substituents independently selected from alkyl, alkanoyl, aryl, arylalkyl, cycloalkyl, cycloalkylalkyl, heteroaryl, heteroarylalkyl, and an amino protecting group.

The term "$C_{10}$ acyl," as used herein, refers to a $C_{1-10}$ alkyl group, as defined herein, having an attached carbonyl group.

The term "$C_{1-10}$ alkoxy," as used herein, refers to a $C_{1-10}$ alkyl group, as defined herein, attached to the parent molecular group through an oxygen atom.

The term "$C_{10}$ alkyl" as used herein refers to a branched or unbranched hydrocarbon group of carbon atoms, such as methyl, ethyl, n-propyl, isopropyl, n-butyl, isobutyl, 1-butyl, and the like or branched or unbranched hydrocarbon groups of carbon atoms that either contain double or triple carbon bonds.

The term "$C_{1-10}$ alkylamino," as used herein, refers to a $C_{1-10}$ alkyl group, as defined herein, to which is attached at least one amino substituent.

The term "$C_{3-15}$ cycloalkyl" as applied herein is meant to include cyclic hydrocarbon chains. Examples of these cyclic hydrocarbon chains include cyclopropane, cyclobutane, cyclopentane, cyclohexane, cycloheptane, cyclooctane, cyclononane, cyclodecane, cycloundecane, etc.

The term "$C_{2-12}$ dialkylamino," as used herein, refers to two $C_{1-10}$ alkyl groups, as defined herein, that are attached to an amino substituent.

The term "$C_{1-10}$ fluoroalkyl," as used herein, refers to a $C_{1-10}$ alkyl group, as defined herein, to which is attached at least one fluorine substituent.

The term "$C_{1-10}$ perfluoroalkyl," as used herein, refers to a $C_{1-10}$ alkyl group in which all of the hydrogen atoms have been replaced with fluorine atoms.

The term "biotinyl," as used herein, refers to biotin without the biotin carboxyl hydroxyl group.

The term "neurotoxin" as used herein, refers to a compound that adversely affects cells of the nervous system. Suitable neurotoxins include compounds that induce axonal degeneration, for example by interfering with the neuronal cytoskeleton, in particular with microtubules. Microtubule stabilizers, for example Taxol® and Taccalonolides E and A, are preferred neurotoxins of the present disclosure. Taccalonolides E and A are described in Tinley T L et al. (2003) *Taccalonolides E and A: Plant-derived steroids with microtubule-stabilizing activity*. Cancer Res. June 15;63(12):3211-20, which is incorporated by reference in its entirety. Colchicine, colcemid, nocadazol, vinblastine and vincristine are additional exemplary neurotoxins that affect microtubules.

The term "Taxol®" is intended to be interchangeable with paclitaxel and refers to 5-beta,20-epoxy-1,2-alpha,4,7-beta, 10-beta, 13-alpha-hexahydroxy-tax-11-en-9-one 4,10-diacetate 2-benzoate 13-ester with (2R,3S)-N-benzoyl-3-phenylisoserine; 7,11-Methano-5H-cyclodeca[3,4]benz[1,2-b]oxete,benzenepropanoic acid derivative; Paclitaxel; TAX; Taxal; Taxol; Taxol A; substantially pure optical isomers, racemates, prodrugs, and derivatives thereof. The structure of paclitaxel is provided below.

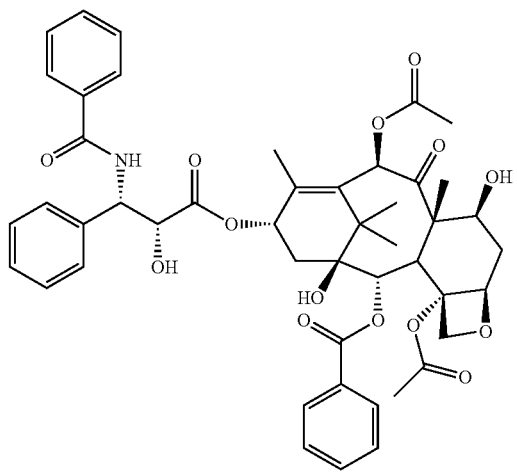

The term "anti-hyperproliferative agent" as used herein, refers to a substance that reduces, inhibits or interferes with aberrant cell growth or division. Exemplary anti-hyperproliferative agents include but are not limited to anti-cancer agents such as paclitaxel, chemotherapy agents, anti-sense polynucleotides, enzymatic polynucleotides, polypeptides, dideoxy nucleotides, chain terminating nucleotides, antibodies, and small molecules.

The term "hyperproliferative disorder" as used herein, refers to a pathology resulting from aberrant cell growth or division.

The term "calpain related pathology" as used herein, refers to an abnormal cellular or systemic condition or symptom directly or indirectly caused, in part or in whole, by the activity of a calpain protease.

By the term "effective amount" of a compound as provided herein is meant a nontoxic but sufficient amount of the compound to provide the desired utility. As will be pointed out below, the exact amount required will vary from subject to subject, depending on the species, age, and general condition of the subject, the severity of the condition or disease that is being treated, the particular compound used, its mode of administration, and the like. Thus, it is not possible to specify an exact "effective amount." However, an appropriate effective amount may be determined by one of ordinary skill in the art using only routine experimentation.

The term "pharmaceutically acceptable salt(s)", as used herein, unless otherwise indicated, includes salts of acidic or basic groups which may be present in the compounds of Formula I. The compounds of Formula I that are basic in nature are capable of forming a wide variety of salts with various inorganic and organic acids. The acids that may be used to prepare pharmaceutically acceptable acid addition salts of such basic compounds of Formula I are those that form non-toxic acid addition salts, i.e., salts containing pharmacologically acceptable anions, such as the hydrochloride, hydrobromide, hydroiodide, nitrate, sulfate, bisulfate, phosphate, acid phosphate, isonicotinate, acetate, lactate, salicylate, citrate, acid citrate, tartrate, TFA, pantothenate, bitartrate, ascorbate, succinate, maleate, gentisinate, fumarate, gluconate, glucaronate, saccharate, formate, benzoate, glutamate, methanesulfonate, ethanesulfonate, benzenesulfonate, p-toluenesulfonate and pamoate [i.e., 1,1'-methylene-bis-(2-hydroxy-3-naphthoate)] salts. Those compounds of the Formula I that are acidic in nature, are capable of forming base salts with various pharmacologically acceptable cations. Examples of such salts include the alkali metal or alkaline earth metal salts and particularly, the sodium and potassium salts.

The term "pharmaceutically acceptable derivative" refers to any homolog, analog, or fragment corresponding to the aza-peptide epoxides of the present disclosure provided herein which inhibits protease activity and is relatively nontoxic to the subject or host.

The term "pharmaceutically acceptable" means a material that is not biologically or otherwise undesirable, i.e., the material may be administered to an individual along with the selected bicyclic compound without causing any undesirable biological effects or interacting in a deleterious manner with any of the other components of the pharmaceutical composition in which it is contained.

As used herein, and without limitation, the term "derivative" is used to refer to any compound which has a structure derived from the structure of the compounds of the present disclosure and whose structure is sufficiently similar to those disclosed herein and based upon that similarity, would be expected, by one skilled in the art, to exhibit the same or similar activities and utilities as the claimed compounds.

As used herein, "treat", "treating", and "treatment" are an approach for obtaining beneficial or desired clinical results. For purposes of embodiments of this disclosure, beneficial or desired clinical results include, but are not limited to, preventing and/or inhibiting the condition/disease from occurring in an animal that may be at risk for or predisposed to the condition/disease but does not yet experience or exhibit symptoms of the disease (prophylactic treatment), alleviation and/or inhibition of symptoms of the condition/disease, diminishment of extent of condition/disease, stabilization (i.e., not worsening) of condition/disease, preventing/inhibiting spread of condition/disease, delaying or slowing of condition/disease progression, amelioration or palliation of the condition/disease state, and combinations thereof.

The following abbreviations have also been used: AFC, 7-amino-4-trifluoromethylcoumarin; AAsp, aza-aspartic acid residue; AAsn, aza-asparagine; ALeu, aza-leucine; ALys, aza-lysine residue; AHph, aza-homophenylalanine residue; AOrn, aza-ornithine; AMC, 7-amino-4-methylcoumarin; Cbz, Ph-CH$_2$OCO—; DCC, 1,3-dicyclohexylcarbodiimide; DMAP, 4-dimethylaminopyridine; DMF, N,N-dimethylformamide; EDC, 1-(3-dimethylaminopropyl)-3-ethylcarbodiimide hydrochloride; EtOAc, ethyl acetate; HOBt, 1-hydroxybenzotriazole; HRMS, high resolution mass spectrometry; IBCF, isobutyl chloroformate; NMM, 4-methylmorpholine; Np2,2-naphthyl-alanyl; PhPr, Phenylpropyl; TFA, trifluoroacetic acid; THF, tetrahydrofuran; TLC, thin layer chromatography.

One embodiment of the present disclosure provides aza-peptide epoxides having the following structural Formula I:

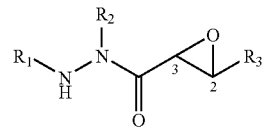

wherein,

R$_1$ is selected from the group consisting of M$_1$, M$_2$-AA$_1$, M$_2$-AA$_2$-AA$_1$, and M$_2$-AA$_3$-AA$_2$-AA$_1$;

M$_1$ is selected from the group consisting of NH$_2$—CO—, NH$_2$—CS—, NH$_2$—SO$_2$—, X—NH—CO—, X$_2$N—CO—, X—NH—CS—, X$_2$N—CS—, X—NH—SO$_2$—, X$_2$N—SO$_2$—, X—CO—, X—CS—, Y—SO$_2$—, Y—O—CO—, Y—O—CS—, phenyl substituted with K, phenyl disubstituted with K, and morpholine-CO—;

M$_2$ is selected from the group consisting of H, NH$_2$—CO—, NH$_2$—CS—, NH$_2$—SO$_2$—, X—NH—CO—, X$_2$N—CO—, X—NH—CS—, X$_2$N—CS—, X—NH—SO$_2$—, X$_2$N—SO$_2$—, X—CO—, X—CS—, Y—SO$_2$—, Y—O—CO—, Y—O—CS—, phenyl, phenyl substituted with K, phenyl disubstituted with K, and morpholine-CO—;

X is selected from the group consisting of H, C$_{1-10}$ alkyl, C$_{3-15}$ cyclized alkyl, C$_{1-10}$ fluoroalkyl, C$_{1-10}$ alkyl substituted with J, C$_{1-10}$ fluoroalkyl substituted with J, 1-admantyl, 9-fluorenyl, phenyl, phenyl substituted with K, phenyl disubstituted with K, phenyl trisubstituted with K, naphthyl, naphthyl substituted with K, naphthyl disubstituted with K, naphthyl trisubstituted with K, C$_{1-10}$ fluoroalkyl with an attached phenyl group, C$_{1-10}$ alkyl with an attached phenyl group, C$_{1-10}$ alkyl with two attached phenyl groups, C$_{1-10}$ alkyl with an attached phenyl group substituted with K, C$_{1-10}$ alkyl with two attached phenyl groups substituted with K, C$_{1-10}$ alkyl with an attached naphthyl group, C$_{1-10}$ alkyl with an attached naphthyl group substituted with K, C$_{1-10}$ alkyl with an attached phenoxy group, biotinyl, and C$_{1-10}$ alkyl with an attached phenoxy group substituted with K on the phenoxy group;

Y is selected from the group consisting of $C_{1-10}$ alkyl, $C_{3-15}$ cyclized alkyl, $C_{1-10}$ fluoroalkyl, $C_{1-10}$ alkyl substituted with J, $C_{1-10}$ fluoroalkyl substituted with J, 1-admantyl, 9-fluorenyl, phenyl, phenyl substituted with K, phenyl disubstituted with K, phenyl trisubstituted with K, naphthyl, naphthyl substituted with K, naphthyl disubstituted with K, naphthyl trisubstituted with K, $C_{1-10}$ fluoroalkyl with an attached phenyl group, $C_{1-10}$ alkyl with an attached phenyl group, $C_{1-10}$ alkyl with two attached phenyl groups, $C_{1-10}$ alkyl with an attached phenyl group substituted with K, $C_{1-10}$ alkyl with two attached phenyl groups substituted with K, $C_{1-10}$ alkyl with an attached naphthyl group, $C_{1-10}$ alkyl with an attached naphthyl group substituted with K, $C_{1-10}$ alkyl with an attached phenoxy group, biotinyl, and $C_{1-10}$ alkyl with an attached phenoxy group substituted with K on the phenoxy group;

J is selected from the group consisting of halogen, $CO_2H$, OH, CN, $NO_2$, $NH_2$, $C_{1-10}$ alkoxy, $C_{1-10}$ alkylamino, $C_{2-12}$ dialkylamino, $C_{1-10}$ alkyl-O—CO—, $C_{1-10}$ alkyl-O—CO—NH—, and $C_{1-10}$ alkyl-S—;

K is selected from the group consisting of halogen, $C_{10}$ alkyl, $C_{10}$ perfluoroalkyl, $C_{1-10}$ alkoxy, phenoxy, $NO_2$, CN, OH, $CO_2H$, amino, $C_{1-10}$ alkylamino, $C_{2-12}$ dialkylamino, $C_{1-10}$ acyl, and $C_{1-10}$ alkoxy-CO—, and $C_{1-10}$ alkyl-S—;

$AA_1$, $AA_2$, and $AA_3$ are side chain blocked or unblocked amino acids with the L configuration, D configuration, or no chirality at the α-carbon selected from the group consisting of alanine, valine, leucine, isoleucine, proline, methionine, methionine sulfoxide, phenylalanine, tryptophan, glycine, serine, threonine, cysteine, tyrosine, asparagine, glutamine, aspartic acid, glutamic acid, lysine, arginine, histidine, phenylglycine, beta-alanine, norleucine, norvaline, alpha-aminobutanoic acid, epsilon-aminocaproic acid, citrulline, hydroxyproline, ornithine, homoarginine, sarcosine, indoline 2-carboxylic acid, 2-azetidinecarboxylic acid, pipecolinic acid (2-piperidine carboxylic acid), O-methylserine, O-ethylserine, S-methylcysteine, S-ethylcysteine, S-benzylcysteine, $NH_2$—$CH(CH_2CHEt_2)$—$CO_2H$, alpha-aminoheptanoic acid, $NH_2$—$CH(CH_2$-1-naphthyl)-$CO_2H$, $NH_2$—CH$(CH_2$-2-naphthyl)-$CO_2H$, $NH_2$—$CH(CH_2$-cyclohexyl)-$CO_2H$, $NH_2$—$CH(CH_2$-cyclopentyl)-$CO_2H$, $NH_2$—CH$(CH_2$-cyclobutyl)-$CO_2H$, $NH_2$—$CH(CH_2$-cyclopropyl)-$CO_2H$, trifluoroleucine, 4-fluorophenylalanine, lysine substituted on the epsilon nitrogen with a biotinyl group, and hexafluoroleucine;

$R_2$ is selected from the group consisting of $C_{1-10}$ alkyl, $C_{1-10}$ alkyl substituted with Q, $C_{1-10}$ alkyl substituted with phenyl, $C_{1-10}$ alkyl with an attached phenyl substituted with K, $C_{1-10}$ alkyl substituted with naphthyl, $C_{1-10}$ alkyl with an attached naphthyl substituted with K, phenyl, phenyl substituted with K, naphthyl, naphthyl substituted with K, $C_{1-10}$ alkyl substituted with $CONH_2$, $C_{1-10}$ alkyl substituted with $CONHR_4$, $C_{1-10}$ alkyl substituted with $CO_2H$, $C_{1-10}$ alkyl substituted with $CO_2R_4$, $CH_2CH_2SCH_3$, $CH_2$-3-indolyl, $CH_2$-2-thienyl, $CH_2$-2-furyl, $CH_2$-3-furyl, $CH_2$-2-imidazyl, $C_{1-10}$ alkyl substituted with G, $C_{1-10}$ alkyl with an attached phenyl substituted with G, $C_{1-10}$ alkyl with an attached naphthyl substituted with G, phenyl substituted with G, and naphthyl substituted with G;

$R_4$ is selected from the group consisting of $C_{1-10}$ alkyl and $C_{1-10}$ alkyl substituted with phenyl;

Q is selected independently from the group consisting of $C_{1-10}$ alkoxy, $C_{1-10}$ alkyl-S—, $C_{1-10}$ alkoxy substituted with phenyl, and $C_{1-10}$ alkyl-S— substituted with phenyl;

G is selected independently from the group consisting of amidino (—C(=NH)$NH_2$), guanidino (—NHC(=NH)$NH_2$), isothiureido (—S—C(=NH)$NH_2$), amino, $C_{1-6}$ alkylamino, $C_{2-12}$ dialkylamino, and imidazyl;

$R_3$ is selected independently from the group consisting of $R_5$, $CO_2H$, $CO_2R_5$, $CONHR_6$, $CONR_6R_7$, CO-$AA_4$-T,

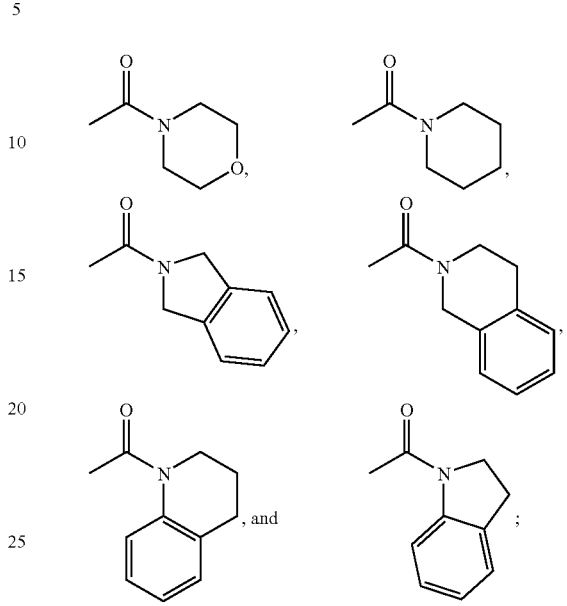

$R_5$ is selected independently from the group consisting of $C_{1-10}$ alkyl, $C_{3-15}$ cyclized alkyl, $C_{1-10}$ alkyl with a phenyl group attached to the $C_{1-10}$ alkyl, $C_{3-15}$ cyclized alkyl with an attached phenyl group, $C_{1-10}$ alkyl with an attached phenyl group substituted with K, $C_{1-10}$ alkyl with an attached phenyl group disubstituted with K, $C_{1-10}$ alkyl with an attached phenyl group trisubstituted with K, $C_{3-15}$ cyclized alkyl with an attached phenyl group substituted with K, $C_{1-10}$ alkyl with a naphthyl group attached to the $C_{1-10}$ alkyl, $C_{3-15}$ cyclized alkyl with an attached naphthyl group, $C_{1-10}$ alkyl with an attached naphthyl group substituted with K, $C_{1-10}$ alkyl with an attached naphthyl group disubstituted with K, $C_{1-10}$ alkyl with an attached naphthyl group trisubstituted with K, and $C_{3-15}$ cyclized alkyl with an attached naphthyl group substituted with K;

T is selected independently from the group consisting of OH, $OR_8$, $NHR_9$, and $NR_8R_9$;

$AA_4$ is a side chain blocked or unblocked amino acid with the L configuration, D configuration, or no chirality at the α-carbon selected from the group consisting of alanine, valine, leucine, isoleucine, proline, methionine, methionine sulfoxide, phenylalanine, tryptophan, glycine, serine, threonine, cysteine, tyrosine, asparagine, glutamine, aspartic acid, glutamic acid, lysine, arginine, histidine, phenylglycine, beta-alanine, norleucine, norvaline, alpha-aminobutanoic acid, epsilon-aminocaproic acid, citrulline, hydroxyproline, ornithine, homoarginine, sarcosine, indoline 2-carboxylic acid, 2-azetidinecarboxylic acid, pipecolinic acid (2-piperidine carboxylic acid), O-methylserine, O-ethylserine, S-methylcysteine, S-ethylcysteine, S-benzylcysteine, $NH_2$—CH$(CH_2CHEt_2)$—$CO_2H$, alpha-aminoheptanoic acid, $NH_2$—$CH(CH_2$-1-naphthyl)-$CO_2H$, $NH_2$—$CH(CH_2$-2-naphthyl)-$CO_2H$, $NH_2$—$CH(CH_2$-cyclohexyl)-$CO_2H$, $NH_2$—CH$(CH_2$-cyclopentyl)-$CO_2H$, $NH_2$—$CH(CH_2$-cyclobutyl)-$CO_2H$, $NH_2$—$CH(CH_2$-cyclopropyl)-$CO_2H$, trifluoroleucine, 4-fluorophenylalanine, lysine substituted on the epsilon nitrogen with a biotinyl group, and hexafluoroleucine;

$R_6$ and $R_7$ are selected independently from the group consisting of H, $C_{1-10}$ alkyl, $C_{3-20}$ cyclized alkyl, $C_{1-10}$ alkyl with a phenyl group attached to the $C_{1-10}$ alkyl, $C_{1-10}$ alkyl with two phenyl groups attached to the $C_{1-10}$ alkyl, $C_{3-20}$ cyclized alkyl with an attached phenyl group, phenyl, phenyl substituted with K, $C_{1-10}$ alkyl with an attached phenyl group substituted with K, $C_{1-10}$ alkyl with an attached phenyl group disubstituted with K, $C_{1-10}$ alkyl with an attached phenyl group trisubstituted with K, $C_{1-10}$ alkyl with two phenyl groups attached to the $C_{1-10}$ alkyl and substituted with K on the phenyl group, $C_{1-10}$ alkyl with two phenyl groups attached to the $C_{1-10}$ alkyl and disubstituted with K on the phenyl groups, $C_{3-20}$ cyclized alkyl with an attached phenyl group substituted with K, $C_{1-10}$ alkyl with a morpholine [—N($CH_2CH_2$)O] ring attached through nitrogen to the alkyl, $C_{1-10}$ alkyl with a piperidine ring attached through nitrogen to the alkyl, $C_{1-10}$ alkyl with a pyrrolidine ring attached through nitrogen to the alkyl, $C_{1-20}$ alkyl with an OH group attached to the alkyl, —$CH_2CH_2CH_2OCH_3$, $C_{1-10}$ alkyl with an attached 4-pyridyl group, $C_{1-10}$ alkyl with an attached 3-pyridyl group, $C_{1-10}$ alkyl with an attached 2-pyridyl group, $C_{1-10}$ alkyl with an attached cyclohexyl group, —NH—$CH_2CH_2$-(4-hydroxyphenyl), —NH—$CH_2CH_2$-(3-indolyl), $C_{1-10}$ alkyl with an attached 2-furyl group, $C_{1-10}$ alkyl with an attached 3-furyl group, and $C_{1-5}$ alkyl with an attached phenyl and a hydroxyl attached to the $C_{1-5}$ alkyl;

$R_8$ and $R_9$ are selected independently from the group consisting of H, $C_{1-10}$ alkyl, phenyl, nitrophenyl, and $C_{1-0}$ alkyl substituted with phenyl;

the stereochemistry at the epoxide carbons 2 and 3 is selected from the group consisting of cis, trans, R,R, S,S, R,S, and S,R.

The following compounds are representative of the present disclosure:
APhe-(trans)-EP-COOEt,
Cbz-APhe-(trans)-EP-COOEt,
Cbz-APhe-(trans)-EP-CH$_2$CH$_2$Ph,
Cbz-ALeu-(trans)-EP-COOEt,
Cbz-AHph-(trans)-EP-COOEt,
Ac-AHph-(trans)-EP-COOEt,
Boc-Nva-AHph-(trans)-EP-COOEt,
Boc-Nle-AHph-(trans)-EP-COOEt,
Boc-Nle-AHph-(trans)-EP-CH$_2$CH$_2$Ph,
Boc-Nva-AHph-(trans)-EP-CH$_2$CH$_2$Ph,
Boc-Abu-AHph-(trans)-EP-CH$_2$CH$_2$Ph,
Boc-Ala-AHph-(trans)-EP-CH$_2$CH$_2$Ph,
Boc-Np2-ALeu-(trans)-EP-COOEt,
Suc-Np2-ALeu-(trans)-EP-COOEt,
Ac-Leu-ALeu-(trans)-EP-COOEt,
Ac-Leu-AHph-(trans)-EP-COOEt,
Nva-AHph-(trans)-EP-CH$_2$CH$_2$Ph.TFA,
Nle-AHph-(trans)-EP-COOEt.TFA,
Ala-AHph-(trans)-EP-CH$_2$CH$_2$Ph.TFA,
Cbz-Leu-ALeu-(2S,3S)-EP-COOEt,
Cbz-Leu-ALeu-(2R,3R)-EP-COOEt,
Cbz-Leu-ALeu-(trans)-EP-COOEt,
Cbz-Leu-ALeu-(cis)-EP-COOEt,
Cbz-Phe-ALeu-(trans)-EP-COOEt,
Cbz-Phe-ALeu-(trans)-EP-CH$_2$CH$_2$Ph,
Cbz-Phe-APhe-(trans)-EP-CH$_2$CH$_2$Ph,
Cbz-Leu-AAbu-(trans)-EP-COOEt,
Cbz-Leu-AAbu-(trans)-EP-COOH,
Cbz-Leu-AHph-(cis)-EP-COOEt,
Cbz-Leu-AHph-(2S,3S)-EP-COOEt,
Cbz-Leu-AHph-(2R,3R)-EP-COOEt,
Cbz-Leu-AHph-(2S,3S)-EP-COOH,
Cbz-Leu-Leu-ALeu-(trans)-EP-COOEt,
Cbz-Leu-Leu-ALeu-(2S,3S)-EP-COOEt,
Cbz-Leu-Leu-ALeu-(2R,3R)-EP-COOEt,
Cbz-Leu-Leu-ALeu-(2S,3S)-EP-COOH,
Cbz-Leu-Phe-AGln-(2S,3S)-EP-COOEt,
Cbz-Leu-Phe-AGln-(2R,3R)-EP-COOEt,
Cbz-Leu-Phe-AGln-(trans)-EP-COOEt,
Cbz-Ala-Ala-AAsn-(trans)-EP-COOEt,
Cbz-Ala-Ala-AAsn-(2S,3S)-EP-COOEt,
Cbz-Ala-Ala-AAsn-(2R,3R)-EP-COOEt,
Cbz-Ala-Ala-AAsn-(cis)-EP-COOEt,
Cbz-Ala-Ala-AAsn-(trans)-EP-COOCH$_2$Ph,
Cbz-Ala-Ala-AAsn-(S,S)-EP-COOCH$_2$Ph,
Cbz-Ala-Ala-AAsn-(S,S)-EP-COOCH$_2$CH$_2$Ph,
Cbz-Ala-Ala-AAsn-(S,S)-EP-CONHCH$_2$Ph,
Cbz-Ala-Ala-AAsn-(S,S)-EP-CONHCH$_2$CH$_2$Ph,
Cbz-Ala-Ala-AAsn-(R,R)-EP-CO-Ala-NH-Bzl,
Cbz-Ala-Ala-AAsn-(S,S)-EP-CON(nBu)$_2$,
Cbz-Ala-Ala-AAsn-(S,S)-EP-CON(CH$_3$)CH$_2$Ph,
Cbz-Ala-Ala-AAsn-(trans)-EP-CH$_2$CH$_2$Ph,
Cbz-Ala-Ala-AAsn-(trans)-EP-Ph-4-Cl,
Cbz-Ala-Ala-NHN(CH$_2$COOEt)-(trans)-EP-COOEt,
PhPr-Val-Ala-AAsp-(2R,3R)-EP-COOCH$_2$Ph,
PhPr-Val-Ala-AAsp-(2S,3S)-EP-COOCH$_2$Ph,
PhPr-Val-Ala-AAsp-(trans)-EP-COOCH$_2$Ph,
PhPr-Val-Ala-AAsp-(trans)-EP-CH$_2$CH$_2$Ph,
Cbz-Ile-Glu-Thr-AAsp-(2S,3S)-EP-COOEt,
Cbz-Ile-Glu-Thr-AAsp-(2R,3R)-EP-COOEt,
Cbz-Leu-Glu-Thr-AAsp-(2S,3S)-EP-COOEt,
Cbz-Leu-Glu-Thr-AAsp-(2R,3R)-EP-COOEt,
Cbz-Asp-Glu-Val-AAsp-(2S,3S)-EP-COOEt,
Cbz-Asp-Glu-Val-AAsp-(2R,3R)-EP-COOEt,
Cbz-Glu-Val-AAsp-(2S,3S)-EP-COOEt,
PhPr-Val-Ala-AAsp-(2S,3S)-EP-CON(CH$_2$CH$_2$CH$_2$CH$_3$)$_2$,
PhPr-Val-Ala-AAsp-(2S,3S)-EP-CON(CH$_2$Ph)$_2$,
Cbz-Leu-Glu-Thr-AAsp-(2S,3S)-EP-CON(CH$_2$Ph)$_2$,
Cbz-Ile-Glu-Thr-AAsp-(2S,3S)-EP-CON(CH$_2$Ph)$_2$,
Cbz-Leu-Glu-Thr-AAsp-(2S,3S)-EP-CON(CH$_3$)CH$_2$Ph,
PhPr-Val-Ala-AAsp-(2S,3S)-EP-CON(CH$_3$)CH$_2$Ph,
Cbz-Ile-Glu-Thr-AAsp-(2S,3S)-EP-CON(CH$_3$)CH$_2$Ph,
PhPr-Leu-ALys-(2S,3S)-EP-CO$_2$Et,
PhPr-Leu-AOm-(2S,3S)-EP-CO$_2$Et,
Cbz-Val-AAsp-(S,S)-EP-COOEt,
Cbz-Val-AAsp-(S,S)-EP-COOH,
Cbz-Val-AAsp-(trans)-EP-CH$_2$CH$_2$Ph,
Cbz-Val-AAsp-(trans)-EP-Ph-4-Cl,
PhPr-Val-Ala-AAsp-(S,S)-EP-COOEt,
PhPr-Val-Ala-AAsp-(R,R)-EP-COOEt,
PhPr-Val-Ala-AAsp-(S,S)-EP-COOCH$_2$CH$_2$Ph,
PhPr-Val-Ala-AAsp-(S,S)-EP-CONHCH$_2$CH$_3$,
PhPr-Val-Ala-AAsp-(S,S)-EP-CONHCH$_2$Ph,
PhPr-Val-Ala-AAsp-(R,R)-EP-CONHCH$_2$Ph,
PhPr-Val-Ala-AAsp-(S,S)-EP-CONHCH$_2$CH$_2$Ph,
PhPr-Val-Ala-AAsp-(R,R)-EP-CONHCH$_2$CH$_2$Ph,
PhPr-Val-Ala-AAsp-(S,S)-EP-CONHCH$_2$CH(OH)Ph,
PhPr-Val-Ala-AAsp-(R,R)-EP-CONHCH$_2$CH(OH)Ph,
PhPr-Val-Ala-AAsp-(S,S)-EP-CO-Ala-NHCH$_2$Ph,
PhPr-Val-Ala-AAsp-(R,R)-EP-CO-Ala-NHCH$_2$Ph,
PhPr-Val-Ala-AAsp-(S,S)-EP-CO-Leu-NH$_2$,
PhPr-Val-Ala-AAsp-(R,R)-EP-CO-Leu-NH$_2$,
PhPr-Val-Ala-AAsp-(S,S)-EP-CO-Phe-NH$_2$,
PhPr-Val-Ala-AAsp-(R,R)-EP-CO-Phe-NH$_2$,
PhPr-Val-Ala-AAsp-(S,S)-EP-CO-Tyr-NH$_2$,
Cbz-Glu-Val-AAsp-(R,R)-EP-CO-Phe-NH$_2$,
Cbz-Glu-Val-AAsp-(S,S)-EP-CONHCH$_2$CH$_2$Ph,
Cbz-Asp-Glu-Val-AAsp-(S,S)-EP-CO-Phe-NH$_2$,
Cbz-Asp-Glu-Val-AAsp-(S,S)-EP-CONHCH$_2$Ph,
Cbz-Asp-Glu-Val-AAsp-(S,S)-EP-COOCH$_2$Ph, Cbz-Leu-Glu-Thr-AAsp-(S,S)-EP-CONHCH₂CH₂Ph,
Cbz-Leu-Glu-Thr-AAsp-(S,S)-EP-CO-Ala-NHCH₂Ph,
Cbz-Ile-Glu-Thr-AAsp-(S,S)-EP-CO-Ala-NHCH₂Ph,

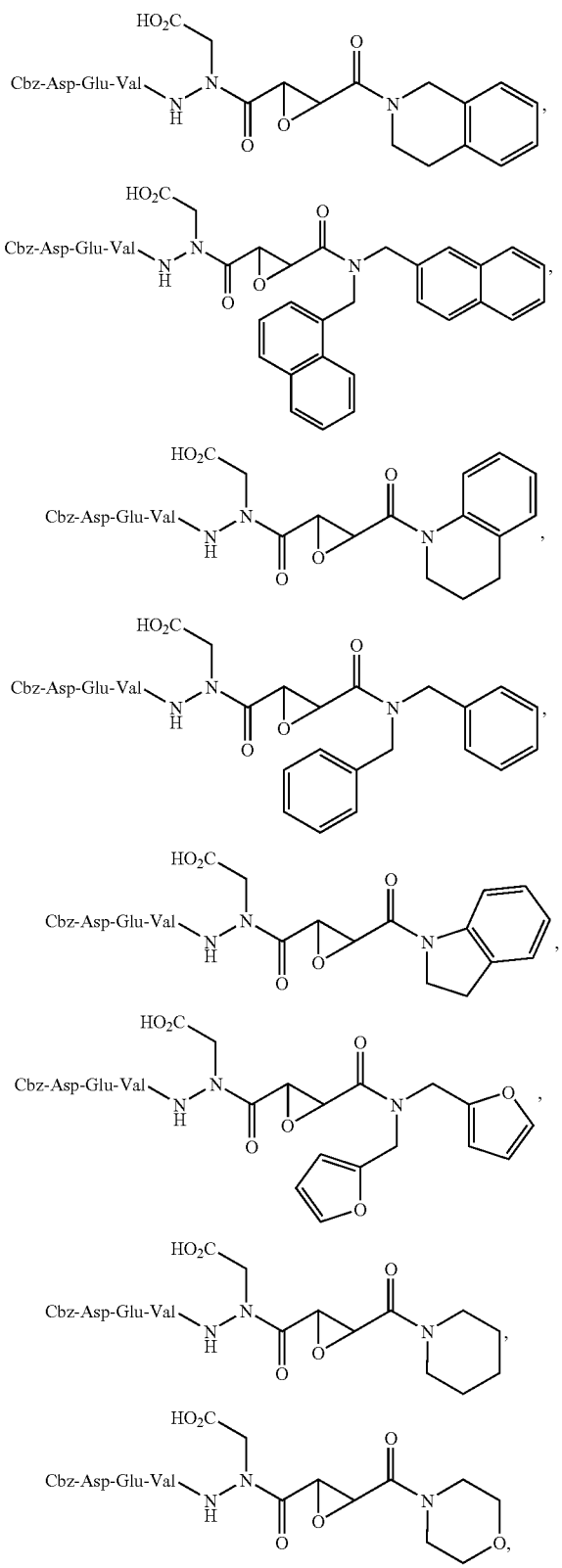

-continued

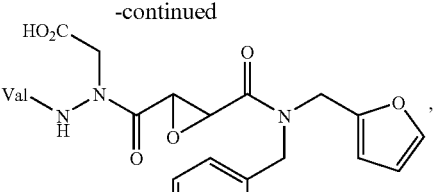

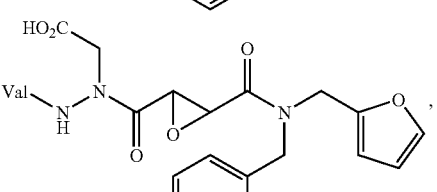

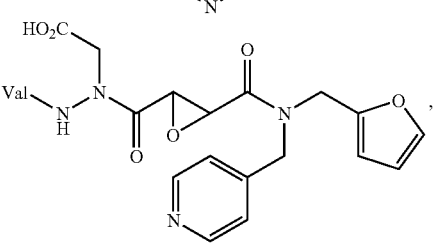

Cbz-Leu-Glu-Thr-AAsp-(S,S)-EP-COOCH₂Ph,
Cbz-Ile-Glu-Thr-AAsp-(S,S)-EP-COOCH₂Ph,
Cbz-Ile-Glu-Thr-AAsp-(R,R)-EP-COOCH₂Ph,
Cbz-Ile-Glu-Thr-AAsp-(R,R)-EP-CONGCH₂Ph.

EXEMPLARY METHODS OF PREPARATION

A. Preparation of the Epoxide Portion

A variety of epoxides can be synthesized by following the schemes shown below. Any aldehyde can be reacted with malonic acid to form the α,β-unsaturated acid, which can be further transformed into an ethyl ester. The double bond is epoxidized using t-butyl peroxide and t-butyl lithium, followed by the deblocking of the ethyl ester to yield the substituted epoxide. This epoxide can then be coupled to the respective substituted hydrazide to yield an aza-peptide epoxide using peptide coupling procedures.

The diethyl ester epoxysuccinate can also be deblocked to yield the diacid, which can be selectively coupled to different alcohols to yield a variety of epoxide monoesters. Hydrolysis of diethyl epoxysuccinate also yields the monoethyl ester, which can be coupled with a variety of monosubstituted and disubstituted amines to form amide derivatives of ethyl epoxysuccinate. The ethyl ester can then be hydrolyzed to the acid. These epoxides can then be coupled to substituted hydrazides to yield aza-peptide epoxides. These processes are illustrated below.

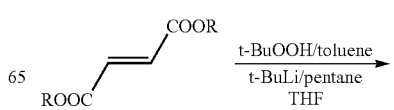

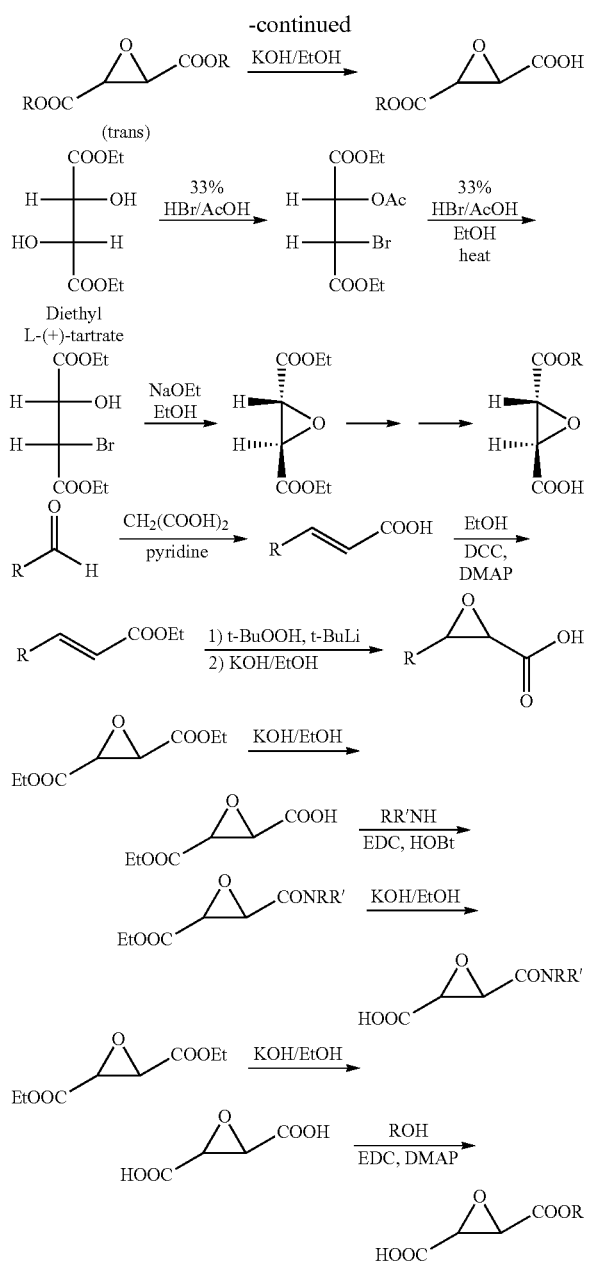

B. Preparation of the Peptide Portion

The peptide portion of the aza-peptide epoxide inhibitor can be prepared using standard peptide chemistry which is well described in publications such as *The Peptides, Analysis, Synthesis, Biology*, Vol. 1-9, published in 1979-1987 by Academic Press; Houben-Weyl Methoden der Organischen Chemie, Vol. 15, Parts 1 and 2, Synthese von Peptiden, published by Georg Thieme Verlag, Stuttgart in 1974; and Houben-Weyl Methods of Organic Chemistry, Vol. E22, Parts a, b, c, and d, *Synthesis of Peptides and Peptidomimetics* published by Georg Thieme Verlag, Stuttgart 2000-2003 (references incorporated herein by reference).

The $M_1$ group can be introduced using a number of different reaction schemes. First, it could be introduced directly on an amino acid as shown in the following scheme (top), or the $M_1$ group could be introduced by reaction with an amino acid ester, followed by removal of the ester group to give the same product (bottom).

H-AAOH→$M_1$-AAOH

H-AAOR'→$M_1$-AAOR'→$M_1$-AAOH

The techniques for introduction of the $M_1$ group are well documented in The Peptides, Houben-Weyel, and many other textbooks on organic synthesis. For example reaction with cyanate or p-nitrophenyl cyanate would introduce a carbamyl group ($M_1$=$NH_2CO$—). Reaction with $Me_2NCOCl$ would introduce the $Me_2NCO$— group. Reaction with p-nitrophenyl thiocarbamate would introduce a thio carbamyl group ($M_1$=$NH_2CS$—). Reaction with $NH_2SO_2Cl$ would introduce the $NH_2SO_2$— group. Reaction with $Me_2NSO_2Cl$ would introduce the $Me_2NSO_2$— group. Reaction with a substituted alkyl or aryl isocyanate would introduce the X—NH—CO— group where X is a substituted alkyl or aryl group. Reaction with a substituted alkyl or aryl isothiocyanate would introduce the X—NH—CS— group where X is a substituted alkyl or aryl group. Reaction with X—$SO_2$—Cl would introduce the X—$SO_2$— group. Reaction with a substituted alkyl or aryl acid chloride would introduce an acyl group (M=X—CO—). For example, reaction with MeO-CO—$CH_2CH_2$—CO—Cl would give the X—CO— group where X is a $C_2$ alkyl substituted with a $C_1$ alkyl-OCO— group. Reaction with a substituted alkyl or aryl thioacid chloride would introduce a thioacyl group (M=X—CS—). Reaction with a substituted alkyl or aryl sulfonyl chloride would introduce the X—$SO_2$— group. For example, reaction with dansyl chloride would give the X—$SO_2$— derivative where X was a naphthyl group mono substituted with a dimethylamino group. Reaction with a substituted alkyl or aryl chloroformate would introduce the X—O—CO— group. Reaction with a substituted alkyl or aryl chlorothioformate would introduce the X—O—CS—. There are many alternate reaction schemes which could be used to introduce all of the above $M_1$ groups to give either $M_1$-AA-OH or $M_1$-AA-OR'.

The $M_1$-AA-OH derivatives could then be used directly in the preparation of peptide hydrazides or could be converted into the dipeptides, tripeptides, and tetrapeptides $M_1$-AA-AA-OH, $M_1$-AA-AA-AA-OH, or $M_1$-AA-AA-AA-AA-OH which could then be converted to peptide hydrazides. The substituted peptides $M_1$-AA-AA-OH, $M_1$-AA-AA-AA-OH, or $M_1$-AA-AA-AA-AA-OH could also be prepared directly from H-AA-AA-OH, H-AA-AA-AA-OH, or H-AA-AA-AA-AA-OH using the reactions described above for introduction of the $M_1$ group. Alternatively, the $M_1$ group could be introduced by reaction with carboxyl blocked peptides to give $M_1$-AA-AA-OR', $M_1$-AA-AA-AA-OR', or $M_1$-AA-AA-AA-AA-OR', followed by the removal of the blocking group R'.

C. Peparation of Peptide Hydrazides

Usually, peptide hydrazides are synthesized by reaction of an amino acid or peptide ester with hydrazine or by direct coupling of an amino acid or peptide acid with hydrazine as shown in the following two figures. They can also be synthesized directly by reaction of an amino acid or peptide ester with hydrazine.

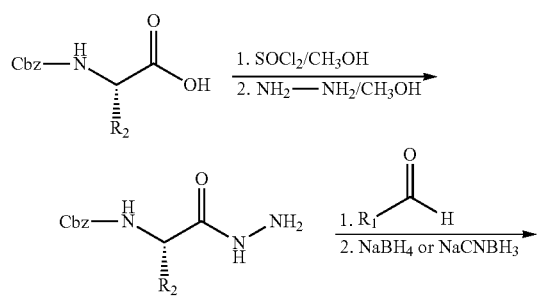

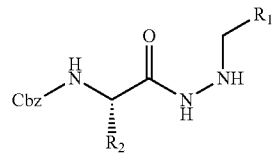

The side chain of the aza-amino acid residue can be introduced by reductive amination as shown specifically in the previous figure or by other methods known by those skilled in the art or by alkylation as shown in the following figure.

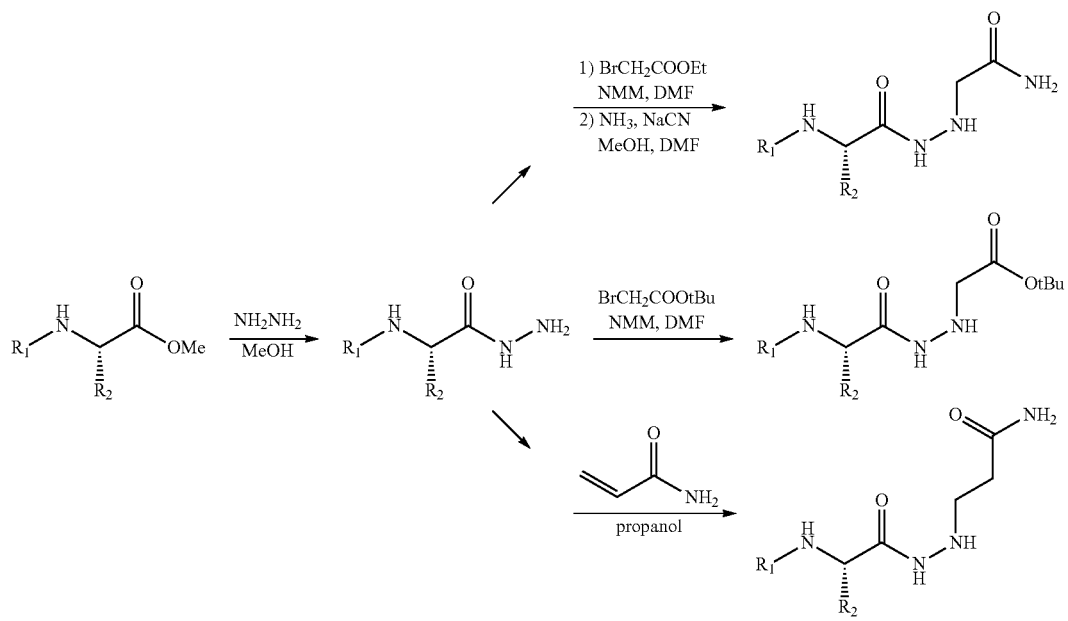

The precursors for basic side chain aza-peptide epoxides were prepared as shown in the following figure.

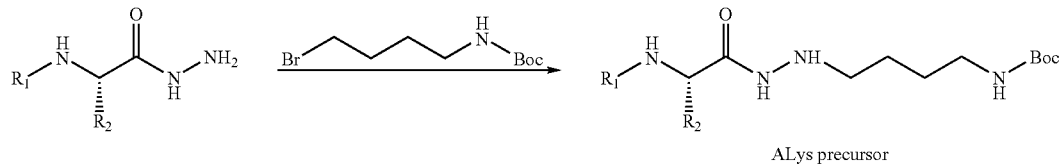

ALys precursor

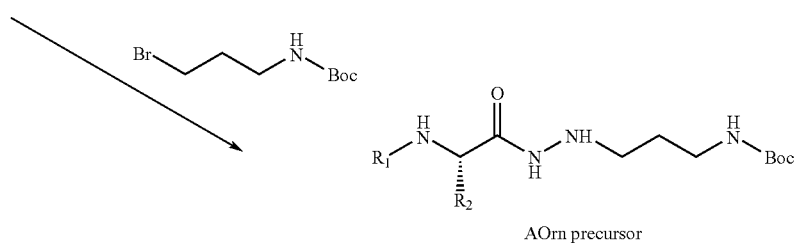

AOrn precursor

D. Preparation of the Aza-Peptide Epoxide

1. EDC/HOBt Coupling Method

The epoxide portion of the aza-peptide epoxide is coupled to the substituted hydrazide by reacting the epoxide portion, the substituted hydrazide, EDC, and HOBt in DMF to form the aza-peptide epoxide (see the following figure).

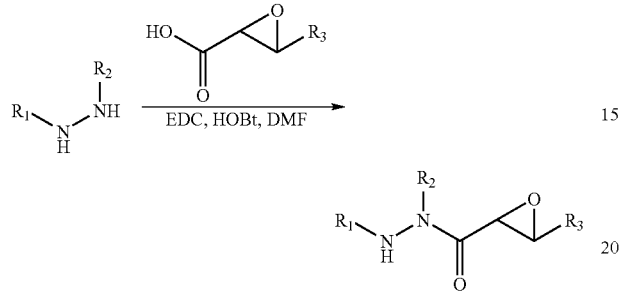

Methods for the protection and deprotection and replacement of an amino protecting group with another moiety are well known. Deprotection of other side chain protecting groups were carried out by standard methods.

2. The Mixed Anhydride Method

Another coupling method is the mixed anhydride method. In this method, the epoxide portion of the aza-peptide epoxide is coupled to the substituted hydrazide by reacting the epoxide portion (carboxylic acid) with NMM in DMF and IBCF followed by the substituted hydrazide to form the aza-peptide epoxide (see the following figure). Methods for the protection and deprotection of side chain protecting groups are well known.

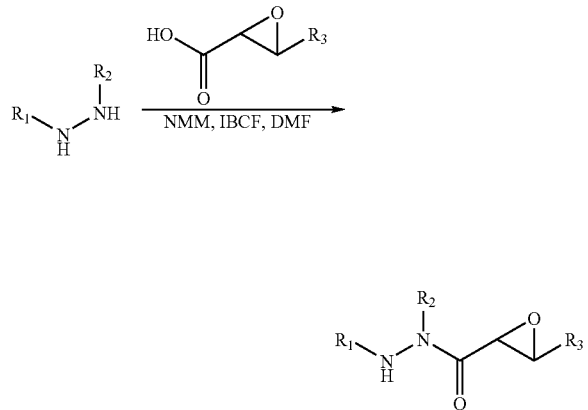

The following figure shows how these methods are used to build the AAsp and AAsn derivatives.

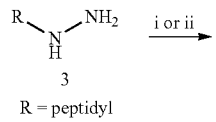

R = peptidyl

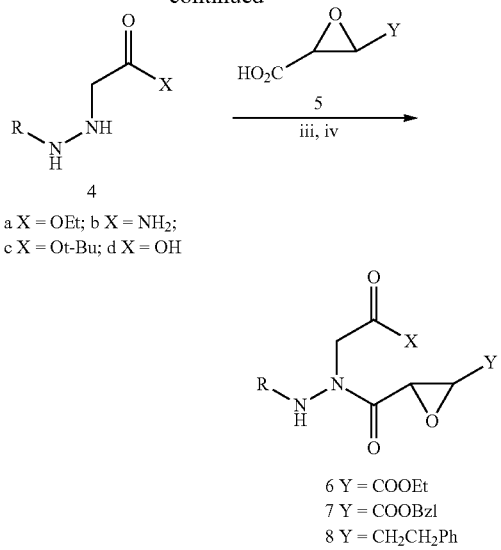

a X = OEt; b X = $NH_2$;
c X = Ot-Bu; d X = OH

6 Y = COOEt
7 Y = COOBzl
8 Y = $CH_2CH_2Ph$

Reagents: (i) $BrCH_2COOEt$, NMM, DMF; $NH_3$/MeOH, 0.1 eq NaCN, DMF. (ii) $BrCH_2COO$-tBu, NMM DMF. (iii) 3, EDC, HOBt, DMF or NMM, IBCF, DMF. (iv) TFA (can be used to deblock the t-Butyl Group in certain peptides where X=O-tBu).

Examples of the preceding methods are exhibited below (additional examples are described in U.S. patent application Ser. No. 10/603,054, which is incorporated herein by reference in its entirety):

E. Synthetic Procedures and Examples

1. Material and Methods. Mono and dipeptidyl methyl esters were purchased from Bachem Bioscience Inc., King of Prussia, Pa. Tripeptides were synthesized using standard coupling procedures such as the mixed anhydride method. The $^1$H NMR spectra were obtained using a Varian Mercury 300 MHz spectrometer. Electrospray ionization (ESI), fast-atom-bombardment (FAB) and high-resolution mass spectrometry were performed using Micromass Quattro LC and VG Analytical 70-SE instruments. Elemental analysis was performed by Atlantic Microlab Inc., Norcross, Ga.

2. Preparation of Peptidyl Hydrazides (3). Anhydrous hydrazine (10 eq) was added to a solution of the peptidyl methyl ester (1 eq) in MeOH at room temperature, and the resulting mixture was then stirred for 16 hours. As with most hydrazides, excess hydrazine and solvent were removed by evaporation. The resulting residue was washed with ethanol and ether to give the desired peptidyl hydrazide (3) as a white solid. MS and $^1$H NMR ($CDCl_3$ or DMSO-$d_6$) were consistent with the proposed structures.

Cbz-Asp(O-tBu)-Glu(O-tBu)-Val-NH—$NH_2$ was purified by chromatography on a silica gel column using 1:9 MeOH:$CH_2Cl_2$ as the eluent; white solid, yield 56%.

Cbz-Glu(O-tBu)-Val-NH—$NH_2$ was purified by chromatography on a silica gel column using 1:9 MeOH:$CH_2Cl_2$ as the eluent; white solid, yield 47-53%.

Cbz-Ile-Glu(O-tBu)-Thr-NH—$NH_2$, white solid, yield 91%.

3. Preparation of Peptidyl-$AA_2$-NH—NH—$CH_2$COO-tBu (4c). Neat t-butyl bromoacetate (1 eq) was added to a stirred solution of the peptide hydrazide (3) and NMM (1 eq) in DMF pre-cooled at −10° C. The resulting solution was stirred for 30 min at −10° C., after which the mixture was allowed to react at room temperature for 20 hours. The DMF was removed by evaporation, and the resulting residue was washed with water, filtered, and dried in vacuo. Purification on a silica gel column using the appropriate solvent gave 4c (yields=48-65%). MS and $^1$H NMR (DMSO-d$_6$ or CDCl$_3$) were consistent with the proposed structure.

Cbz-Asp(O-tBu)-Glu(O-tBu)-Val-NH—NH—CH$_2$COO-tBu was purified by column chromatography on silica gel using 2:18:5 MeOH:CH$_2$Cl$_2$:EtOAc as the eluent; white solid, yield 65%. MS (ESI) m/z 736.6 [(M+1)$^+$]. $^1$H NMR (DMSO-d$_6$): 0.90 (d, 6H, Val), 1.49 (s, 27H, tBu), 1.85-2.20 (m, 3H, Val and Glu), 2.21 (m, 2H, Glu), 2.40-2.70 (m, 2H, Asp CH$_2$), 3.30 and 3.38 (m, 3H, NHCH$_2$ and NHCH$_2$), 4.05-4.30 (m, 3H, α-H), 5.05 (m, 2H, Cbz), 7.20-7.40 (m, 5H, Ph), 7.60-7.95 (m, 3H, NH), 9.2 (m, 1H, NH).

Cbz-Glu(O-tBu)-Val-NH—NH—CH$_2$COO-tBu was purified by column chromatography on silica gel using 2:18:5 MeOH:CH$_2$Cl$_2$:EtOAc as the eluent; white solid, yield 78%. MS (ESI) m/z 565.3 [(M+1)$^+$]. $^1$H NMR (CDCl$_3$): 0.95 (t, 6H, Val), 1.49 (s, 18H, tBu), 1.85-2.20 (m, 3H, Val and Glu), 2.21 (m, 2H, Glu), 3.45-3.70 (m, 3H, NHCH$_2$ and NHCH$_2$), 4.25-4.30 (m, 2H, α-H), 5.05 (m, 2H, Cbz), 5.85 (d, 1H, NH), 7.05 (d, 1H, NH), 7.20-7.40 (m, 5H, Ph), 8.00 (m, 1H, NH).

Cbz-Leu-Glu(O-tBu)-Thr-NH—NH—CH$_2$COO-tBu was purified by column chromatography on silica gel using 1:9 MeOH:CH$_2$Cl$_2$ as the eluent; white solid, yield 34%. MS (ESI) m/z 680 [(M+1)$^+$]. $^1$H NMR (DMSO-d$_6$): 0.7-0.9 (t, 6H, Leu CH$_3$), 1.0 (d, 3H, Thr CH$_3$), 1-1.3 (m, 2H, Leu CH$_2$), 1.3-1.5 (m, 18H, tBu), 1.5-1.8 (m, 2H, Leu CH and Glu CH$_2$), 1.8-1.95 (m, 1H, Glu CH$_2$), 2.1-2.3 (m, 2H, Glu CH$_2$), 3.4 (d, 2H, NCH$_2$), 3.9 (m, 1H, α-H), 4.1 (m, 1H, α-H and Thr CH—OH), 4.3 (m, 1H, α-H), 4.9 (d, 1H, NH), 5.03 (m, 2H, Cbz), 7.3-7.4 (m, 5H, phenyl), 7.5 (d, 1H, NH), 7.6 (d, 1H, NH), 8.05 (d, 1H, NH), 9.2 (d, 1H, NH).

Cbz-Ile-Glu(O-tBu)-Thr-NH—NH—CH$_2$COO-tBu was purified by column chromatography on silica gel using 1:9 MeOH:CH$_2$Cl$_2$ as the eluent; white solid, yield 26%. MS (ESI) m/z 680 [(M+1)$^+$]. $^1$H NMR (DMSO-d$_6$): 0.7-0.9 (t, 6H, Ile CH$_3$), 0.9-1.0 (d, 3H, Thr CH$_3$), 1-1.2 (m, 2H, Ile CH$_2$), 1.3-1.5 (s, 18H, tBu), 1.6-1.8 (m, 2H, Ile CH and Glu CH$_2$), 1.8-1.9 (m, 1H, Glu CH$_2$), 2.1-2.3 (m, 2H, Glu CH$_2$), 3.4 (d, 2H, NCH$_2$), 3.9 (m, 2H, α-H), 4.1 (m, 1H, α-H), 4.35 (m, 1H, Thr CH—OH), 4.8 (d, 1H, NH), 5.03 (s, 2H, Cbz), 5.05 (d, 1H, NH), 7.3-7.4 (m, 5H, phenyl), 7.7 (d, 1H, NH), 8.05 (d, 1H, NH), 9.2 (s, 1H, NH).

4. Preparation of (2S,3S) and (2R,3R)-Oxirane-2,3-dicarboxylic Acid Monoethyl Esters (or Monoethyl Epoxysuccinates, 5, Y=COOEt). Enantiomerically pure diethyl epoxysuccinate esters (2S,3S) and (2R,3R) were synthesized from diethyl D-(−) and L-(+)-tartrate, respectively, following the general method developed by Mori and Iwasawa. This procedure involved three steps including bromination, elimination, and cyclizations. The selective hydrolysis of one ester to yield monoethyl epoxysuccinates was performed by a method similar to that described previously by Rich and Schaschke.

5. Preparation of trans-Oxirane-2,3-dicarboxylic Acid Diethyl Ester (or Diethyl Epoxysuccinate). The trans-oxirane-2,3-dicarboxylic acid diethyl ester was synthesized using a general procedure for the stereocontrolled epoxidation of α,β-unsaturated carbonyl compounds, which was similar to the method previously described by Meth-Cohn. An anhydrous solution of t-butyl hydroperoxide in toluene (3.3 M solution, 46 mL, 1.5 eq), was added to freshly distilled THF (240 mL) at −78° C. under argon. This was followed by the addition of a solution of butyl lithium in pentane (1.7 M solution, 65 mL, 1.1 eq). The mixture was stirred at −78° C. for 5 min, then a solution of diethyl fumarate (17.2 g, 0.1 M, 1 eq) in THF (50 mL) was added. The reaction mixture was stirred at room temperature for 2 hours (monitored by TLC). Sodium sulfite (10 g) was added and the mixture was stirred for 20 min. The mixture was concentrated to ca. 100 mL, diluted with ether (100 mL), filtered through yiatomaceous earth (celite), and evaporated. To the residue was added 1 M HCl (100 mL). The product trans-oxirane-2,3-dicarboxylic acid diethyl ester was extracted with EtOAc (3×100 mL), and the organic layer was washed with saturated NaCl (3×50 mL), dried over MgSO$_4$, and the solvent evaporated. Chromatography on a silica gel column with 2:3 EtOAc:hexane afforded the product trans-oxirane-2,3-dicarboxylic acid diethyl ester (yield=52%).

6. Preparation of trans-Oxirane-2,3-dicarboxylic Acid. A solution of 1 M NaOH (98 mL, 1.9 eq) was added to trans-oxirane-2,3-dicarboxylic acid diethyl ester (9.8 g, 52 mM) in MeOH (30 mL) at 0° C. The resulting solution was stirred for 1 h at 0° C., then for 30 min at room temperature, after which the solution was acidified to pH 3. Water and MeOH were evaporated. The residue was treated with EtOH (150 mL), filtered and the solvent evaporated, to give trans-oxirane-2,3-dicarboxylic acid as a colorless semisolid (yield=97%).

7. Preparation of trans-Oxirane-2,3-dicarboxylic Acid Monobenzyl Ester (5, Y=COOBzl). The reagent EDC (2.32 g, 11 mM) was added to a stirred solution of trans-oxirane-2,3-dicarboxylic acid (1.32 g, 10 mM), benzyl alcohol (1.08 g, 10 mM), and DMAP (122 mg, 1 mM) in DMF (100 mL), which has been cooled to 0° C. The resulting solution was stirred for 15 h at room temperature. After removal of DMF, the residue was purified by chromatography on two successive columns using 1:9 MeOH:CH$_2$Cl$_2$ as the eluent, followed by column chromatography using 1:4 MeOH:CH$_2$Cl$_2$ as the eluent to give 5 (Y=COOBzl), as a dark yellow oil (yield=66%). $^1$H NMR: 3.60 (d, 1H, epoxy), 3.75 (d, 1H, epoxy), 5.18 (s, 2H, PhCH$_2$O), 7.38 (d, 5H, Ph).

8. General Procedure for Coupling Oxirane Dicarboxylic Acid Monoethyl Esters to Amines. The procedure used to synthesize amide derivatives of epoxysuccinate monoethyl esters was similar to that of Therrien et al (Biochemistry 2001 40 p 2702). To a solution of epoxysuccinate monoethyl ester (1 g, 6.25 mM), amine/amino acid (1.2 eq) and HOBt (1 eq) in CHCl$_3$ (30 mL) at 0° C. was added EDC (1.1 eq) slowly in 5 portions. The reaction was stirred for one hour at 0° C. and then subsequently at room temperature for 16 hours. The solvent was evaporated and the residue was partitioned between EtOAc (50 mL) and dH$_2$O (5 mL). The organic layer was washed with 0.5 M HCl (2×10 mL), sat NaHCO$_3$ (2×50 mL), dried over MgSO$_4$ and concentrated. In general, the oxirane-2,3-dicarboxylic acid monoamides were obtained in 43-74% yield. The crude product was purified by chromatography on a silica gel column using 1:1 EtOAc:hexanes as the eluent to yield a white solid. Hydrolysis of the ester by KOH (1.2 eq) gave the desired amides (yields=65-95%).

9. (2S,3S)-Oxirane-2,3-dicarboxylic Acid Monobenzyl Ester (HOOC-EP-COOCH$_2$Ph). $^1$H NMR (CDCl$_3$): 3.70 (d, 2H, epoxy), 5.22 (d, 2H, CH$_2$Ph), 7.35 (m, 5H, Ph).

10. (2R,3R)-Oxirane-2,3-dicarboxylic Acid Monobenzyl Ester (HOOC-EP-COOCH$_2$Ph). $^1$H NMR (CDCl$_3$): 3.65 (d, 2H, epoxy), 5.17 (d, 2H, CH$_2$Ph), 7.32 (m, 5H, Ph).

Utility of the Compounds of the Present Disclosure

Peptide aza-peptide epoxides are irreversible inhibitors for cysteine proteases. Peptide aza-peptide epoxides containing hydrophobic aza-amino acid residues in the P1 and/or P2 site have been found to be excellent inhibitors of cysteine proteases including cathepsin B and papain. We show that peptide aza-peptide epoxides containing aza-amino acid residues with anionic side chains in the P1 site are excellent inhibitors of caspases. Legumain is inhibited by aza-peptide epoxides with a P1 aza-asparagine residue. Clostripain and gingipain are inhibited by aza-peptide epoxides with P1 basic side chains. Peptide aza-peptide epoxides containing aza-amino acid residues with hydrophobic side chains at the P2 site have also been found to be excellent inhibitors of several cysteine proteases including papain, cathepsin B, calpain I, and calpain II. These structures may be used in vivo to treat diseases such as cancer and neurodegenerative diseases which result from the uncontrolled proteolysis by cathepsin B, calpain, caspases, and related cysteine proteases. These inhibitors may be used in vitro to prevent proteolysis which occurs in the process of production, isolation, purification, storage, or transport of peptides and proteins. These inhibitors may be useful as therapeutic agents for treatment of neurodegeneration, viral infections, muscular dystrophy, myocardial tissue damage, tumor metastasis, and bone resorption.

1. Enzyme Assays.

Caspase-1. The preparation of the autolytically stable caspase-1 variant used in these studies has been described previously. Briefly, the variant contains a mutation (D381E) which renders it resistant to autolytic inactivation, but has no detectable affect on enzyme activity as compared to the naturally occurring enzyme. The enzyme variant was expressed in *E. coli*, purified first by immobilized metal chromatography via the N-terminal N-His tag, treated with excess oxidized glutathione to stabilize the reactive thiolate, and then re-purified by size-exclusion chromatography.

Inhibition data was measured using the progress curve assay method. Serial dilutions of each compound were prepared using an initial 8-fold dilution of a DMSO stock into HGE (100 mM HEPES, 20% glycerol v/v, 0.5 mM EDTA), followed by seven serial two-fold dilutions into HGE and 12.5% DMSO, thus maintaining constant DMSO through the dilution series. Ten µL of diluted stocks or of vehicle (HGE and 12.5% DMSO) were placed in triplicate onto a 96-well microtiter plate, allowing several compounds to be tested on each plate. The plate was covered to minimize evaporation, and the plate was pre-warmed to 30° C. for 20 minutes. Enzyme was diluted into 10.0 mL of assay buffer (HGE, 5 mM DTT, plus 15 µM Ac-YVAD-AMC, 2 nM approximate final enzyme concentration), and this activated reaction mixture was added to the plate at 90 µL/well. Progress of substrate hydrolysis was monitored for 900 s in a LabSystems (Needham, Mass.) Fluoroskan Ascent fluorescent plate-reader using 385 and 460 nm excitation and emission filters, respectively, and a photomultiplier gain setting of 10. Triplicate curves were averaged and fit by nonlinear regression to the equation for irreversible inactivation shown below.

$$F(t) = F_0 + \frac{V_i(1 - e^{-k_{obs}t})}{k_{obs}}$$

where $F_0$ was routinely fixed to zero, since fluorescence values were always adjusted to an origin of 0. The second order rate constant $k_{on}$ (M$^{-1}$s$^{-1}$) was obtained from the slopes by linear regression, and errors represent the standard deviation of the regression slope.

Caspase-3, -6, and -8. Caspase-3, -6 and -8 were expressed in *E. coli* and purified according to methods previously described by Stennicke and Salvesen. Assays using the fluorogenic substrate Z-DEVD-AFC ($\lambda_{ex}$=400 nm, $\lambda_{em}$=505 nm) were carried out on a Molecular Devices fNax fluorescence microplate reader. Inhibition rates and equilibria were determined by the progress curve method. The standard 100 µL reaction was started by adding enzyme to a mixture of substrate (final concentration of Z-DEVD-AFC 100 µM) and various amounts of inhibitor in buffer (50 mM Hepes, 100 mM NaCl, 0.1% (w/v) CHAPS, sucrose 10% (w/v), and 10 mM DTT, at pH 7.4). The caspases were pre-activated for 10 min at 37° C. in the presence of 10 mM DTT.

2. Structure-Activity Relationships

Table I shows the inhibition rate constants ($k_{obs}$/[I]) for the inhibition of papain, cathepsin B, and calpain by aza-peptide epoxides. The inhibition constants are second-order rate constants and the inhibitors with the higher numbers are more potent.

TABLE I

Inhibition of Papain, Cathepsin B, and Calpain by Aza-peptide Epoxides.

| | $k_{obs}$/[I] (M$^{-1}$ s$^{-1}$) | | |
|---|---|---|---|
| Inhibitor | papain | cathepsin B | calpain |
| Boc-Nva-AHph-trans-EP-COOEt | 1.4 | 2.7 | |
| Boc-Nle-AHph-trans-EP-COOEt | 1.6 | 1.3 | |
| Boc-Abu-AHph-trans-EP-CH$_2$CH$_2$Ph | 0.2 | NI | |
| Boc-Nle-AHph-trans-EP-CH$_2$CH$_2$Ph | 0.5 | NI | |
| Cbz-APhe-trans-EP-COOEt | 8.5 | 1.8 | |
| Cbz-APhe-trans-EP-CH$_2$CH$_2$Ph | 0.92 | | |
| Cbz-ALeu-trans-EP-COOEt | 16.1 | 4.43 | 1.75 |
| Cbz-AHph-trans-EP-COOEt | 18.8 | 8.91 | 2.44 |
| Ac-AHph-trans-EP-COOEt | 26.88 | 40.62 | 1.29 |
| Cbz-Leu-ALeu-(2S,3S)-EP-COOEt | 10.53 | 1.8 | 8.58 |
| Cbz-Leu-ALeu-(2R,3R)-EP-COOEt | 6.70 | NI | 1.45 |
| Cbz-Leu-ALeu-trans-EP-COOEt | 6.37 | 23.32 | 3.09 |
| Cbz-Leu-ALeu-cis-EP-COOEt | 0.38 | 6.27 | 1.88 |
| Cbz-Phe-ALeu-trans-EP-COOEt | 0.91 | 3.61 | |
| Cbz-Phe-ALeu-trans-EP-CH$_2$CH$_2$Ph | 0.7 | NI | |
| Cbz-Phe-APhe-trans-EP-CH$_2$CH$_2$Ph | 0.5 | NI | |
| Cbz-Leu-AAbu-trans-EP-COOEt | 4.94 | | 1.98 |
| Cbz-Leu-AAbu-trans-EP-COOH | 1.47 | NI | 0.57 |
| Cbz-Leu-AHph-cis-EP-COOEt | 1.03 | NI | 1.09 |
| Cbz-Leu-AHph-(2S,3S)-EP-COOEt | 5.68 | 0.67 | 2.28 |
| Cbz-Leu-AHph-(2R,3R)-EP-COOEt | 2.16 | NI | 2.12 |
| Cbz-Leu-AHph-(2S,3S)-EP-COOH | | | 2.12 |
| Boc-Np2-ALeu-trans-EP-COOEt | 3.9 | 0.39 | |
| Suc-Np2-ALeu-trans-EP-COOEt | 1.39 | 0.8 | |
| Ac-Leu-AHph-trans-EP-COOEt | 1.9 | 0.59 | 0.84 |
| Ac-Leu-ALeu-trans-EP-COOEt | 2.09 | 8.0 | 1.48 |
| Cbz-Leu-Leu-ALeu-trans-EP-COOEt | 34.77 | NI | 2.65 |
| Cbz-Leu-Leu-ALeu-(2S,3S)-EP-COOEt | 10.53 | 0.98 | 2.48 |
| Cbz-Leu-Leu-ALeu-(2R,3R)-EP-COOEt | 20.58 | NI | NI |
| Cbz-Leu-Leu-ALeu-(2S,3S)-EP-COOH | 6.93 | 7.02 | 0.82 |
| Cbz-Leu-Phe-AGln-trans-EP-COOEt | 0.9 | 1.3 | |
| Cbz-Leu-Phe-AGln-(2S,3S)-EP-COOEt | | 4.73 | |
| Cbz-Leu-Phe-AGln-(2R,3R)-EP-COOEt | | NI | |
| Cbz-Ala-Ala-AAsn-trans-EP-COOEt | 0.9 | 1.27 | |
| Cbz-Ala-Ala-AAsn-(2R,3R)-EP-COOEt | 3 | NI | |
| Cbz-Ala-Ala-AAsn-(2S,3S)-EP-COOEt | 4 | 6 | |
| Cbz-Ala-Ala-AAsn-cis-EP-COOEt | NI | NI | |
| Cbz-Ala-Ala-AAsn-trans-EP-COOCH$_2$Ph | | 1.09 | |
| Cbz-Ala-Ala-NHN(CH$_2$COOEt)-trans-EP-COOEt | 8.17 | 2.53 | |

TABLE I-continued

Inhibition of Papain, Cathepsin B, and Calpain by Aza-peptide Epoxides.

| Inhibitor | $k_{obs}/[I]$ (M$^{-1}$ s$^{-1}$) | | |
|---|---|---|---|
| | papain | cathepsin B | calpain |
| PhPr-Val-Ala-AAsp-trans-EP-COOCH$_2$Ph | <10 | <10 | |
| PhPr-Val-Ala-AAsp-trans-EP-CH$_2$CH$_2$Ph | NI | NI | |
| PhPr-Val-Ala-AAsp-(2S,3S)-EP-COOCH$_2$Ph | | | 0.81 |
| PhPr-Val-Ala-AAsp-(2R,3R)-EP-COOCH$_2$Ph | | | NI |
| Cbz-Asp-Glu-Val-AAsp-(2S,3S)-EP-COOEt | NI | NI | |
| Cbz-Asp-Glu-Val-AAsp-(2R,3R)-EP-COOEt | NI | NI | |
| Cbz-Leu-Glu-Thr-AAsp-(2S,3S)-EP-COOEt | 0.47 | NI | |
| Cbz-Leu-Glu-Thr-AAsp-(2R,3R)-EP-COOEt | 0.24 | NI | |
| Cbz-Ile-Glu-Thr-AAsp-(2S,3S)-EP-COOEt | | NI | |

NI = no inhibition,
EP = epoxide,
PhPr = PhCH$_2$CH$_2$CO—.

The aza-peptide epoxide inhibitors are quite specific and do not react with serine proteases. Table II shows tests of a number of aza-peptide epoxide inhibitors with chymotrypsin. None of the aza-peptide epoxide derivatives inhibited this serine protease.

TABLE II

Inactivity of Aza-peptide Epoxides Toward Chymotrypsin.

| Inhibitor | $k_{obs}/[I]$ (M$^{-1}$ s$^{-1}$) chymotrypsin |
|---|---|
| Cbz-Asp-Glu-Val-AAsp-(2S,3S)-EP-COOEt | NI |
| Cbz-Asp-Glu-Val-AAsp-(2R,3R)-EP-COOEt | NI |
| Cbz-Leu-Glu-Thr-AAsp-(2S,3S)-EP-COOEt | NI |
| Cbz-Leu-Glu-Thr-AAsp-(2R,3R)-EP-COOEt | NI |
| PhPr-Val-Ala-AAsp-trans-EP-COOCH$_2$Ph | NI |
| PhPr-Val-Ala-AAsp-trans-EP-CH$_2$CH$_2$Ph | NI |
| Cbz-Ala-Ala-AAsn-trans-EP-COOEt | NI |
| Cbz-Ala-Ala-AAsn-(2R,3R)-EP-COOEt | NI |
| Cbz-Ala-Ala-AAsn-(2S,3S)-EP-COOEt | NI |
| Cbz-Ala-Ala-AAsn-cis-EP-COOEt | NI |

NI = no inhibition,
EP = epoxide.

Table III shows the rate of inhibition of dipeptidyl peptidase I (DPPI, cathepsin C) by aza-peptide epoxides.

TABLE III

Inhibition of DPPI by Aza-peptide Epoxides.

| Inhibitor | $k_{obs}/[I]$ (M$^{-1}$ s$^{-1}$) DPPI |
|---|---|
| Boc-Nva-AHph-trans-EP-COOEt | 0.5 |
| Boc-Nle-AHph-trans-EP-COOEt | 0.7 |
| Nva-AHph-trans-EP-COOEt•TFA | 3.2 |
| Nva-AHph-trans-EP-CH$_2$CH$_2$Ph•TFA | 0.1 |
| Nle-AHph-trans-EP-COOEt•TFA | 8.2 |

EP = epoxide.

Tables IV and V show the rates of inhibition of caspases by aza-peptide epoxides. Several of the inhibitors are highly effective with inhibition rate constants in the range of 300,000 to over 1 million M$^{-1}$S$^{-1}$. They also exhibit a high degree of selectivity for the target enzyme. They don't inhibit aspartyl protease, serine proteases such as granzyme B, which is also specific for a P1 Asp.

TABLE IV

Inhibition of Caspases by Aza-peptide Epoxides.

| | inhibitor | EP | $k_2$ (M$^{-1}$s$^{-1}$) | | | |
|---|---|---|---|---|---|---|
| | | | caspase-1 | caspase-3 | caspase-6 | caspase-8 |
| 22c | Cbz-Val-AAsp-EP-COOEt | S,S | NA | 3650 ± 570 | 350 ± 77 | 1260 ± 350 |
| 22n | Cbz-Val-AAsp-EP-COOH | S,S | NA | 1110 ± 340 | 90 ± 18 | 370 ± 80 |
| 22a | Cbz-Val-AAsp-EP-CH$_2$CH$_2$Ph | trans | NA | 310 ± 5 | 44 ± 9 | 180 ± 1 |
| 22b | Cbz-Val-AAsp-EP-Ph-4-Cl | trans | NA | 145 ± 18 | NI | NI |
| 23a | PhPr-Val-Ala-AAsp-EP-CH$_2$CH$_2$Ph | trans | 300 ± 144 | NA | NA | NA |
| 23c | PhPr-Val-Ala-AAsp-EP-COOEt | S,S | 32200 ± 14560 | 1040 ± 80 | 75 ± 15 | 1570 ± 235 |
| | | R,R | 6290 ± 1524 | NI | NI | NI |
| 23d | PhPr-Val-Ala-AAsp-EP-COOCH$_2$Ph | trans | 18070 ± 2625 | 680 ± 140 | NA | NA |
| | | S,S | 52140 ± 5295 | 1470 ± 40 | 165 ± 30 | 1560 ± 110 |
| | | R,R | 1860 ± 302 | NI | 15 | 185 |
| 23e | PhPr-Val-Ala-AAsp-EP-COOCH$_2$CH$_2$Ph | S,S | 56640 ± 9322 | 2110 ± 50 | 240 ± 14 | 3775 ± 630 |
| 23f | PhPr-Val-Ala-AAsp-EP-CONHCH$_2$CH$_3$ | S,S | | 1910 ± 370 | 142 ± 14 | 6050 ± 865 |
| 23g | PhPr-Val-Ala-AAsp-EP-CONHCH$_2$Ph | S,S | 65900 ± 9153 | 1610 ± 5 | 155 ± 3 | 9360 ± 1570 |
| | | R,R | 1630 ± 522 | NI | NI | NI |
| 23h | PhPr-Val-Ala-AAsp-EP-CONHCH$_2$CH$_2$Ph | S,S | 17150 ± 2254 | 1110 ± 100 | 130 ± 10 | 10050 ± 1890 |
| | | R,R | 950 ± 51 | NI | NI | NI |
| 23i | PhPr-Val-Ala-AAsp-EP-CONHCH$_2$CH(OH)Ph | S,S | 12260 ± 19 | 510 ± 100 | 63 ± 6 | 4090 ± 630 |
| | | R,R | 400 ± 19 | NI | NI | NI |

TABLE IV-continued

Inhibition of Caspases by Aza-peptide Epoxides.

| | inhibitor | EP | caspase-1 | caspase-3 | caspase-6 | caspase-8 |
|---|---|---|---|---|---|---|
| | | | \multicolumn{4}{c}{$k_2$ (M$^{-1}$s$^{-1}$)} |
| 23j | PhPr-Val-Ala-AAsp-EP-CO-Ala-NHCH$_2$Ph | S,S | 13400 | 260 ± 25 | 25 ± 5 | 140 ± 60 |
| | | R,R | 268 ± 75 | NI | NI | NI |
| 23k | PhPr-Val-Ala-AAsp-EP-CO-Leu-NH$_2$ | S,S | 26090 ± 2562 | 420 ± 6 | 71 ± 14 | 315 ± 45 |
| 23l | PhPr-Val-Ala-AAsp-EP-CO-Phe-NH$_2$ | S,S | 32740 ± 9937 | 625 ± 160 | 65 ± 1 | 390 ± 126 |
| | | R,R | 330 | NI | NI | NI |
| 23m | PhPr-Val-Ala-AAsp-EP-CO-Tyr-NH$_2$ | S,S | 3245 ± 2330 | 87 ± 4 | 11 | 125 |
| 24c | Cbz-Glu-Val-AAsp-EP-COOEt | S,S | 58500 | 50500 ± 2075 | 4185 | 195360 ± 24300 |
| 24l | Cbz-Glu-Val-AAsp-EP-CO-Phe-NH$_2$ | R,R | 1040 ± 455 | 470 ± 77 | 25 ± 5 | NA |
| 24h | Cbz-Glu-Val-AAsp-EP-CONHCH$_2$CH$_2$Ph | S,S | 41070 ± 440 | 27330 ± 5430 | 3135 ± 275 | 72750 ± 15000 |
| 25c | Cbz-Asp-Glu-Val-AAsp-EP-COOEt | S,S | 11840 ± 1214 | 1074440 ± 154710 | 5440 ± 140 | 95480 ± 13000 |
| | | R,R | 4320 ± 830 | 464420 ± 186300 | 475 | 785 ± 125 |
| 25l | Cbz-Asp-Glu-Val-AAsp-EP-CO-Phe-NH$_2$ | S,S | 9250 ± 2835 | 722180 ± 340860 | 6145 ± 535 | 29570 ± 4700 |
| 25g | Cbz-Asp-Glu-Val-AAsp-EP-CONHCH$_2$Ph | S,S | 25420 ± 4013 | 1097820 ± 94860 | 6000 ± 390 | 84390 ± 21600 |
| 25d | Cbz-Asp-Glu-Val-AAsp-EP-COOCH$_2$Ph | S,S | 54690 ± 15913 | 1915200 ± 209200 | 12700 ± 2075 | 188130 ± 52000 |
| 26c | Cbz-Leu-Glu-Thr-AAsp-EP-COOEt | S,S | 25730 | 3210 ± 315 | 8620 | 61190 ± 6000 |
| | | R,R | 19570 | 3250 ± 160 | 4390 | 34760 ± 6600 |
| 26d | Cbz-Leu-Glu-Thr-AAsp-EP-COOCH$_2$Ph | S,S | 43500 ± 2150 | 3520 ± 600 | 10285 ± 690 | 72750 ± 18000 |
| 26h | Cbz-Leu-Glu-Thr-AAsp-EP-CONHCH$_2$CH$_2$Ph | S,S | NA | 2550 ± 25 | 10040 ± 690 | 53275 ± 2220 |
| 26j | Cbz-Leu-Glu-Thr-AAsp-EP-CO-Ala-NHCH$_2$Ph | S,S | NA | 1280 ± 77 | 6660 ± 2200 | 44760 ± 2850 |
| 27c | Cbz-Ile-Glu-Thr-AAsp-EP-COOEt | S,S | 12372 | 4080 ± 360 | 45770 ± 4190 | 52800 ± 11000 |
| | | R,R | 13260 ± 3684 | 2630 ± 365 | 34050 ± 1135 | 8800 ± 2750 |
| 27d | Cbz-Ile-Glu-Thr-AAsp-EP-COOCH$_2$Ph | S,S | 45788 | 9545 ± 960 | 86230 ± 6640 | 58510 ± 4950 |
| | | R,R | 13000 ± 980 | 3115 ± 125 | 45400 ± 1580 | 4560 ± 470 |
| 27g | Cbz-Ile-Glu-Thr-AAsp-EP-CONHCH$_2$Ph | R,R | 18140 ± 4085 | 6475 ± 240 | 60150 ± 2000 | 6525 ± 1100 |
| 27j | Cbz-Ile-Glu-Thr-AAsp-EP-CO-Ala-NHCH$_2$Ph | S,S | NA | 3050 | 38250 ± 2930 | 56055 ± 11975 |

PhPr = Ph—CH$_2$—CH$_2$—CO—,
NI = no inhibition,
EP = epoxide,
AAsp = aza-Asp,
Cbz = Ph—CH$_2$—CO—.

TABLE V

Inhibition of Caspases by Aza-peptide Epoxides with Disubstituted Amides.

| | inhibitor | EP | caspase-1 | caspase-3 | caspase-6 | caspase-8 |
|---|---|---|---|---|---|---|
| | | | \multicolumn{4}{c}{$k_2$ (M$^{-1}$s$^{-1}$)} |
| 10-129 | PhPr-Val-Ala-AAsp-EP-CON(CH$_2$CH$_2$CH$_2$CH$_3$)$_2$ | S,S | 26150 ± 5460 | 520 ± 10 | 53 ± 9 | 650 ± 160 |
| 10-127 | PhPr-Val-Ala-AAsp-EP-CON(CH$_2$Ph)$_2$ | S,S | 101140 ± 9547 | 830 ± 40 | 145 ± 1 | 1000 ± 125 |
| 11-4 | Cbz-Leu-Glu-Thr-AAsp-EP-CON(CH$_2$Ph)$_2$ | S,S | NA | 2750 ± 205 | 13840 ± 270 | 60810 ± 685 |
| 11-11 | Cbz-Ile-Glu-Thr-AAsp-EP-CON(CH$_2$Ph)$_2$ | S,S | NA | 3550 | 32000 ± 1680 | 46780 |
| 11-16 | Cbz-Leu-Glu-Thr-AAsp-EP-CON(CH$_3$)CH$_2$Ph | S,S | NA | 2640 ± 100 | 9680 ± 875 | 61950 ± 6680 |
| 11-17 | PhPr-Val-Ala-AAsp-EP-CON(CH$_3$)CH$_2$Ph | S,S | NA | 1950 ± 150 | 136 | 3310 ± 650 |
| 11-18 | Cbz-Ile-Glu-Thr-AAsp-EP-CON(CH$_3$)CH$_2$Ph | S,S | NA | 4780 | 47730 ± 420 | 56860 ± 6275 |

TABLE VI

Inhibition of Legumain by Aza-peptide Epoxides.

[Structure: Cbz-Ala-Ala-AAsn-EP-R₃ type compound]

| inhibitor | R₃ | Stereo-chemistry | Schistosome Legumain IC$_{50}$ (nM) | Pig Kidney Legumain k$_{obs}$/[I] (M$^{-1}$s$^{-1}$) |
|---|---|---|---|---|
| 12a | COOEt | S,S | 53 ± 25 | 43,000 |
|  | COOEt | R,R | 788 ± 88 | 25,200 |
|  | COOEt | trans |  | 15,600 |
|  | COOEt | cis |  | 140 |
| 12b | COOCH$_2$Ph | S,S | 47 ± 33 | 26,700 |
|  | COOCH$_2$Ph | trans |  | 28,900 |
| 12c | COOCH$_2$CH$_2$Ph | S,S | 45 |  |
| 12d | CONHCH$_2$Ph | S,S | NI | NI |
| 12e | CONHCH$_2$CH$_2$Ph | S,S | NI | NI |
| 12f | CO-Ala-NH-Bzl | R,R | NI |  |
| 12g | CON(nBu)$_2$ | S,S | 68 ± 4 |  |
| 12h | CON(CH$_3$)CH$_2$Ph | S,S | 63 ± 11 |  |
| 12i | CH$_2$CH$_2$Ph | trans | 70 ± 14 |  |
| 12j | Ph-4-Cl | trans | 90 ± 0 |  |

NI = no inhibition.

Legumain is inhibited by a variety of AAsn derivatives which are either not inhibitors for caspases or very poor. Both Schistosome and pig kidney legumain are inhibited.

Overall, the aza-peptide epoxide inhibitors have worked with every cysteine protease we have tested. The rates are higher with cysteine proteases that belong to clan CD compared to clan CA.

3. Inhibition Mechanism

The active site of cysteine proteases contains a cysteine and a histidine residue. The proposed mechanism involves the attack of the active site cysteine residue on the epoxide functional group to form a covalent adduct. An example of a caspase inhibitor is shown in the following figure. The enzyme recognizes the P1 AAsp residue and inhibition occurs. Additional interactions would occur between the extended substrate binding site of the cysteine protease and the inhibitor which would increase the binding affinity and specificity of the inhibitors.

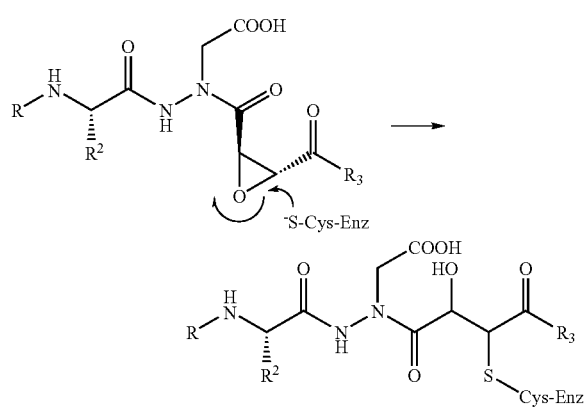

The peptide and amino acid aza-peptide epoxide derivatives, as shown above, bind to the enzymes using many of the interactions that are found in complexes of a particular enzyme with its substrates and/or inhibitors. Additional interactions with the enzyme can be obtained by tailoring the R$_3$ group of the inhibitor to imitate the amino acid residues which are preferred by an individual protease at the S1' and S2' subsites. For example, aza-peptide epoxides with R$_3$ phenylalkyl groups would interact effectively with caspase-1, which is shown to prefer such structures in alpha-ketoamide peptide inhibitors. Likewise, the M$_1$ group can interact with the S subsites of the target cysteine protease. Once a good inhibitor structure for a particular enzyme is found, it is then possible to change other characteristics such as solubility or hydrophobicity by adding substituents to the M$_1$ or R$_1$ and R$_2$ groups.

The following structures are inhibitors for the listed enzymes. The inhibitor sequences were obtained from peptide substrate and/or inhibitor sequences in the protease literature.

C$_1$-C$_6$H$_4$CH$_2$OCO-Phe-AGly-EP-COOH for papain
C$_6$H$_5$CH$_2$NHCO-Gly-Phe-AGly-EP-COOH for cathepsin B
Morpholine-CO-2-Naphthyl-AHph-EP-COOEt for cathepsin S
2-Naphthyl-SO$_2$-Ile-ATrp-EP-COOH for cathepsin B
1-Naphthyl-SO$_2$-Val-ATrp-EP-COOH for cathepsin B and L
Pro-Phe-AArg-EP-COOH for cathepsin B and L
Cbz-Phe-Leu-Leu-AMet(O$_2$)-EP-COOH for cathepsin K
Ph-CH$_2$—SO$_2$-AAsp-EP-COOCH$_2$Ph for caspase-1
Ph-CH$_2$CHFCO-Val-Ala-AAsp-EP-COOCH$_2$Ph for caspase-1
4-Cl-PhCH$_2$CH$_2$CO-Val-Ala-AAsp-EP-COOCH$_2$Ph for caspase-1
4-NO$_2$-PhCH$_2$CH$_2$CO-Val-Ala-AAsp-EP-COOCH$_2$Ph for caspase-1
4-CH$_3$O-PhCH$_2$CH$_2$CO-Val-Ala-AAsp-EP-COOCH$_2$Ph for caspase-1
3-F-PhCH$_2$CH$_2$CO-Val-Ala-AAsp-EP-COOCH$_2$Ph for caspase-1
3,4-dichloro-PhCH$_2$CH$_2$CO-Val-Ala-AAsp-EP-COOCH$_2$Ph for caspase-1
Naphthyl-CH$_2$OCO-Val-Ala-AAsp-EP-COOCH$_2$Ph for caspase-1
4-CF$_3$-PhCH$_2$CH$_2$CO-Val-Ala-AAsp-EP-COOCH$_2$Ph for caspase-1
4-CH$_3$-PhCH$_2$CH$_2$CO-Val-Ala-AAsp-EP-COOCH$_2$Ph for caspase-1
PhCH$_2$NHCO-Val-Ala-AAsp-EP-COOCH$_2$Ph for caspase-1
4-HO-PhCH$_2$CH$_2$CO-Val-Ala-AAsp-EP-COOCH$_2$Ph for caspase-1
4-Cl-Ph-CH$_2$OCO-Leu-Glu-Thr-AAsp-EP-COOEt for caspase-8
4-Cl-Ph-CH$_2$OCO-Ile-Glu-Thr-AAsp-EP-COOEt for caspase-8
4-Cl-Ph-CH$_2$OCO-Asp-Glu-Val-AAsp-EP-COOEt for caspase-3
C$_5$H$_9$—OCO-Asp-Glu-Val-AAsp-EP-COOEt for caspase-3
3-F-Ph-CH$_2$OCO-Ala-Ala-AAsn-EP-COOEt for legumain
4-PhO-PhCH$_2$OCO-Ala-Ala-AAsn-EP-COOEt for legumain
3-F-Ph-CH$_2$OCO-Leu-Glu-Thr-AAsp-EP-COOEt for caspase-6
PhCH$_2$CH$_2$CO-Val-Ala-AAsp-EP-COO(CH$_2$)$_2$Ph-4-Cl for caspase-1
Cbz-Leu-Glu-Thr-AAsp-EP-COO(CH$_2$)$_2$Ph-4-CH$_3$ for caspase-8
Cbz-Leu-Glu-Thr-AAsp-EP-COOCH$_2$C$_6$H$_{11}$ for caspase-8
Cbz-Asp-Glu-Val-AAsp-EP-COO(CH$_2$)$_2$C$_6$H$_4$-p-OCH$_3$ for caspase-3

Cbz-Ala-Ala-AAsn-EP-COO(CH$_2$)$_2$-2-naphthyl for legumain
PhCH$_2$CH$_2$CO-Val-Ala-AAsp-EP-(CH$_2$)$_2$Ph-3-F for caspase-1
PhCH$_2$CH$_2$CO-Val-Ala-AAsp-EP-COO(CH$_2$)$_2$-2-naphthyl for caspase-1
Cbz-Leu-Glu-Thr-AAsp-EP-COO(CH$_2$)$_2$C$_6$H$_4$-p-NO$_2$ for caspase-6
Cbz-Ala-Ala-AAsn-EP-COO(CH$_2$)$_2$C$_6$H$_4$-p-CN for legumain
PhCH$_2$CH$_2$CO-Val-Ala-AAsp-EP-COO(CH$_2$)$_2$C$_6$H$_4$-m-OPh for caspase-1
2,4-dinitrophenyl-Ahx-Gly-Phe-AAla-EP-COOH for cathepsin L
Cbz-Leu-ALys-EP-COOEt gingipain
Cbz-Leu-AOm-EP-COOEt gingipain
Cbz-Leu-ALys-EP-COOEt clostripain
Cbz-Leu-AOm-EP-COOEt clostripain
Cbz-Lys(Biotinyl)-Val-Ala-AAsp-EP-COOEt caspase-1

4. In Vitro Uses.

To use the above inhibitors in vitro, they are dissolved in an organic solvent such as dimethylsulfoxide or ethanol, and are added to an aqueous solution containing serine and/or cysteine proteases. The final concentration of the organic solvent should be less than 25%. The inhibitors may also be added as solids or in suspension. The cysteine protease inhibitors of this disclosure would be useful in a variety of experimental procedures where proteolysis is a significant problem. Inclusion of these inhibitors in radioimmunoassay experiments would result in higher sensitivity. The use of these inhibitors in plasma fractionation procedures would result in higher yields of valuable plasma proteins and would make purification of the proteins easier. The inhibitors disclosed here could be used in cloning experiments utilizing bacterial cultures, yeast, and human cells to produce a purified cloned product in higher yield.

The novel compounds of this disclosure are effective in the prevention of unnecessary proteolysis caused by cysteine proteases in the process of purification, transport and storage of peptides and proteins as shown in Tables I-VI by effective inhibition of many cysteine proteases.

Diagnostic Reagents

Aza-peptide epoxides of the present disclosure can be used for the identification of proteases, for example novel cysteine proteases. One embodiment provides a method for screening a sample for the presence of a protease, particularly a cysteine protease, by contacting the sample with an aza-peptide epoxide, for example an aza-peptide epoxide of Formula I, and detecting the presence of the the aza-peptide epoxide-protease conjugate. Detection of the conjugate may be accomplished using known techniques. For example, aza-peptide epoxides of the present disclosure can be modified with a detectable label including but not limited to a radioisotope, fluorescent marker, biotin, antibody, enzyme conjugate such as horseradish peroxidase, or the like. The aza-peptide conjugates can be fixed to a support, for example using known chemical fixatives, and a sample can then by added to the aza-peptide epoxide. Such support can be microarrays or the like. The fixed aza-peptide epoxide can then irreverisible or reverisibly bind a protease, for example a cysteine protease, in the sample. The support can be washed to remove excess sample. The aza-peptide epoxide-protease conjugate can then be eluted from the support and the protease can be detected or identified using conventional techniques. The support can be any durable substance including but not limited to metal, plastic, glass, quartz or the like. The aza-peptide epoxides can be linked to the support with a linker, for example a cleavable linker to facilliate the removal of aza-peptide epoxide-protease conjugates.

5. In Vivo Uses.

Effective inhibitors of the proteolytic function of caspases (Tables IV and V) can be used to treat a variety of diseases. Excessive cell death can result from acquired or genetic conditions which increase the accumulation of signals that induce apoptosis or that diminish the threshold at which such events induce apoptosis. Excessive apoptosis has been associated with a variety of disease states including neurodegenerative disorders, ischemic injuries, acquired immunodeficiency syndrome (AIDS), and osteoporosis. Apoptosis is involved in amyotrophic lateral sclerosis (ALS), Huntington's disease, Alzheimer's disease, Parkinson's disease, and spinal muscular atrophy. In multiple sclerosis (MS), the death of the oligodendrocytes is an important example of the glial degeneration through apoptosis.

Huntingtin, the first protein identified as a caspase substrate that is specifically involved in a neurodegenerative disease, is a substrate for proteolytic cleavage by caspase-3. Thus, aza-peptide epoxides would be useful for the treatment of Huntington's disease and other neurodegenerative diseases such as dentatorubropallidoluysian atrophy (DRPLA), spinocerebellar atrophy type 3 (SCA-3), and spinal bulbar muscular atrophy (SBMA).

Effector caspases cleave Alzheimer's gene products, presenilins 1 and 2 proteins. Recently, it has been shown that caspase-6 is involved in human neuronal cell apoptosis, amyloidogenesis, and Alzheimer's disease. Amyloid β peptide (Aβ), which builds up in the brains of people with Alzheimer's disease, causes cultured neurons to die by apoptosis. Thus effective caspase-6 aza-peptide epoxide inhibitors (Tables IV and V) can be used for the treatment of Alzheimer's disease.

In models related to Parkinson disease, peptide caspase inhibitors protect against 1-methyl-4-phenylpyridinium (MPP$^+$)-induced apoptosis of cultured cerebellar granular neurons and increase the rate of survival. Also, in mice overexpressing Bcl-2, dopaminergic 1-methyl-4-phenyl-1,2,3,6-tetrahydropyridine (MPTP) caspase activity is blocked, toxicity is decreased, and substantial nigra neurons survive. Thus, effective caspase aza-peptide epoxide inhibitors (Table IV) can be used for the treatment of Parkinson's disease.

Neuronal apoptosis is also seen after acute injuries such as stroke, trauma, and ischemia. Apoptosis has been observed in striatal and cortical neurons in animal models of stroke. Transgenic mice, expressing a caspase-1 inhibitor, are protected from ischemic damage after middle cerebral artery occlusion. During ischemia, activated caspases dismantle the cell by cleaving multiple substrates such as the enzymes essential for cell repair and cytoskeletal proteins. Therefore, caspase activation develops in models of global ischemia and may accompany the ischemic component of head injury. The effect of irreversible inhibitors (Z-VAD-FMK, Z-DEVD-FMK, and YVAD-CMK) on ischemia-induced tissue shows that caspase-1 and caspase-3 are involved in the mechanism of cell death in ischemic and excitotoxic brain injury. Caspases are recognized as novel therapeutic targets for central nervous diseases in which cell death occurs mainly by the mechanism of apoptosis. Thus effective caspase aza-peptide epoxide inhibitors (Tables IV and V) can be used for the treatment of many diseases involving apoptosis.

Effective caspase aza-peptide epoxide inhibitors are particularly useful for treatment of nerve degeneration associated with conditions and/or disorders including, but not limited to, neuropathies; idiopathic peripheral neuropathies; peripheral neuropathies due to genetic mutations; stroke;

Alzheimer's disease; Parkinson's disease; Huntington's disease, dentatorubropallidoluysian atrophy; spinocerebellar atrophy; spinal bulbar muscular atrophy; peripheral neuropathies associated with uremia, rheumatologic diseases, liver diseases, or infections; axonal degeneration secondary to primary demyelinating disorders, inflammatory demyelinating neuropathies, multiple sclerosis, or chronic spinal cord degenerations; amyotrophic lateral sclerosis; a motor neuron disease; the presence of metabolic derangements such as diabetes or uremia, central or peripheral ischemia; genetic susceptibility to nerve degeneration; or exposure to a neurotoxic agent. Such neurotoxic agents include, but are not limited to, some an anti-cancer agents, especially those causing microtuble stabilixation or disruption. Some exemplary anticancer drugs known to result in peripheral neuropathy include, but are not limited to, vincristine, cisplatin, and paclitaxel (Taxol®)

Aza-peptide epoxides can be used to control protein turnover, muscular dystrophy, myocardial tissue damage, tumor metastasis, and bone resorption as shown in Table I by effective inhibition of lysosomal cathepsin B in buffer. Peptide aza-peptide epoxides can also be used as neuroprotectants or for the treatment of ischemia, stroke, or Alzheimer's disease as shown in Table I by effective inhibition of calpain I and calpain II.

6. Treatment of Peripheral Neuropathy.

Embodiments of the present disclosure describe compositions and methods for the treatment of a pathology, in particular a neural pathology such as cytoskeletal degeneration of peripheral neurons, peripheral neuropathy, or axonal degeneration including sensory neuron axonal degeneration. The neural pathology can be related to a disease or condition such as diabetes, or can be the result of contact with a chemcial agent including neurotoxic agents, such as certain anticancer agents, including those listed above. One of the several embodiments of the present disclosure provides a method for treating a neural pathology of the peripheral nervous system, for example nerve degeneration, more specificially axonal degeneration, by administering to a patient a therapeutically effective amount of an aza-peptide epoxide, preferrably an aza-peptide epoxide capable of inhibiting caspases and/or calpains.

Axonal degeneration is a feature common to a wide spectrum of neurologic disorders, and axonal degeneration is the pathology that underlies clinical dysfunction in these disorders. These diseases include, but are not limited to, peripheral neuropathies due to genetic mutations; peripheral neuropathies associated with other systemic diseases including uremia, rheumatologic diseases, liver diseases, and infections; axonal degeneration secondary to primary demyelinating disorders including inflammatory demyelinating neuropathies and multiple sclerosis; and nerve degeneration associated with exposure to a neurotoxic agent, such as an anti-cancer agent.

As demonstrated in the examples below, the aza-peptide epoxide compounds of the present disclosure are effective in preventing axonal degeneration in these and other disorders and will thus constitute a novel treatment for such diseases. In other embodiments, the aza-peptide epoxides of the present disclosure can be administered simultaneous with a calpain inhibitor that is also effective in treating nerve degeneration associated with the conditions listed above, among others. Embodiments of calpain inhibitors useful for treating nerve degeneration are discussed in greater detail in U.S. patent application Ser. No. 10/671,360, which is incorporated by reference herein in its entirety, along with their synthetic procedures and examples.

Calpain inhibitors useful in alone or in combination with the aza-peptide epoxides of the present disclosure include, but are not limited to, calpain inhibitors with the formula:

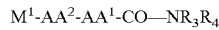

a pharmaceutically acceptable salt or prodrug thereof, wherein $M^1$ is selected from the group consisting of H, $NH_2$—CO—, $NH_2$—CS—, $NH_2$—$SO_2$—, X—NH—CO—, $X_2N$—CO—, X—NH—CS—, $X_2N$—CS—, X—NH—$SO_2$—, $X_2N$—$SO_2$—, X—CO—, X—CS—, X—, Y—$SO_2$—, Y—O—CO—, Y—O—CS—, morpholine-CO—, and biotinyl;

X is selected from the group consisting of H, $C_{1-10}$ alkyl, $C_{3-15}$ cyclized alkyl, $C_{1-10}$ fluoroalkyl, $C_{1-10}$ alkyl substituted with J, $C_{1-10}$ fluoroalkyl substituted with J, 1-admantyl, 9-fluorenyl, phenyl, phenyl monosubstituted with K, phenyl disubstituted with K, phenyl trisubstituted with K, naphthyl, naphthyl monosubstituted with K, naphthyl disubstituted with K, naphthyl trisubstituted with K, $C_{1-10}$ fluoroalkyl with an attached phenyl group, $C_{1-10}$ alkyl with an attached phenyl group, $C_{1-10}$ alkyl with two attached phenyl groups, $C_{1-10}$ alkyl with an attached phenyl group substituted with K, $C_{1-10}$ alkyl with two attached phenyl groups substituted with K, $C_{1-10}$ alkyl with an attached naphthyl group, $C_{1-10}$ alkyl with an attached naphthyl group substituted with K, $C_{1-10}$ alkyl with an attached phenoxy group, and $C_{1-10}$ alkyl with an attached phenoxy group substituted with K on the phenoxy group, and $C_{1-10}$ alkyl monosubstituted with $M^2$;

Y is selected from the group consisting of $C_{1-10}$ alkyl, $C_{3-15}$ cyclized alkyl, $C_{1-10}$ fluoroalkyl, $C_{1-10}$ alkyl substituted with J, $C_{1-10}$ fluoroalkyl substituted with J, 1-admantyl, 9-fluorenyl, phenyl, phenyl monosubstituted with K, phenyl disubstituted with K, phenyl trisubstituted with K, naphthyl, naphthyl monosubstituted with K, naphthyl disubstituted with K, naphthyl trisubstituted with K, $C_{1-10}$ fluoroalkyl with an attached phenyl group, $C_{1-10}$ alkyl with an attached phenyl group, $C_{1-10}$ alkyl with two attached phenyl groups, $C_{1-10}$ alkyl with an attached phenyl group substituted with K, $C_{1-10}$ alkyl with two attached phenyl groups substituted with K, $C_{1-10}$ alkyl with an attached naphthyl group, $C_{1-10}$ alkyl with an attached naphthyl group substituted with K, $C_{1-10}$ alkyl with an attached phenoxy group, and $C_{1-10}$ alkyl with an attached phenoxy group substituted with K on the phenoxy group, $M^2$, and $C_{1-10}$ alkyl monosubstituted with $M^2$;

$M^2$ is selected from the group consisting of 2-furyl, 2-tetrahydrofuryl, 2-pyridyl, 3-pyridyl, 4-pyridyl, 2-pyrazinyl, 2-quinolinyl, 1-tetrahydroquinolinyl, 1-isoquinolinyl, 2-tetrahydroisoquinolinyl, and —$N(CH_2CH_2)_2O$;

J is selected from the group consisting of halogen, $CO_2H$, OH, CN, $NO_2$, $NH_2$, $C_{1-10}$ alkoxy, $C_{1-10}$ alkylamino, $C_{2-12}$ dialkylamino, $C_{1-10}$ alkyl-O—CO—, $C_{1-10}$ alkyl-O—CO—NH—, $C_{1-10}$ alkyl-S—, and —$N(CH_2CH_2)_2O$;

K is selected from the group consisting of halogen, $C_{1-10}$ alkyl, $C_{1-10}$ perfluoroalkyl, $C_{1-10}$ alkoxy, phenoxy, $NO_2$, CN, OH, $CO_2H$, amino, $C_{1-10}$ alkylamino, $C_{2-12}$ dialkylamino, $C_{1-10}$ acyl, and $C_{1-10}$ alkoxy-CO—, and $C_{1-10}$ alkyl-S—, and —$N(CH_2CH_2)_2O$;

$AA^1$ and $AA^2$ side chain blocked or unblocked amino acids with the L configuration, D configuration, or no chirality at the α-carbon selected from the group consisting of alanine, valine, leucine, isoleucine, proline, methionine, methionine sulfoxide, phenylalanine, tryptophan, glycine, serine, threonine, cysteine, tyrosine, asparagine, glutamine, aspartic acid, glutamic acid, lysine, arginine, histidine, phenylglycine, beta-alanine, norleucine, norvaline, alpha-aminobutanoic acid, epsilon-aminocaproic acid, citrulline, hydroxyproline, ornithine, homoarginine, sarcosine, indoline 2-carboxylic acid, 2-azetidinecarboxylic acid, pipecolinic acid (2-piperidine carboxylic acid), O-methylserine, O-ethylserine, S-methylcysteine, S-ethylcysteine, S-benzylcysteine, $NH_2$—CH($CH_2CHEt_2$)—$CO_2H$, alpha-aminoheptanoic acid, $NH_2$—CH($CH_2$-1-naphthyl)-$CO_2H$, $NH_2$—CH($CH_2$-2-naphthyl)-$CO_2H$, $NH_2$—CH($CH_2$-cyclohexyl)-$CO_2H$, $NH_2$—CH($CH_2$-cyclopentyl)-$CO_2H$, $NH_2$—CH($CH_2$-cyclobutyl)-$CO_2H$, $NH_2$—CH($CH_2$-cyclopropyl)-$CO_2H$, trifluoroleucine, 4-fluorophenylalanine, lysine substituted on the epsilon nitrogen with a biotinyl group, hexafluoroleucine, and $NH_2$—$CHR^2$—$CO_2H$;

$R^2$ is selected from the group consisting of $C_{1-10}$ branched and unbranched alkyl, $C_{1-10}$ branched and unbranched cyclized alkyl, and $C_{1-10}$ branched and unbranched fluoroalkyl;

$R^3$ and $R^4$ are selected independently from the group consisting of a) H, $C_{1-20}$ alkyl, $C_{1-20}$ cyclized alkyl, $C_{1-20}$ alkyl with a phenyl group attached to the $C_{1-20}$ alkyl, $C_{1-20}$ cyclized alkyl with an attached phenyl group, $C_{1-20}$ alkyl with an attached phenyl group monosubstituted with K, $C_{1-20}$ alkyl with an attached phenyl group disubstituted with K, $C_{1-20}$ alkyl with an attached phenyl group trisubstituted with K, $C_{1-20}$ cyclized alkyl with an attached phenyl group monosubstituted with K, $C_{1-10}$ alkyl with a morpholine [—N($CH_2CH_2$)O] ring attached through nitrogen to the alkyl, $C_{1-10}$ alkyl with a piperidine ring attached through nitrogen to the alkyl, $C_{1-10}$ alkyl with a pyrrolidine ring attached through nitrogen to the alkyl, $C_{1-20}$ alkyl with an OH group attached to the alkyl, —$CH_2CH_2OCH_2CH_2OH$, $C_{1-10}$ with an attached 4-pyridyl group, $C_{1-10}$ with an attached 3-pyridyl group, $C_{1-10}$ with an attached 2-pyridyl group, $C_{1-10}$ with an attached cyclohexyl group, —NH—$CH_2CH_2$-(4-hydroxyphenyl), —NH—$CH_2CH_2$-(3-indolyl));

b) —$CH_2CH(OH)$—$R^5$, and c) —$(CH_2)_n$—$R^7$;

$R^5$ is selected from the group consisting of phenyl, phenyl monosubstituted with J, phenyl disubstituted with J, phenyl trisubstituted with J, pentafluorophenyl,

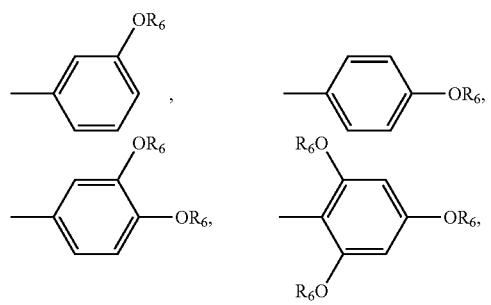

1-naphthyl, 1-naphthyl monosubstituted with J, 1-naphthyl disubstituted with J, 2-naphthyl, 2-naphthyl monosubstituted with J, 2-naphthyl disubstituted with J, 2-pyridyl, 2-quinolinyl, and 1-isoquinolinyl;

$R^6$ is selected from the group consisting of $C_{1-4}$ alkyl, $C_{1-4}$ alkyl substituted with phenyl, phenyl, and phenyl substituted with J; n=1-6;

$R^7$ is selected from the group consisting of 2-furyl, 2-furyl monosubstituted with J, 2-pyridyl, 2-pyridyl monosubstituted with J, 3-pyridyl, 3-pyridyl monosubstituted with J, 4-pyridyl, 4-pyridyl monosubstituted with J, 2-quinolinyl, 2-quinolinyl monosubstituted with J, 1-isoquinolinyl, 1-isoquinolinyl monosubstituted with J,

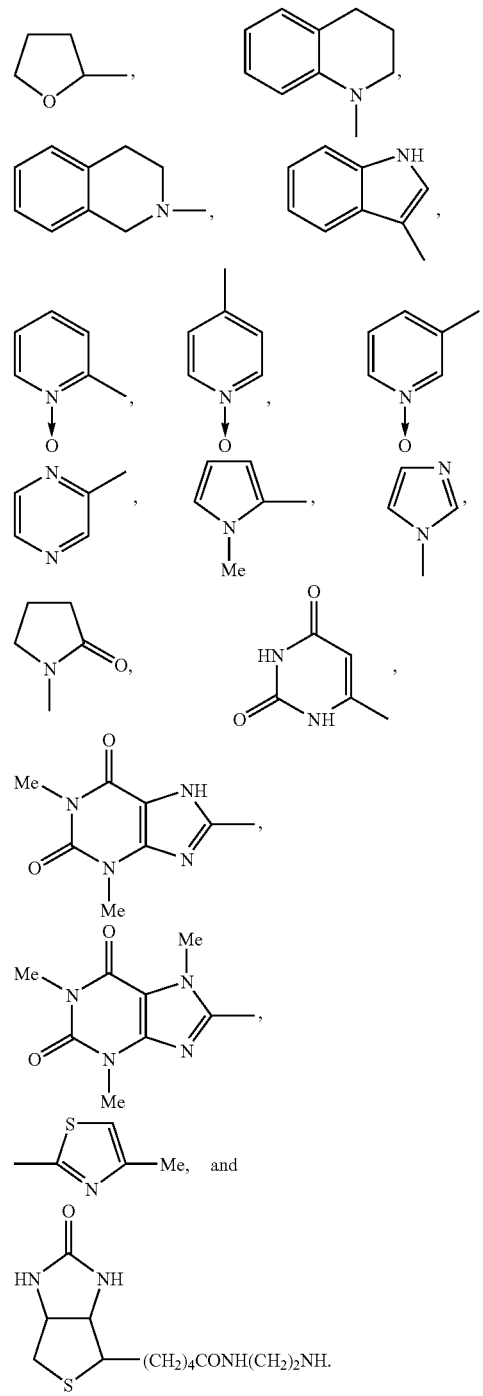

In particular, exemplary calpain inhibitors useful for treating nerve degeneration alone, or in combination with the aza-peptide epoxide compounds include, but are not limited to the following:

Z-Leu-Nva-CONHCH$_2$-2-pyridyl,
Z-Leu-Abu-CONHCH$_2$CH(OH)C$_6$F$_5$,
Z-Leu-Phe-CONH(CH$_2$)$_2$Ph,
Z-Leu-Abu-CONHCH$_2$CH(OH)C$_6$H$_4$-3-OC$_6$H$_4$(3-CF$_3$),
Z-Leu-Abu-CONHCH$_2$CH(OH)C$_6$H$_4$(4-OCH$_2$Ph), Z-Leu-Abu-CONHCH₂CH(OH)C₆H₄(4-OPh),
Z-Leu-Phe-CONHCH₂-2-quinolinyl,
Z-Leu-Abu-CONH(CH₂)₂C₆H₄(3-OCH3),
Z-Leu-Abu-CONH(CH₂)₂C₆H₄(4-OCH3),
Z-Leu-Abu-CONHCH₂CH(OH)-1-C₁₀H₇,
Z-Leu-Phe-CONH(CH₂)₃-4-morpholinyl,
Z-Leu-Abu-CONH(CH₂)₂C₆H₄(2-OCH₃),
Z-Leu-Abu-CONHCH₂-2-quinolinyl,
Z-Leu-Abu-CONH(CH₂)₃-4-morpholinyl (AK295),
Z-Leu-Abu-CONH(CH₂)₂-2-(N-methylpyrrole),
Z-Leu-Phe-CONHCH₂CH(OH)C₆H₄-3-OC₆H₄(3-CF₃),
Z-Leu-Abu-CONH(CH₂)₂C₆H₅,
Z-Leu-Phe-CONH-Et,
Z-Leu-Abu-CONHCH₂CH(OC₂H₅)₂,
Z-Leu-Phe-CONHCH₂CH(OH)C₆H₄(4-OPh),
Z-Leu-Phe-CONHCH₂CH(OH)C₆H₄(4-OCH₂Ph),
Z-Leu-Abu-CONHCH₂C₆H₅,
Z-Leu-Phe-CONH(CH₂)₂NH-biotinyl,
Z-Leu-Phe-CONH(CH₂)₃-2-tetrahydroisoquinolinyl,
Z-Leu-Abu-CONHCH₂CH(OH)C₆H₃(3,4-(OCH₂Ph)₂),
Z-Leu-Abu-CONHCH₂CH(OH)C₆H₄(4-OCH₃),
Z-Leu-Nva-CONH(CH₂)₃-4-morpholinyl,
Z-Leu-Abu-CONHCH₂-1-isoquinolinyl,
Z-Leu-Abu-CONHEt,
Z-Leu-Abu-CONHCH₂CH(OH)C₆H₄-3-OC₆H₃(3,4-C₁₂),
Z-Leu-Abu-CONHMe,
Z-Leu-Abu-CONH(CH₂)₃-1-imidazolyl,
Z-Leu-Abu-CONH(CH₂)₂-3-indolyl,
Z-Leu-Abu-CONH(CH₂)₃-2-tetrahydroisoquinolinyl,
Z-Leu-Abu-CONHCH₂-2-tetrahydrofuryl,
Z-Leu-Abu-CONHCH₂CH(OH)C₆H₄(4-N(CH₃)₂),
Z-Leu-Phe-CONH-n-Pr,
Z-Leu-Abu-CONHCH₂CH(OH)-2-C₁₀H₇,
Z-Leu-Phe-CONH-Me,
Z-Leu-Abu-CONHCH₂CH(OH)C₆H₄(3-CF₃),
Z-Leu-Abu-CONH(CH₂)₃-1-tetrahydroquinolinyl,
Z-Leu-Abu-CONH(CH₂)₂C₆H₄(4-OH),
Z-Leu-Abu-CONHCH₂CH(OH)C₆H₂(3,4,5-(OCH₃)₃),
Z-Leu-Phe-CONH(CH₂)₃-1-tetrahydroquinolinyl,
Z-Leu-Abu-CONH(CH₂)₂-2-pyridyl,
Z-Leu-Abu-CONHCH₂—C₆H₇(1,3,3-(CH₃)₃-5-OH),
Z-Leu-Phe-CONHCH₂CH(OH)C₆H₄(3-CF3),
Z-Leu-Phe-CONHCH₂CH(OH)C₆H₃(3,4-(OCH₂Ph)₂),
Z-Leu-Abu-CONH(CH₂)₅OH,
Z-Leu-Abu-CONHCH₂CH(OCH₃)₂,
Z-Leu-Phe-CONHCH₂CH(OH)C₆H₄-3-OC₆H₃(3,4-C₁₂),
Z-Leu-Phe-CONHCH₂CH(OH)C₆H₄(3-OPh),
Z-Leu-Phe-CONHCH₂CH(OH)C₆H₄(4-N(CH₃)₂),
Z-Leu-Abu-CONHCH₂-2-pyridyl,
Z-Leu-Abu-CONH(CH₂)₂O(CH₂)₂OH,
Z-Leu-Phe-CONHCH₂-2-pyridyl,
Z-Leu-Abu-CONH(CH₂)₂NH-biotinyl,
Z-Leu-Abu-CONHCH₂—C₆H₁₁,
Z-Leu-Phe-CONHCH₂CH(OH)C₆F₅,
Z-Leu-Abu-CONHCH₂-2-furyl,
Z-Leu-Abu-CONH(CH₂)₃C₆H₅,
Z-Leu-Abu-CONH(CH₂)₂OH,
Z-Leu-Abu-CONHCH₂CH(OH)C₆H₄(3-OPh),
Z-Leu-Abu-CONH(CH₂)₂-4-morpholinyl,
Z-Leu-Abu-CONHCH₂CH(OH)Ph,
Z-Leu-Abu-CONHCH₂-4-pyridyl,
Z-Leu-Abu-CONH(CH₂)₃-1-pyrrolidine-2-one,
Z-Leu-Phe-CONHCH₂CH(OH)Ph,
Z-Leu-Abu-CONHCH₂C₆H₃(3,5-(OCH₃)₂),
Z-Leu-Nva-CONHCH₂CH(OH)Ph,
Z-Leu-Abu-CONHCH₂-8-caffeinyl,
Z-Leu-Abu-n-Pr,
Z-Leu-Abu-CONHCH₂-3-pyridyl, and
Z-Leu-Phe-CONHCH₂Ph.

Exemplary calpain inhibitors for use in combination with the aza-peptide epoxide compounds of the present disclosure include, but are not limited to, peptide alpha-keto amides such as Z-Leu-Abu-CONH—(CH₂)₃-4-morpholinyl (AK295). Additionally, the aza-peptide epoxides of the present disclosure, particularly those effective at caspase and/or calpain inhibition, can be administered, alone or in combination with a calpain inhibitor (e.g. AK295), simultaneously with the administration of an anti-cancer drug, particularly an anti-cancer drug known to induce nerve degeneration. In an exemplary embodiment, an aza-peptide epoxide caspase inhibitor, preferrably of the formula Cbz-Asp-Glu-Val-AAsp-EP-COOEt (JG36) is combined with a peptide alpha-keto amide calpain inhibitor, preferrably AK295. In another exemplary embodiment, an aza-peptide epoxide caspase inhibitor, alone or in combination with AK295, is administered to a mammalian host, for example, a patient, undergoing chemotherapy with an anti-cancer agent including, but not limited to, vincristine, cisplatin, and paxlitaxel (Taxol®).

As discussed in greater detail in Example 6, below, both the aza-peptide epoxide caspase inhibitor Cbz-Asp-Glu-Val-AAsp-EP-COOEt (JG36) and the the peptide ketoamide calpain inhibitor Cbz-Leu-Abu-CONH—(CH₂)₃-4-morpholinyl (AK295) inhibited vincristine-induced axonal degeneration in rat dorsal root ganglia (DRG) cutlures in vitro. These results demonstrate the usefulness of these and similar compounds, (individually and in combination) for use in treating and/or preventing other neurotoxin-induced peripheral neuropathies, as well as other neural pathologies.

7. Drug Delivery.

This disclosure also provides a pharmaceutical composition which comprises a compound according to Formula I and a pharmaceutically accepted carrier, diluent or excipient. Accordingly, the compounds of Formula I may be used in the manufacture of a medicament. For therapeutic use, the peptide aza-peptide epoxides may be administered orally, topically, or parenterally. The term parenteral, as used, includes subcutaneous injection, intravenous, intramuscular, intrastemal injection, or infusion techniques. The dosage depends primarily on the specific formulation and on the object of the therapy or prophylaxis. The amount of the individual doses as well as the administration is best determined by individually assessing each case.

The pharmaceutical compositions containing the active ingredient may be in a form suitable for oral use, for example, as tablets, troches, lozenges, aqueous or oily suspensions, dispersible powders or granules, emulsions, hard or soft capsules, syrups, or elixirs. Dosage levels of the order of 0.2 mg to 140 mg per kilogram of body weight per day are useful in the treatment of the above-indicated conditions (10 mg to 7 gms per patient per day). The amount of active ingredient that may be combined with carrier materials to produce a single dosage form will vary depending upon the host treated and the particular mode of administration.

For injection, the therapeutic amount of the peptide aza-peptide epoxides or their pharmaceutically acceptable salts will normally be in the dosage range from 0.2 to 140 mg/kg of body weight. Administration is made by intravenous, intramuscular, or subcutaneous injection. Accordingly, pharmaceutical compositions for parenteral administration will contain from about 10 mg to 7 gms of the compounds per dose. In addition to the active ingredient, these pharmaceutical compositions will usually contain a buffer, e.g. a phosphate buffer, which keeps the pH in the range from 3.5 to 7, and sodium chloride, mannitol, or sorbitol for adjusting the isotonic pressure.

A composition for topical application can be formulated as an aqueous solution, lotion, jelly or an oily solution or suspension. A composition in the form of an aqueous solution is obtained by dissolving the compounds of this disclosure in aqueous buffer solution of pH 4 to 6.5 and, if desired, adding a polymeric binder. An oily formulation for topical application is obtained by suspending the compounds of this disclosure in an oil, optionally with the addition of a swelling agent such as aluminium stearate and/or a surfactant.

EXAMPLES

The following detailed examples are given to illustrate the present disclosure and are not intended to limit it in any manner. Examples describing the synthesis and composition of additional aza-peptide epoxide compounds are included in U.S. patent application Ser. No. 10/603,054, which is hereby incorporated herein by reference in its entirety.

Example 1

Pentafluorophenol Coupling Method. (2R,3R)-3-($N^2$-(N-Benzyloxycarbonylleucyl-t-butoxyglutamylthreonyl)-$N^1$-t-butoxycarbonylmethylhydrazinocarbonyl)oxirane-2-carboxylic Acid Ethyl Ester (Cbz-Leu-Glu(O-tBu)-Thr-AAsp(O-tBu)-(2R,3R)-EP-COOEt). Coupling of Cbz-Leu-Glu(O-tBu)-Thr-NH—NH—CH$_2$COO-tBu with 5 (Y=COOEt) was accomplished using the pentafluorophenol method. The epoxide 5 (1 eq, Y=COOEt) in DMF was reacted with pentafluorophenol (1 eq) and DCC (1 eq) in DMF at 0° C. The reaction was allowed to reach room temperature and then was stirred for 24 hours. Dicyclohexylurea was removed by filtration and the filtrate was evaporated to dryness under reduced pressure. The peptide Cbz-Leu-Glu(O-tBu)-Thr-NH—NH—CH$_2$COO-tBu (1 eq) in DMF was added to the residue and the reaction was allowed to stir at room temperature for 24 hours. The solvent was evaporated and the product was purified by chromatography using two silica gels columns, the first column with 1:9 MeOH:CH$_2$Cl$_2$ as the eluent, followed by another column with 2:1 EtOAc:hexane as the eluent; white solid, yield 16%. MS and $^1$H NMR (CDCl$_3$) were consistent with the proposed structure.

Example 2

Mixed Anhydride Coupling Method. Coupling of bulky peptides, such as Z-Asp(O-tBu)-Glu(O-tBu)-Val-NH—NH$_2$—COO-tBu and Cbz-Leu-Glu(O-tBu)-Thr-NH—NH—CH$_2$COO-tBu, with 5 (Y=COOEt), was accomplished using the mixed anhydride method. To a solution of 5 (5 eq) in DMF at 0° C. was added N-methylmorpholine (NMM, 5 eq) followed isobutyl chloroformate (IBCF, 5 eq). After the reaction mixture was allowed to stir for 30 min, the substituted hydrazide (1 eq) dissolved in DMF was added to the mixture. After 10 min the ice bath was removed and the reaction was stirred for 16 hr at room temperature. The DMF was evaporated and the residue was washed and purified using the same procedure as described above for the EDC/HOBT coupling. MS and $^1$H NMR (DMSO-d$_6$ or CDCl$_3$) were consistent with the proposed structures. Examples 3A-3C were prepared using this mixed anhydride method.

Example 3

Mixed Anhydride Coupling Method. Coupling of bulky peptides, such as Z-Asp(O-tBu)-Glu(O-tBu)-Val-NH—NH$_2$—COO-tBu and Cbz-Leu-Glu(O-tBu)-Thr-NH—NH—CH$_2$COO-tBu, with 5 (Y=COOEt), was accomplished using the mixed anhydride method. To a solution of 5 (5 eq) in DMF at 0° C. was added N-methylmorpholine (NMM, 5 eq) followed isobutyl chloroformate (IBCF, 5 eq). After the reaction mixture was allowed to stir for 30 min, the substituted hydrazide (1 eq) dissolved in DMF was added to the mixture. After 10 min the ice bath was removed and the reaction was stirred for 16 hr at room temperature. The DMF was evaporated and the residue was washed and purified using the same procedure as described above for the EDC/HOBT coupling. MS and $^1$H NMR (DMSO-d$_6$ or CDCl$_3$) were consistent with the proposed structures. Examples 3A-3I were prepared using this mixed anhydride method Example 3A Cbz-Asp(O-tBu)-Glu(O-tBu)-Val-AAsp(O-tBu)-(2S,3S)-EP-COOEt was purified using column chromatography on silica gel using 2:18:5 MeOH:CH$_2$Cl$_2$:EtOAc as the eluent; white solid, yield 58%.

Example 3B

Cbz-Asp(O-tBu)-Glu(O-tBu)-Val-AAsp(O-tBu)-(2R,3R)-EP-COOEt was purified using column chromatography on silica gel using 2:18:5 MeOH:CH$_2$Cl$_2$:EtOAc as the eluent; white solid, yield 57%.

Example 3C

Cbz-Leu-Glu(O-tBu)-Thr-AAsp(O-tBu)-(2S,3S)-EP-COOEt was purified by chromatography on two successive columns, using 1:13 MeOH:CH$_2$Cl$_2$ as the eluent, followed by column chromatography using 2:1 EtOAc:hexane as the eluent; white solid, yield 44%.

Example 3E

Cbz-Glu(O-tBu)-Val-AAsp(O-tBu)-(2S,3S)-EP-CONHCH$_2$CH$_2$Ph was obtained using the EDC/HOBt coupling method, purified by column chromatography on silica gel with 7:13:1:1 hexane:EtOAc:MeOH:CH$_2$Cl$_2$ as the eluent, and then rechromatographed using 3:1 EtOAc:hexane as the eluent; white solid, yield 35%. MS (ESI) m/z 782.4 [(M+1)$^+$]. $^1$H NMR (CDCl$_3$): 0.95 (d, 6H, Val), 1.45 (s, 18H, tBu), 1.90-2.30 (m, 3H, Val and Glu), 2.45 (m, 2H, Glu), 2.72 (t, 2H, NHCH$_2$CH$_2$Ph), 3.40 and 3.60 (m, 2 H, NHCH$_2$CH$_2$Ph), 3.50 and 3.8 (d, 2H, epoxy), 4.10-4.30 (m, 4H, NCH$_2$ and (α-H), 5.10 (m, 2H, Cbz), 6.10 and 6.25 (m, 2H, NH), 7.20-7.40 (m, 5H, Ph), 9.00 (m, 1H, NH).

Example 3F

Cbz-Asp(O-tBu)-Glu(O-tBu)-Val-AAsp(O-tBu)-(2S,3S)-EP-COOCH$_2$Ph was obtained using the mixed anhydride coupling method, and purified using column chromatography on silica gel using 5:1:19 EtOAc:MeOH:CH$_2$Cl$_2$ as the eluent; white solid, yield 23%. MS (ESI) m/z 940.5 [(M+1)$^+$]. $^1$H NMR (CDCl$_3$): 0.85 (m, 6H, Val), 1.35 (m, 27H, tBu), 1.80-2.24 (m, 3H, Val and Glu), 2.41 (m, 2H, Glu), 2.65-2.90 (m, 2H, Asp), 3.60 and 4.00 (d, 2H, epoxy), 4.05-4.12 (m, 2H, NCH$_2$), 4.10-4.40 (m, 3H, α-H), 5.05 (m, 4H, Cbz), 6.05 (m, 1H, NH), 7.20-7.40 (m, 10H, Ph), 7.85 (m, 2H, NH), 9.05 (m, 1H, NH).

Example 3G

Cbz-Asp(O-tBu)-Glu(O-tBu)-Val-AAsp(O-tBu)-(2S,3S)-EP-CONHCH$_2$Ph was obtained using the mixed anhydride coupling method and was purified using column chromatography on silica gel using 1:2 EtOAc:hexane as the eluent; white solid, yield 31%. MS (ESI) m/z 939.6 [(M+1)$^+$]. $^1$H NMR (CDCl$_3$): 0.97 (m, 6H, Val), 1.40 (m, 27H, tBu), 1.9-2.3 (m, 3H, Val and Glu), 2.41 (m, 2H, Glu), 2.80-2.95 (m, 2H, Asp), 3.63 and 3.97 (d, 2H, epoxy), 4.05-4.22 (m, 4H, NCH$_2$), 4.20-4.55 (m, 3H, α-H), 4.45 (m, 2H, NHCH$_2$Ph), 5.05 (m, 2H, Cbz), 7.20-7.40 (m, 10H, Ph), 6.15 (m, 1H, NH), 6.60 (1H, NH), 7.85 (m, 2H, NH).

Example 3H

Cbz-Glu(O-tBu)-Val-AAsp(O-tBu)-(2S,3S)-EP-COOEt was obtained using the mixed anhydride coupling method and was purified using column chromatography on silica gel with 1:2 EtOAc:hexane as the eluent, and recrystallized from EtOAc/hexane; white solid, yield 44%. MS (ESI) m/z 706.1 [(M+1)$^+$]. $^1$H NMR (DMSO-d$_6$): 0.90 (m, 6H, Val), 1.20 (t, 3H, OCH$_2$CH$_3$), 1.40 (m, 18H, tBu), 1.60-2.00 (m, 3H, Val and Glu), 2.21 (m, 2H, Glu), 3.50 and 3.98 (d, 2H, epoxy), 4.00-4.20 (m, 4H, NCH$_2$ and OCH$_2$CH$_3$), 4.20-4.40 (m, 2H, α-H), 5.05 (m, 2H, Cbz), 7.20-7.40 (m, 5H, Ph), 8.00 (m, 2H, NH).

Example 3I

Cbz-Glu(O-tBu)-Val-AAsp(O-tBu)-(2R,3R)-EP-COOEt was obtained using the mixed anhydride coupling method and was purified using column chromatography on silica gel with 7:13:1:19 hexane:EtOAc:MeOH:CH$_2$Cl$_2$ as the eluent, and then rechromatographed using 3:1 EtOAc:hexane as the eluent; white solid, yield 35%. MS (ESI) m/z 706.1 [(M+1)$^+$]. $^1$H NMR (CDCl$_3$): 0.94 (m, 6H, Val), 1.21 (t, 3H, OCH$_2$CH$_3$), 1.43 (m, 18H, tBu), 1.60-2.00 (m, 3H, Val and Glu), 2.21 (m, 2H, Glu), 3.60 and 3.98 (d, 2H, epoxy), 4.00-4.20 (m, 4H, NCH$_2$ and OCH$_2$CH$_3$), 4.20-4.40 (m, 2H, α-H), 5.10 (m, 2H, Cbz), 7.20-7.40 (m, 5H, Ph), 8.00 (m, 2H, NH).

Example 4

Deblocking of the t-Butyl Group in Aza-Asp Peptides. Epoxysuccinyl peptides (PhPr-Val-Ala-AAsp(O-tBu)-trans-EP-COOCH$_2$Ph), (PhPr-Val-Ala-AAsp(O-tBu)-trans-EP-CH$_2$CH$_2$Ph), (Cbz-Asp-Glu-Val-AAsp(O-tBu)-(2S,3S)-EP-COOEt), (Cbz-Asp-Glu-Val-AAsp(O-tBu)-(2R,3R)-EP-COOEt), (Cbz-Leu-Glu-Thr-AAsp(O-tBu)-(2S,3S)-EP-COOEt), and peptidyl-AAsp(O-tBu)-EP-R$_3$ derivatives all were separately reacted with TFA at 0° C. for 1 h-1.5 hr. The excess TFA was removed under vacuum, and the final products were recrystallized from methanol/ether and ether/hexane to give the final epoxysuccinyl peptides as white solids (yields 59-85%). The products of these reactions are listed in Examples 4A-B.

Example 4A (2S,3S)-3-(N—(N-Benzyloxycarbonylaspartyl-glutamylvalyl)-N-carboxymethylhydrazinocarbonyl)oxirane-2-carboxylic Acid Ethyl Ester (Cbz-Asp-Glu-Val-AAsp-(2S,3S)-EP-COOEt). $^1$H NMR (DMSO-d$_6$): 0.84 (m, 6H, Val), 1.20, 1.21 (t, 3H, OCH$_2$CH$_3$), 1.7-2.1 (m, 3H, Val, Glu), 2.21 (m, 2H, Glu), 2.40-2.65 (m, 2H Asp), 3.58 and 4.10 (d, 2H, epoxy), 4.05-4.22 (m, 4H, NCH$_2$COOH and OCH$_2$CH$_3$), 4.50-4.60 (m, 3H, α-H), 5.05 (m, 2H, Cbz), 7.20-7.40 (m, 5H, Ph), 7.60 (1H, NH), 7.85 (m, 2H, NH), 11.00 (m, COOH). HRMS (FAB) Calcd. for C$_{30}$H$_{39}$N$_5$O$_{15}$: 710.25209. Observed m/z 710.2550. Anal. Calcd. for C$_{30}$H$_{39}$N$_5$O$_{15}$.1.65H$_2$O: C, 48.73; H, 5.76; N, 9.47. Found: C, 48.73; H, 5.63; N, 9.45.

Example 4B (2R,3R)-3-(N'-(N-Benzyloxycarbonylaspartyl-glutamylvalyl)-N'-carboxymethylhydrazinocarbonyl)oxirane-2-carboxylic Acid Ethyl Ester (Cbz-Asp-Glu-Val-AAsp-(2R,3R)-EP-COOEt). $^1$H NMR (DMSO-d$_6$): 0.84 (m, 6H, Val), 1.20, 1.21 (t, 3H, OCH$_2$CH$_3$), 1.7-2.1 (m, 3H, Val, Glu), 2.21 (m, 2H, Glu), 2.40-2.65 (m, 2H Asp), 3.58 and 4.10 (d, 2H, epoxy), 4.05-4.22 (m, 4H, NCH$_2$COOH and OCH$_2$CH$_3$), 4.50-4.60 (m, 3H, α-H), 5.05 (m, 2H, Cbz), 7.20-7.40 (m, 5H, Ph), 7.60 (1H, NH), 7.85 (m, 2H, NH), 11.00 (m, COOH). HRMS (FAB) Calcd. for C$_{30}$H$_{39}$N$_5$O$_{15}$: 710.25209. Observed m/z 710.25195. Anal. Calcd. for C$_{30}$H$_{39}$N$_5$O$_{15}$.0.9H$_2$O: C, 49.64; H, 5.66; N, 9.65. Found: C, 49.59; H, 5.56; N, 9.66.

Example 5

(2S,3S)-3-(N$^2$—(N-Benzyloxycarbonylaspartyl-glutamylvalyl)-N$^1$-carboxymethylhydrazinocarbonyl)oxirane-2-carboxylic Acid Benzyl Ester (Cbz-Asp-Glu-Val-AAsp-(2S,3S)-EP-COOCH$_2$Ph). $^1$H NMR (DMSO-d$_6$): 0.85 (m, 6H, Val), 1.80-2.24 (m, 3H, Val, Glu), 2.41 (m, 2H, Glu), 2.65-2.90 (m, 2H, Asp), 3.60 and 4.00 (d, 2H, epoxy), 4.05-4.12 (m, 2H, NCH$_2$COOH), 4.10-4.40 (m, 3H, α-H), 5.05 (m, 4H, Cbz), 6.05 (m, 1H, NH), 7.20-7.40 (m, 10H, Ph), 7.85 (m, 2H, NH), 9.05 (m, 1H, NH). HRMS (ESI) Calcd. for C$_{47}$H$_{66}$N$_5$O$_{15}$: 940.5. Observed m/z 940.5. Anal. Calcd. for C$_{35}$H$_{41}$N$_5$O$_{15}$.1.5H$_2$O: C, 52.60; H, 5.55; N, 8.76. Found: C, 52.59; H, 5.37; N, 8.76.

Example 6

The peptide ketoamide calpain inhibitor Cbz-Leu-Abu-CONH—(CH$_2$)$_3$-4-morpholinyl (AK295) and the aza-peptide epoxide caspase inhibitor Cbz-Asp-Glu-Val-AAsp-EP-COOEt (JG36) inhibit vincristine-induced nerve degeneration.

Example 6A

Dorsal Root Ganglia (DRG) Cultures. Tissue culture dishes (Falcon) of 35×10 mm were pre-coated with rat tail collagen (type 1, Sigma), air dried and rehydrated with DMEM (GIBCO) overnight at room temperature and then stored at 4° C. On the day of DRG culture, the dishes were washed twice with PBS buffer (pH 7.4), filled with 550 μl medium and pre-incubated at 37° C. for at least 2 hours. Fifteen-day old embryos (E15) were removed from pregnant Sprague-Dawley rats (Charles River), and spinal cords with cervical and thoracic DRGs attached were dissected into L-15 medium (GIBCO). Ganglia were separated from the spinal cord, stripped of their connective tissue sheaths and roots, and then pooled and washed twice with PBS buffer (pH 7.4). DRGs were plated (4 per dish) in culture media and incubated at 37° C. in 5% carbon dioxide for 4 hours to allow DRGs to attach to the substrate. Medium was then added to bring the total volume to 1 mL. Standard media was MEM (GIBCO, free calcium 1.8 mM), supplemented with 1% N$_2$ supplement (GIBCO), 7S NGF (Alomone Labs, Jerusalem, Israel) 100 ng/mL, and 1.4 mM L-glutamine (Sigma). Calcium-free medium was prepared in the same manner, replacing MEM with S-MEM (GIBCO).

Example 6B

Immunostaining of DRGs. At the end of the treatment period (see below) DRGs were fixed for 30 minutes with 4% paraformaldehyde. Cultures were then rinsed with 0.1 M TBS buffer, and treated sequentially with 3% $H_2O_2$, TBS-Triton, and 4% normal goat serum (NGS), each for 30 minutes at room temperature. DRGs were incubated at 4° C. overnight in monoclonal antibody to MAP5 (1:500, Sigma). After washing in TBS-Triton, DRGs were incubated for 60 minutes in biotinylated secondary antibody, rinsed with TBS and reacted with avidin-biotin complex solution (ABC; Vector Labs) for one hour. Color was generated by incubation for 10 minutes in diaminobenzidine (DAB) solution, enhanced by addition of 0.025% cobalt chloride and 0.02% nickel ammonium sulfate. Stained tissue was rinsed, air dried and coverslipped for microscopy with Crystal/Mount (Biomeda).

Example 6C

Vincristine Neuropathy. DRGs were allowed to mature for 5 days (media change on day 3) creating a lush halo of neurites. This method of allowing neuritic extension to proceed before addition of a neurotoxin tests the effect of the toxin on established neurites as opposed to the effect on primary neuritic outgrowth. Thus, the in vitro paradigm is partially comparable to the clinical situation in that an "established" peripheral nervous system is exposed to a toxic agent.

After day 5 of culture, the media was changed to that containing the experimental treatment. This date was defined as treatment day 0. Cultures were monitored and imaged daily using video microscopy. Vincristine sulfate salt (Sigma) was dissolved in culture medium, aliquoted and stored at −20° C. AK295 (the peptide ketoamide calpain inhibitor Cbz-Leu-Abu-CONH—$(CH_2)_3$-4-morpholinyl) or JG36 (the aza-peptide epoxide caspase inhibitor Cbz-Asp-Glu-Val-AAsp-EP-COOEt) was dissolved in 100% DMSO and then diluted to its final concentration with culture medium; the final concentration of DMSO was <0.05%.

After 6 days of treatment (11 days in culture) immunostained DRGs were quantitated for degree of axonal degeneration. Images of the DRGs and neurites were captured onto disk using a computerized video imaging system, and analyzed using NIH Image version 1.61. DRG areas were calculated by tracing the outside circumference of the remaining culture halo. The length of the longest neurite of each DRG was measured from the center of the DRG to the distal end of the neurite, so that cultures without remaining neurites still had positive values. These quantitative data were subjected to ANOVA, with post-test correction for multiple comparisons.

As shown in the table and graph below, both AK295 and JG36 showed significant and equivalent protection against axonal degeneration in the DRG model of vincristine neuropathy. AK295 has also shown protection against Taxol neuropathy in an animal model. These experiments indicate that a combination of a caspase inhibitor and a calpain inhibitor would give signicant protection against peripheral neuropathy induced by toxic anticancer agents.

TABLE XII

Inhibition of nerve degeneration by AK295 and JG36

| TREATMENT | DRG AREA (% day 0) | p-value (vs. vin alone) |
|---|---|---|
| AK295-50 µM | 57.65 +/− 2.97 | 0.0278 |
| JG36-50 µM | 55.53 +/− 2.56 | 0.0411 |
| AK295 + JG36−, both at 50 µM | 51.62 +/− 7.66 | 0.0628 |
| Ak295 + JG36, both at 25 µM | 49.43 +/− 10.31 | 0.2063 |
| Vin alone | 35.96 +/− 7.25 | |
| control | 275.8 +/− 57.91 | |

The above specification and Examples fully disclose how to make and use the compounds of the present disclosure. However, the present disclosure is not limited to the particular embodiments described hereinabove, but includes all modifications thereof within the scope of the following claims. The various references to journals, patents, and other publications which are cited herein comprise the state of the art and are incorporated herein by reference.

---

What is claimed is:

1. A method of alleviation or stabilization of nerve degeneration in a mammal comprising:
administering to a mammal in need thereof a therapeutically effective amount of a compound of the formula:

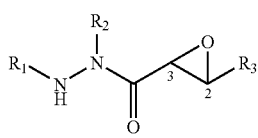

or a pharmaceutically acceptable salt, or prodrug, thereof wherein, $R_1$ is selected from the group consisting of $M_1$, $M_2$-$AA_1$, $M_2$-$AA_2$-$AA_1$, and $M_2$-$AA_3$-$AA_2$-$AA_1$;

$M_1$ is selected from the group consisting of $NH_2$—CO—, $NH_2$—CS—, $NH_2$—$SO_2$—, X—NH—CO—, $X_2$N—CO—, X—NH—CS—, $X_2$N—CS—, X—NH—$SO_2$—, $X_2$N—$SO_2$—, X—CO—, X—CS—, Y—$SO_2$—, Y—O—CO—, Y—O—CS—, phenyl substituted with K, phenyl disubstituted with K, and morpholine-CO—;

$M_2$ is selected from the group consisting of H, $NH_2$—CO—, $NH_2$—CS—, $NH_2$—$SO_2$—, X—NH—CO—, $X_2$N—CO—, X—NH—CS—, $X_2$N—CS—, X—NH—$SO_2$—, $X_2$N—$SO_2$—, X—CO—, X—CS—, Y—$SO_2$—, Y—O—CO—, Y—O—CS—, phenyl, phenyl substituted with K, phenyl disubstituted with K, and morpholine-CO—;

X is selected from the group consisting of H, $C_{1-10}$ alkyl, $C_{3-15}$ cyclized alkyl, $C_{1-10}$ fluoroalkyl, $C_{1-10}$ alkyl substituted with J, $C_{1-10}$ fluoroalkyl substituted with J, 1-admantyl, 9-fluorenyl, phenyl, phenyl substituted with K, phenyl disubstituted with K, phenyl trisubstituted with K, naphthyl, naphthyl substituted with K, naphthyl disubstituted with K, naphthyl trisubstituted with K, $C_{1-10}$ fluoroalkyl with an attached phenyl group, $C_{1-10}$ alkyl with an attached phenyl group, $C_{1-10}$ alkyl with two attached phenyl groups, $C_{1-10}$ alkyl with an attached phenyl group substituted with K, $C_{1-10}$ alkyl with two attached phenyl groups substituted with K, $C_{1-10}$ alkyl with an attached naphthyl group, $C_{1-10}$ alkyl with an attached naphthyl group substituted with K, $C_{1-10}$ alkyl with an attached phenoxy group, biotinyl, and $C_{1-10}$ alkyl with an attached phenoxy group substituted with K on the phenoxy group;

Y is selected from the group consisting of $C_{1-10}$ alkyl, $C_{3-15}$ cyclized alkyl, $C_{1-10}$ fluoroalkyl, $C_{1-10}$ alkyl substituted with J, $C_{1-10}$ fluoroalkyl substituted with J, 1-admantyl, 9-fluorenyl, phenyl, phenyl substituted with K, phenyl disubstituted with K, phenyl trisubstituted with K, naphthyl, naphthyl substituted with K, naphthyl disubstituted with K, naphthyl trisubstituted with K, $C_{1-10}$ fluoroalkyl with an attached phenyl group, $C_{1-10}$ alkyl with an attached phenyl group, $C_{1-10}$ alkyl with two attached phenyl groups, $C_{1-10}$ alkyl with an attached phenyl group substituted with K, $C_{1-10}$ alkyl with two attached phenyl groups substituted with K, $C_{1-10}$ alkyl with an attached naphthyl group, $C_{1-10}$ alkyl with an attached naphthyl group substituted with K, $C_{1-10}$ alkyl with an attached phenoxy group, biotinyl, and $C_{1-10}$ alkyl with an attached phenoxy group substituted with K on the phenoxy group;

J is selected from the group consisting of halogen, $CO_2H$, OH, CN, $NO_2$, $NH_2$, $C_{1-10}$ alkoxy, $C_{1-10}$ alkylamino, $C_{2-12}$ dialkylamino, $C_{1-10}$ alkyl-O—CO—, $C_{1-10}$ alkyl-O—CO—NH—, and $C_{1-10}$ alkyl-S—;

K is selected from the group consisting of halogen, $C_{1-10}$ alkyl, $C_{1-10}$ perfluoroalkyl, $C_{1-10}$ alkoxy, phenoxy, $NO_2$, CN, OH, $CO_2H$, amino, $C_{1-10}$ alkylamino, $C_{2-12}$ dialkylamino, $C_{1-10}$ acyl, and $C_{1-10}$ alkoxy-CO—, and $C_{1-10}$ alkyl-S—;

$AA_1$, $AA_2$, and $AA_3$ are side chain blocked or unblocked amino acids with the L configuration, D configuration, or no chirality at the α-carbon selected from the group consisting of alanine, valine, leucine, isoleucine, proline, methionine, methionine sulfoxide, phenylalanine, tryptophan, glycine, serine, threonine, cysteine, tyrosine, asparagine, glutamine, aspartic acid, glutamic acid, lysine, arginine, histidine, phenylglycine, beta-alanine, norleucine, norvaline, alpha-aminobutanoic acid, epsilon-aminocaproic acid, citrulline, hydroxyproline, ornithine, homoarginine, sarcosine, indoline 2-carboxylic acid, 2-azetidinecarboxylic acid, pipecolinic acid (2-piperidine carboxylic acid), O-methylserine, O-ethylserine, S-methylcysteine, S-ethylcysteine, S-benzylcysteine, $NH_2$—$CH(CH_2CHEt_2)$—$CO_2H$, alpha-aminoheptanoic acid, $NH_2$—$CH(CH_2$-1-naphthyl)-$CO_2H$, $NH_2$—$CH(CH_2$-2-naphthyl)-$CO_2H$, $NH_2$—$CH(CH_2$-cyclohexyl)-$CO_2H$, $NH_2$—$CH(CH_2$-cyclopentyl)-$CO_2H$, $NH_2$—$CH(CH_2$-cyclobutyl)-$CO_2H$, $NH_2$—$CH(CH_2$-cyclopropyl)-$CO_2H$, trifluoroleucine, 4-fluorophenylalanine, lysine substituted on the epsilon nitrogen with a biotinyl group, and hexafluoroleucine;

$R_2$ is selected from the group consisting of $C_{1-10}$ alkyl, $C_{1-10}$ alkyl substituted with Q, $C_{1-10}$ alkyl substituted with phenyl, $C_{1-10}$ alkyl with an attached phenyl substituted with K, $C_{1-10}$ alkyl substituted with naphthyl, $C_{1-10}$ alkyl with an attached naphthyl substituted with K, phenyl, phenyl substituted with K, naphthyl, naphthyl substituted with K, $C_{1-10}$ alkyl substituted with $CONH_2$, $C_{1-10}$ alkyl substituted with $CONHR_4$, $C_{1-10}$ alkyl substituted with $CO_2H$, $C_{1-10}$ alkyl substituted with $CO_2R_4$, $CH_2CH_2SCH_3$, $CH_2$-3-indolyl, $CH_2$-2-thienyl, $CH_2$-2-furyl, $CH_2$-3-furyl, $CH_2$-2-imidazyl, $C_{1-10}$ alkyl substituted with G, $C_{1-10}$ alkyl with an attached phenyl substituted with G, $C_{1-10}$ alkyl with an attached naphthyl substituted with G, phenyl substituted with G, and naphthyl substituted with G;

$R_4$ is selected from the group consisting of $C_{1-10}$ alkyl and $C_{1-10}$ alkyl substituted with phenyl;

Q is selected independently from the group consisting of $C_{1-10}$ alkoxy, $C_{1-10}$ alkyl-S—, $C_{1-10}$ alkoxy substituted with phenyl, and $C_{1-10}$ alkyl-S— substituted with phenyl;

G is selected independently from the group consisting of amidino (—C(=NH)$NH_2$), guanidino (—NHC(=NH)$NH_2$), isothiureido (—S—C(=NH)$NH_2$), amino, $C_{1-6}$ alkylamino, $C_{2-12}$ dialkylamino, and imidazyl;

$R_3$ is selected independently from the group consisting of $R_5$, $CO_2H$, $CO_2R_5$, $CONHR_6$, $CONR_6R_7$, CO-$AA_4$-T,

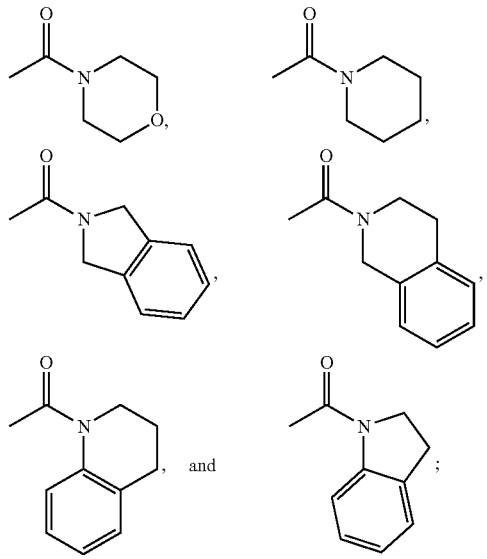

$R_5$ is selected independently from the group consisting of $C_{1-10}$ alkyl, $C_{3-15}$ cyclized alkyl, $C_{1-10}$ alkyl with a phenyl group attached to the $C_{1-10}$ alkyl, $C_{3-15}$ cyclized alkyl with an attached phenyl group, $C_{1-10}$ alkyl with an attached phenyl group substituted with K, $C_{1-10}$ alkyl with an attached phenyl group disubstituted with K, $C_{1-10}$ alkyl with an attached phenyl group trisubstituted with K, $C_{3-15}$ cyclized alkyl with an attached phenyl group substituted with K, $C_{1-10}$ alkyl with a naphthyl group attached to the $C_{1-10}$ alkyl, $C_{3-15}$ cyclized alkyl with an attached naphthyl group, $C_{1-10}$ alkyl with an attached naphthyl group substituted with K, $C_{1-10}$ alkyl with an attached naphthyl group disubstituted with K, $C_{1-10}$ alkyl with an attached naphthyl group trisubstituted with K, and $C_{3-15}$ cyclized alkyl with an attached naphthyl group substituted with K;

T is selected independently from the group consisting of OH, $OR_8$, $NHR_9$, and $NR_8R_9$;

$AA_4$ is a side chain blocked or unblocked amino acid with the L configuration, D configuration, or no chirality at the α-carbon selected from the group consisting of alanine, valine, leucine, isoleucine, proline, methionine, methionine sulfoxide, phenylalanine, tryptophan, glycine, serine, threonine, cysteine, tyrosine, asparagine, glutamine, aspartic acid, glutamic acid, lysine, arginine, histidine, phenylglycine, beta-alanine, norleucine, norvaline, alpha-aminobutanoic acid, epsilon-aminocaproic acid, citrulline, hydroxyproline, ornithine, homoarginine, sarcosine, indoline 2-carboxylic acid, 2-azetidinecarboxylic acid, pipecolinic acid (2-piperidine carboxylic acid), O-methylserine, O-ethylserine, S-methylcysteine, S-ethylcysteine, S-benzylcysteine, $NH_2$—$CH(CH_2CHEt_2)$—$CO_2H$, alpha-aminoheptanoic acid, $NH_2$—$CH(CH_2$-1-naphthyl)-$CO_2H$, $NH_2$—$CH(CH_2$-2-naphthyl)-$CO_2H$, $NH_2$—$CH(CH_2$-cyclohexyl)-$CO_2H$, $NH_2$—$CH(CH_2$-cyclopentyl)-$CO_2H$, $NH_2$—$CH(CH_2$-cyclobutyl)-$CO_2H$, $NH_2$—$CH(CH_2$-cyclopropyl)-$CO_2H$, trifluoroleucine, 4-fluorophenylalanine, lysine substituted on the epsilon nitrogen with a biotinyl group, and hexafluoroleucine;

$R_6$ and $R_7$ are selected independently from the group consisting of H, $C_{1-10}$ alkyl, $C_{3-20}$ cyclized alkyl, $C_{1-10}$ alkyl with a phenyl group attached to the $C_{1-10}$ alkyl, $C_{1-10}$ alkyl with two phenyl groups attached to the $C_{1-10}$ alkyl, $C_{3-20}$ cyclized alkyl with an attached phenyl group, phenyl, phenyl substituted with K, $C_{1-10}$ alkyl with an attached phenyl group substituted with K, $C_{1-10}$ alkyl with an attached phenyl group disubstituted with K, $C_{1-10}$ alkyl with an attached phenyl group trisubstituted with K, $C_{1-10}$ alkyl with two phenyl groups attached to the $C_{1-10}$ alkyl and substituted with K on the phenyl group, $C_{1-10}$ alkyl with two phenyl groups attached to the $C_{1-10}$ alkyl and disubstituted with K on the phenyl groups, $C_{3-20}$ cyclized alkyl with an attached phenyl group substituted with K, $C_{1-10}$ alkyl with a morpholine [—N(CH$_2$CH$_2$)O]ring attached through nitrogen to the alkyl, $C_{1-10}$ alkyl with a piperidine ring attached through nitrogen to the alkyl, $C_{1-10}$ alkyl with a pyrrolidine ring attached through nitrogen to the alkyl, $C_{1-20}$ alkyl with an OH group attached to the alkyl, —CH$_2$CH$_2$CH$_2$OCH$_3$, $C_{1-10}$ alkyl with an attached 4-pyridyl group, $C_{1-10}$ alkyl with an attached 3-pyridyl group, $C_{1-10}$ alkyl with an attached 2-pyridyl group, $C_{1-10}$ alkyl with an attached cyclohexyl group, —NH—CH$_2$CH$_2$-(4-hydroxyphenyl), —NH—CH$_2$CH$_2$-(3-indolyl), $C_{1-10}$ alkyl with an attached 2-furyl group, $C_{1-10}$ alkyl with an attached 3-furyl group, and $C_{1-5}$ alkyl with an attached phenyl and a hydroxyl attached to the $C_{1-5}$ alkyl; and $R_8$ and $R_9$ are selected independently from the group consisting of H, $C_{1-10}$ alkyl, phenyl, nitrophenyl, and $C_{1-10}$ alkyl substituted with phenyl.

2. A method according to claim 1 wherein:

$R_1$ is selected from the group consisting of $M_2$-AA$_1$, $M_2$-AA$_2$-AA$_1$, and $M_2$-AA$_3$-AA$_2$-AA$_1$;

$M_2$ is selected from the group consisting of H, X—CO—, X—NH—CO—, Y—SO$_2$—, and Y—O—CO—;

X is selected from the group consisting of H, $C_{1-10}$ alkyl, $C_{1-10}$ alkyl substituted with J, phenyl, phenyl substituted with K, naphthyl, naphthyl substituted with K, $C_{1-10}$ alkyl with an attached phenyl group, $C_{1-10}$ alkyl with an attached phenyl group substituted with K, $C_{1-10}$ alkyl with an attached naphthyl group, $C_{1-10}$ alkyl with an attached naphthyl group substituted with K, $C_{1-10}$ alkyl with an attached phenoxy group, and $C_{1-10}$ alkyl with an attached phenoxy group substituted with K on the phenoxy group;

Y is selected from the group consisting of $C_{1-10}$ alkyl, $C_{1-10}$ alkyl substituted with J, phenyl, phenyl substituted with K, naphthyl, naphthyl substituted with K, $C_{1-10}$ alkyl with an attached phenyl group, $C_{1-10}$ alkyl with an attached phenyl group substituted with K, $C_{1-10}$ alkyl with an attached naphthyl group, $C_{1-10}$ alkyl with an attached naphthyl group substituted with K, $C_{1-10}$ alkyl with an attached phenoxy group, and $C_{1-10}$ alkyl with an attached phenoxy group substituted with K on the phenoxy group;

J is selected from the group consisting of CO$_2$H, OH, NH$_2$, $C_{1-10}$ alkoxy, $C_{1-10}$ alkylamino, and $C_{1-10}$ alkyl-O—CO—;

K is selected from the group consisting of $C_{1-10}$ alkyl, $C_{1-10}$ perfluoroalkyl, $C_{1-10}$ alkoxy, NO$_2$, CN, OH, CO$_2$H, amino, $C_{1-10}$ alkylamino;

AA$_1$, AA$_2$, and AA$_3$ are side chain blocked or unblocked amino acids with the L configuration, D configuration, or no chirality at the α-carbon selected from the group consisting of alanine, valine, leucine, isoleucine, proline, methionine, methionine sulfoxide, phenylalanine, tryptophan, glycine, serine, threonine, cysteine, tyrosine, asparagine, glutamine, aspartic acid, glutamic acid, lysine, arginine, histidine, phenylglycine, norleucine, norvaline, alpha-aminobutanoic acid, epsilon-aminocaproic acid, ornithine, homoarginine, sarcosine, alpha-aminoheptanoic acid, NH$_2$—CH(CH$_2$-1-naphthyl)-CO$_2$H, NH$_2$—CH(CH$_2$-2-naphthyl)-CO$_2$H, NH$_2$—CH(CH$_2$-cyclohexyl)-CO$_2$H, NH$_2$—CH(CH$_2$-cyclopentyl)-CO$_2$H, NH$_2$—CH(CH$_2$-cyclobutyl)-CO$_2$H, and NH$_2$—CH(CH$_2$-cyclopropyl)-CO$_2$H;

$R_2$ is selected from the group consisting of $C_{1-10}$ alkyl substituted with CONH$_2$, $C_{1-10}$ alkyl substituted with CO$_2$H, and $C_{1-10}$ alkyl substituted with CO$_2$R$_4$;

$R_4$ is selected from the group consisting of $C_{1-10}$ alkyl and $C_{1-10}$ alkyl substituted with phenyl;

$R_3$ is selected independently from the group consisting of $R_5$, CO$_2$H, CO$_2$R$_5$, CONHR$_6$, CONR$_6$R$_7$, and CO-AA$_4$-T;

$R_5$ is selected independently from the group consisting of $C_{1-10}$ alkyl, $C_{1-10}$ alkyl with a phenyl group attached to the $C_{1-10}$ alkyl, $C_{1-10}$ alkyl with an attached phenyl group substituted with K, $C_{1-10}$ alkyl with a naphthyl group attached to the $C_{1-10}$ alkyl, and $C_{1-10}$ alkyl with an attached naphthyl group substituted with K.

AA$_4$ is a side chain blocked or unblocked amino acid with the L configuration, D configuration, or no chirality at the α-carbon selected from the group consisting of alanine, valine, leucine, isoleucine, proline, methionine, methionine sulfoxide, phenylalanine, tryptophan, glycine, serine, threonine, cysteine, tyrosine, asparagine, glutamine, aspartic acid, glutamic acid, lysine, arginine, histidine, phenylglycine, norleucine, norvaline, alpha-aminobutanoic acid, epsilon-aminocaproic acid, ornithine, homoarginine, sarcosine, alpha-aminoheptanoic acid, NH$_2$—CH(CH$_2$-1-naphthyl)-CO$_2$H, NH$_2$—CH(CH$_2$-2-naphthyl)-CO$_2$H, NH$_2$—CH(CH$_2$-cyclohexyl)-CO$_2$H, NH$_2$—CH(CH$_2$-cyclopentyl)-CO$_2$H, NH$_2$—CH(CH$_2$-cyclobutyl)-CO$_2$H, and NH$_2$—CH(CH$_2$-cyclopropyl)-CO$_2$H;

$R_6$ and $R_7$ are selected independently from the group consisting of H, $C_{1-10}$ alkyl, $C_{3-20}$ cyclized alkyl, $C_{1-10}$ alkyl with a phenyl group attached to the $C_{1-10}$ alkyl, $C_{1-10}$ alkyl with two phenyl groups attached to the $C_{1-10}$ alkyl, $C_{3-20}$ cyclized alkyl with an attached phenyl group, phenyl, phenyl substituted with K, $C_{1-10}$ alkyl with an attached phenyl group substituted with K, $C_{1-10}$ alkyl with an attached phenyl group disubstituted with K, $C_{1-10}$ alkyl with an attached phenyl group trisubstituted with K, $C_{1-10}$ alkyl with two phenyl groups attached to the $C_{1-10}$ alkyl, $C_{1-10}$ alkyl with two phenyl groups attached to the $C_{1-10}$ alkyl and substituted with K on the phenyl group, $C_{1-10}$ alkyl with two phenyl groups attached to the $C_{1-10}$ alkyl and disubstituted with K on the phenyl groups, $C_{3-20}$ cyclized alkyl with an attached phenyl group substituted with K, $C_{1-20}$ alkyl with an OH group attached to the alkyl, —CH$_2$CH$_2$CH$_2$OCH$_3$, $C_{1-10}$ alkyl with an attached 4-pyridyl group, $C_{1-10}$ alkyl with an attached 3-pyridyl group, $C_{1-10}$ alkyl with an attached 2-pyridyl group, $C_{1-10}$ alkyl with an attached cyclohexyl group, —NH—CH$_2$CH$_2$-(4-hydroxyphenyl), —NH—CH$_2$CH$_2$-(3-indolyl), $C_{1-10}$ alkyl with an attached 2-furyl group, $C_{1-10}$ alkyl with an attached 3-furyl group, and $C_{1-5}$ alkyl with an attached phenyl and a hydroxyl attached to the $C_{1-5}$ alkyl; and $R_8$ and $R_9$ are selected independently from the group consisting of H, $C_{1-10}$ alkyl, phenyl, nitrophenyl, and $C_{1-10}$ alkyl substituted with phenyl.

3. A method according to claim 2 wherein:

X is selected from the group consisting of H, $C_{1-10}$ alkyl, phenyl, naphthyl, $C_{1-10}$ alkyl with an attached phenyl group, $C_{1-10}$ alkyl with an attached naphthyl group, and $C_{1-10}$ alkyl substituted with $CO_2H$;

$AA_1$, $AA_2$, and $AA_3$ are side chain blocked or unblocked amino acids with the L configuration, D configuration, or no chirality at the α-carbon selected from the group consisting of alanine, valine, leucine, isoleucine, proline, methionine, methionine sulfoxide, phenylalanine, tryptophan, glycine, serine, threonine, cysteine, tyrosine, asparagine, glutamine, aspartic acid, glutamic acid, lysine, arginine, histidine, phenylglycine, norleucine, norvaline, alpha-aminobutanoic acid, epsilon-aminocaproic acid, ornithine, homoarginine, sarcosine, $NH_2$—$CH(CH_2$-1-naphthyl)-$CO_2H$, and $NH_2$—$CH(CH_2$-2-naphthyl)-$CO_2H$;

$R_5$ is selected independently from the group consisting of $C_{1-10}$ alkyl and $C_{1-10}$ alkyl with a phenyl group attached to the $C_{1-10}$ alkyl;

$AA_4$ are side chain blocked or unblocked amino acids with the L configuration, D configuration, or no chirality at the α-carbon selected from the group consisting of alanine, valine, leucine, isoleucine, proline, methionine, methionine sulfoxide, phenylalanine, tryptophan, glycine, serine, threonine, cysteine, tyrosine, asparagine, glutamine, aspartic acid, glutamic acid, lysine, arginine, histidine, phenylglycine, norleucine, norvaline, alpha-aminobutanoic acid, epsilon-aminocaproic acid, citrulline, homoarginine, sarcosine, $NH_2$—$CH(CH_2$-1-naphthyl)-$CO_2H$, and $NH_2$—$CH(CH_2$-2-naphthyl)-$CO_2H$;

$R_6$ and $R_7$ are selected independently from the group consisting of H, $C_{1-10}$ alkyl, $C_{1-10}$ alkyl with a phenyl group attached to the $C_{1-10}$ alkyl, $C_{1-10}$ alkyl with two phenyl groups attached to the $C_{1-10}$ alkyl, phenyl substituted with K, $C_{1-10}$ alkyl with an attached phenyl group substituted with K, $C_{1-10}$ alkyl with an attached phenyl group disubstituted with K, $C_{1-10}$ alkyl with two phenyl groups attached to the $C_{1-10}$ alkyl, $C_{1-10}$ alkyl with two phenyl groups attached to the $C_{1-10}$ alkyl and substituted with K on the phenyl group, $C_{1-10}$ alkyl with two phenyl groups attached to the $C_{1-10}$ alkyl and disubstituted with K on the phenyl groups, $C_{3-20}$ cyclized alkyl with an attached phenyl group substituted with K, $C_{1-20}$ alkyl with an OH group attached to the alkyl, —$CH_2CH_2CH_2OCH_3$, and $C_{1-5}$ alkyl with an attached phenyl and a hydroxyl attached to the $C_{1-5}$ alkyl.

4. A method according to claim 1 wherein:

$R_1$ is selected from the group consisting of $M_2$-$AA_1$, $M_2$-$AA_2$-$AA_1$, and $M_2$-$AA_3$-$AA_2$-$AA_1$;

$M_2$ is selected from the group consisting of H, X—CO—, X—NH—CO—, Y—$SO_2$—, and Y—O—CO—;

X is selected from the group consisting of H, $C_{1-10}$ alkyl, $C_{1-10}$ alkyl substituted with J, phenyl, phenyl substituted with K, naphthyl, naphthyl substituted with K, $C_{1-10}$ alkyl with an attached phenyl group, $C_{1-10}$ alkyl with an attached phenyl group substituted with K, $C_{1-10}$ alkyl with an attached naphthyl group, $C_{1-10}$ alkyl with an attached naphthyl group substituted with K, $C_{1-10}$ alkyl with an attached phenoxy group, and $C_{1-10}$ alkyl with an attached phenoxy group substituted with K on the phenoxy group;

Y is selected from the group consisting of $C_{1-10}$ alkyl, $C_{1-10}$ alkyl substituted with J, phenyl, phenyl substituted with K, naphthyl, naphthyl substituted with K, $C_{1-10}$ alkyl with an attached phenyl group, $C_{1-10}$ alkyl with an attached phenyl group substituted with K, $C_{1-10}$ alkyl with an attached naphthyl group, $C_{1-10}$ alkyl with an attached naphthyl group substituted with K, $C_{1-10}$ alkyl with an attached phenoxy group, and $C_{1-10}$ alkyl with an attached phenoxy group substituted with K on the phenoxy group;

J is selected from the group consisting of $CO_2H$, OH, $NH_2$, $C_{1-10}$ alkoxy, $C_{1-10}$ alkylamino, and $C_{1-10}$ alkyl-O—CO—;

K is selected from the group consisting of $C_{1-10}$ alkyl, $C_{1-10}$ perfluoroalkyl, $C_{1-10}$ alkoxy, $NO_2$, CN, OH, $CO_2H$, amino, $C_{1-10}$ alkylamino;

$AA_1$, $AA_2$, and $AA_3$ are side chain blocked or unblocked amino acids with the L configuration, D configuration, or no chirality at the α-carbon selected from the group consisting of alanine, valine, leucine, isoleucine, proline, methionine, methionine sulfoxide, phenylalanine, tryptophan, glycine, serine, threonine, cysteine, tyrosine, asparagine, glutamine, aspartic acid, glutamic acid, lysine, arginine, histidine, phenylglycine, norleucine, norvaline, alpha-aminobutanoic acid, epsilon-aminocaproic acid, ornithine, homoarginine, sarcosine, alpha-aminoheptanoic acid, $NH_2$—$CH(CH_2$-1-naphthyl)-$CO_2H$, $NH_2$—$CH(CH_2$-2-naphthyl)-$CO_2H$, $NH_2$—$CH(CH_2$-cyclohexyl)-$CO_2H$, $NH_2$—$CH(CH_2$-cyclopentyl)-$CO_2H$, $NH_2$—$CH(CH_2$-cyclobutyl)-$CO_2H$, and $NH_2$—$CH(CH_2$-cyclopropyl)-$CO_2H$;

$R_2$ is selected from the group consisting of $C_{1-10}$ alkyl, $C_{1-10}$ alkyl substituted with Q, $C_{1-10}$ alkyl substituted with phenyl, $C_{1-10}$ alkyl with an attached phenyl substituted with K, $C_{1-10}$ alkyl substituted with naphthyl, $C_{1-10}$ alkyl with an attached naphthyl substituted with K, and phenyl;

$R_3$ is selected independently from the group consisting of $R_5$, $CO_2H$, $CO_2R_5$, $CONHR_6$, $CONR_6R_7$, and CO-$AA_4$-T;

$R_5$ is selected independently from the group consisting of $C_{1-10}$ alkyl, $C_{1-10}$ alkyl with a phenyl group attached to the $C_{1-10}$ alkyl, $C_{1-10}$ alkyl with an attached phenyl group substituted with K, $C_{1-10}$ alkyl with a naphthyl group attached to the $C_{1-10}$ alkyl, and $C_{1-10}$ alkyl with an attached naphthyl group substituted with K.

$AA_4$ is a side chain blocked or unblocked amino acid with the L configuration, D configuration, or no chirality at the α-carbon selected from the group consisting of alanine, valine, leucine, isoleucine, proline, methionine, methionine sulfoxide, phenylalanine, tryptophan, glycine, serine, threonine, cysteine, tyrosine, asparagine, glutamine, aspartic acid, glutamic acid, lysine, arginine, histidine, phenylglycine, norleucine, norvaline, alpha-aminobutanoic acid, epsilon-aminocaproic acid, ornithine, homoarginine, sarcosine, alpha-aminoheptanoic acid, $NH_2$—$CH(CH_2$-1-naphthyl)-$CO_2H$, $NH_2$—$CH(CH_2$-2-naphthyl)-$CO_2H$, $NH_2$—$CH(CH_2$-cyclohexyl)-$CO_2H$, $NH_2$—$CH(CH_2$-cyclopentyl)-$CO_2H$, $NH_2$—$CH(CH_2$-cyclobutyl)-$CO_2H$, and $NH_2$—$CH(CH_2$-cyclopropyl)-$CO_2H$;

$R_6$ and $R_7$ are selected independently from the group consisting of H, $C_{1-10}$ alkyl, $C_{3-20}$ cyclized alkyl, $C_{1-10}$ alkyl with a phenyl group attached to the $C_{1-10}$ alkyl, $C_{1-10}$ alkyl with two phenyl groups attached to the $C_{1-10}$ alkyl, $C_{3-20}$ cyclized alkyl with an attached phenyl group, phenyl, phenyl substituted with K, $C_{1-10}$ alkyl with an attached phenyl group substituted with K, $C_{1-10}$ alkyl with an attached phenyl group disubstituted with K, $C_{1-10}$ alkyl with an attached phenyl group trisubstituted with K, $C_{1-10}$ alkyl with two phenyl groups attached to the $C_{1-10}$ alkyl, $C_{1-10}$ alkyl with two phenyl groups attached to the $C_{1-10}$ alkyl and substituted with K on the phenyl group, $C_{1-10}$ alkyl with two phenyl groups attached to the $C_{1-10}$ alkyl and disubstituted with K on the phenyl groups, $C_{3-20}$ cyclized alkyl with an attached phenyl group substituted with K, $C_{1-20}$ alkyl with an OH group attached to the alkyl, —$CH_2CH_2CH_2OCH_3$, $C_{1-10}$ alkyl with an attached 4-pyridyl group, $C_{1-10}$ alkyl with an attached 3-pyridyl group, $C_{1-10}$ alkyl with an attached 2-pyridyl group, $C_{1-10}$ alkyl with an attached cyclohexyl group, —NH—$CH_2CH_2$-(4-hydroxyphenyl), —NH—$CH_2CH_2$-(3-indolyl), $C_{1-10}$ alkyl with an attached 2-furyl group, $C_{1-10}$ alkyl with an attached 3-furyl group, and $C_{1-5}$ alkyl with an attached phenyl and a hydroxyl attached to the $C_{1-5}$ alkyl; and $R_8$ and $R_9$ are selected independently from the group consisting of H, $C_{1-10}$ alkyl, phenyl, nitrophenyl, and $C_{1-10}$ alkyl substituted with phenyl.

5. A method according to claim 4 wherein:

X is selected from the group consisting of H, $C_{1-10}$ alkyl, phenyl, naphthyl, $C_{1-10}$ alkyl with an attached phenyl group, $C_{1-10}$ alkyl with an attached naphthyl group, and $C_{1-10}$ alkyl substituted with $CO_2H$;

$AA_1$, $AA_2$, and $AA_3$ are side chain blocked or unblocked amino acids with the L configuration, D configuration, or no chirality at the α-carbon selected from the group consisting of alanine, valine, leucine, isoleucine, proline, methionine, methionine sulfoxide, phenylalanine, tryptophan, glycine, serine, threonine, cysteine, tyrosine, asparagine, glutamine, aspartic acid, glutamic acid, lysine, arginine, histidine, phenylglycine, norleucine, norvaline, alpha-aminobutanoic acid, epsilon-aminocaproic acid, ornithine, homoarginine, sarcosine, $NH_2$—$CH(CH_2$-1-naphthyl)-$CO_2H$, and $NH_2$—$CH(CH_2$-2-naphthyl)-$CO_2H$;

$R_5$ is selected independently from the group consisting of $C_{1-10}$ alkyl and $C_{1-10}$ alkyl with a phenyl group attached to the $C_{1-10}$ alkyl;

$AA_4$ are side chain blocked or unblocked amino acids with the L configuration, D configuration, or no chirality at the α-carbon selected from the group consisting of alanine, valine, leucine, isoleucine, proline, methionine, methionine sulfoxide, phenylalanine, tryptophan, glycine, serine, threonine, cysteine, tyrosine, asparagine, glutamine, aspartic acid, glutamic acid, lysine, arginine, histidine, phenylglycine, norleucine, norvaline, alpha-aminobutanoic acid, epsilon-aminocaproic acid, ornithine, homoarginine, sarcosine, $NH_2$—$CH(CH_2$-1-naphthyl)-$CO_2H$, and $NH_2$—$CH(CH_2$-2-naphthyl)-$CO_2H$; and $R_6$ and $R_7$ are selected independently from the group consisting of H, $C_{1-10}$ alkyl, $C_{1-10}$ alkyl with a phenyl group attached to the $C_{1-10}$ alkyl, $C_{1-10}$ alkyl with two phenyl groups attached to the $C_{1-10}$ alkyl, phenyl substituted with K, $C_{1-10}$ alkyl with an attached phenyl group substituted with K, $C_{1-10}$ alkyl with an attached phenyl group disubstituted with K, $C_{1-10}$ alkyl with two phenyl groups attached to the $C_{1-10}$ alkyl, $C_{1-10}$ alkyl with two phenyl groups attached to the $C_{1-10}$ alkyl and substituted with K on the phenyl group, $C_{1-10}$ alkyl with two phenyl groups attached to the $C_{1-10}$ alkyl and disubstituted with K on the phenyl groups, $C_{3-20}$ cyclized alkyl with an attached phenyl group substituted with K, $C_{1-20}$ alkyl with an OH group attached to the alkyl, —$CH_2CH_2CH_2OCH_3$, and $C_{1-5}$ alkyl with an attached phenyl and a hydroxyl attached to the $C_{1-5}$ alkyl.

6. A method according to claim 1 wherein:

$R_1$ is selected from the group consisting of $M_2$-$AA_1$, $M_2$-$AA_2$-$AA_1$, and $M_2$-$AA_3$-$AA_2$-$AA_1$;

$M_2$ is selected from the group consisting of H, X—CO—, X—NH—CO—, Y—$SO_2$—, and Y—O—CO—;

X is selected from the group consisting of H, $C_{1-10}$ alkyl, $C_{1-10}$ alkyl substituted with J, phenyl, phenyl substituted with K, naphthyl, naphthyl substituted with K, $C_{1-10}$ alkyl with an attached phenyl group, $C_{1-10}$ alkyl with an attached phenyl group substituted with K, $C_{1-10}$ alkyl with an attached naphthyl group, $C_{1-10}$ alkyl with an attached naphthyl group substituted with K, $C_{1-10}$ alkyl with an attached phenoxy group, and $C_{1-10}$ alkyl with an attached phenoxy group substituted with K on the phenoxy group;

Y is selected from the group consisting of $C_{1-10}$ alkyl, $C_{1-10}$ alkyl substituted with J, phenyl, phenyl substituted with K, naphthyl, naphthyl substituted with K, $C_{1-10}$ alkyl with an attached phenyl group, $C_{1-10}$ alkyl with an attached phenyl group substituted with K, $C_{1-10}$ alkyl with an attached naphthyl group, $C_{1-10}$ alkyl with an attached naphthyl group substituted with K, $C_{1-10}$ alkyl with an attached phenoxy group, and $C_{1-10}$ alkyl with an attached phenoxy group substituted with K on the phenoxy group;

J is selected from the group consisting of $CO_2H$, OH, $NH_2$, $C_{1-10}$ alkoxy, $C_{1-10}$ alkylamino, and $C_{1-10}$ alkyl-O—CO—;

K is selected from the group consisting of $C_{1-10}$ alkyl, $C_{1-10}$ perfluoroalkyl, $C_{1-10}$ alkoxy, $NO_2$, CN, OH, $CO_2H$, amino, $C_{1-10}$ alkylamino;

$AA_1$, $AA_2$, and $AA_3$ are side chain blocked or unblocked amino acids with the L configuration, D configuration, or no chirality at the α-carbon selected from the group consisting of alanine, valine, leucine, isoleucine, proline, methionine, methionine sulfoxide, phenylalanine, tryptophan, glycine, serine, threonine, cysteine, tyrosine, asparagine, glutamine, aspartic acid, glutamic acid, lysine, arginine, histidine, phenylglycine, norleucine, norvaline, alpha-aminobutanoic acid, epsilon-aminocaproic acid, ornithine, homoarginine, sarcosine, alpha-aminoheptanoic acid, $NH_2$—$CH(CH_2$-1-naphthyl)-$CO_2H$, $NH_2$—$CH(CH_2$-2-naphthyl)-$CO_2H$, $NH_2$—$CH(CH_2$-cyclohexyl)-$CO_2H$, $NH_2$—$CH(CH_2$-cyclopentyl)-$CO_2H$, $NH_2$—$CH(CH_2$-cyclobutyl)-$CO_2H$, and $NH_2$—$CH(CH_2$-cyclopropyl)-$CO_2H$;

$R_2$ is selected from the group consisting of $C_{1-10}$ alkyl substituted with G, $C_{1-10}$ alkyl with an attached phenyl substituted with G, $C_{1-10}$ alkyl with an attached naphthyl substituted with G, phenyl substituted with G, and naphthyl substituted with GU.

G is selected independently from the group consisting of amidino (—C(=NH)$NH_2$), guanidino (—NHC(=NH)$NH_2$), isothiureido (—S—C(=NH)$NH_2$), amino, and $C_{1-6}$ alkylamino;

$R_3$ is selected independently from the group consisting of $R_5$, $CO_2H$, $CO_2R_5$, $CONHR_6$, and $CONR_6R_7$;

$R_5$ is selected independently from the group consisting of $C_{1-10}$ alkyl, $C_{1-10}$ alkyl with a phenyl group attached to the $C_{1-10}$ alkyl, $C_{1-10}$ alkyl with an attached phenyl group substituted with K, $C_{1-10}$ alkyl with a naphthyl group attached to the $C_{1-10}$ alkyl, and $C_{1-10}$ alkyl with an attached naphthyl group substituted with K.

$R_6$ and $R_7$ are selected independently from the group consisting of H, $C_{1-10}$ alkyl, $C_{3-20}$ cyclized alkyl, $C_{1-10}$ alkyl with a phenyl group attached to the $C_{1-10}$ alkyl, $C_{1-10}$ alkyl with two phenyl groups attached to the $C_{1-10}$ alkyl, $C_{3-20}$ cyclized alkyl with an attached phenyl group, phenyl, phenyl substituted with K, $C_{1-10}$ alkyl with an attached phenyl group substituted with K, $C_{1-10}$ alkyl with an attached phenyl group disubstituted with K, $C_{1-10}$ alkyl with an attached phenyl group trisubstituted with K, $C_{1-10}$ alkyl with two phenyl groups attached to the $C_{1-10}$ alkyl, $C_{1-10}$ alkyl with two phenyl groups attached to the $C_{1-10}$ alkyl and substituted with K on the phenyl group, $C_{1-10}$ alkyl with two phenyl groups attached to the $C_{1-10}$ alkyl and disubstituted with K on the phenyl groups, $C_{3-20}$ cyclized alkyl with an attached phenyl group substituted with K, $C_{1-20}$ alkyl with an OH group attached to the alkyl, —$CH_2CH_2CH_2OCH_3$, $C_{1-10}$ alkyl with an attached 4-pyridyl group, $C_{1-10}$ alkyl with an attached 3-pyridyl group, $C_{1-10}$ alkyl with an attached 2-pyridyl group, $C_{1-10}$ alkyl with an attached cyclohexyl group, —NH—$CH_2CH_2$-(4-hydroxyphenyl), —NH—$CH_2CH_2$-(3-indolyl), $C_{1-10}$ alkyl with an attached 2-furyl group, $C_{1-10}$ alkyl with an attached 3-furyl group, and $C_{1-5}$ alkyl with an attached phenyl and a hydroxyl attached to the $C_{1-5}$ alkyl; and $R_8$ and $R_9$ are selected independently from the group consisting of H, $C_{1-10}$ alkyl, phenyl, nitrophenyl, and $C_{1-10}$ alkyl substituted with phenyl.

7. A method according to claim 5 wherein:

X is selected from the group consisting of H, $C_{1-10}$ alkyl, phenyl, naphthyl, $C_{1-10}$ alkyl with an attached phenyl group, $C_{1-10}$ alkyl with an attached naphthyl group, and $C_{1-10}$ alkyl substituted with $CO_2H$;

$AA_1$, $AA_2$, and $AA_3$ are side chain blocked or unblocked amino acids with the L configuration, D configuration, or no chirality at the α-carbon selected from the group consisting of alanine, valine, leucine, isoleucine, proline, methionine, methionine sulfoxide, phenylalanine, tryptophan, glycine, serine, threonine, cysteine, tyrosine, asparagine, glutamine, aspartic acid, glutamic acid, lysine, arginine, histidine, phenylglycine, norleucine, norvaline, alpha-aminobutanoic acid, epsilon-aminocaproic acid, ornithine, homoarginine, sarcosine, $NH_2$—$CH(CH_2$-1-naphthyl)-$CO_2H$, and $NH_2$—CH($CH_2$-2-naphthyl)-$CO_2H$;

$R_5$ is selected independently from the group consisting of $C_{1-10}$ alkyl and $C_{1-10}$ alkyl with a phenyl group attached to the $C_{1-10}$ alkyl;

$AA_4$ are side chain blocked or unblocked amino acids with the L configuration, D configuration, or no chirality at the α-carbon selected from the group consisting of alanine, valine, leucine, isoleucine, proline, methionine, methionine sulfoxide, phenylalanine, tryptophan, glycine, serine, threonine, cysteine, tyrosine, asparagine, glutamine, aspartic acid, glutamic acid, lysine, arginine, histidine, phenylglycine, norleucine, norvaline, alpha-aminobutanoic acid, epsilon-aminocaproic acid, ornithine, homoarginine, sarcosine, $NH_2$—CH($CH_2$-1-naphthyl)-$CO_2H$, and $NH_2$—CH($CH_2$-2-naphthyl)-$CO_2H$; and $R_6$ and $R_7$ are selected independently from the group consisting of H, $C_{1-10}$ alkyl, $C_{1-10}$ alkyl with a phenyl group attached to the $C_{1-10}$ alkyl, $C_{1-10}$ alkyl with two phenyl groups attached to the $C_{1-10}$ alkyl, phenyl substituted with K, $C_{1-10}$ alkyl with an attached phenyl group substituted with K, $C_{1-10}$ alkyl with an attached phenyl group disubstituted with K, $C_{1-10}$ alkyl with two phenyl groups attached to the $C_{1-10}$ alkyl, $C_{1-10}$ alkyl with two phenyl groups attached to the $C_{1-10}$ alkyl and substituted with K on the phenyl group, $C_{1-10}$ alkyl with two phenyl groups attached to the $C_{1-10}$ alkyl and disubstituted with K on the phenyl groups, $C_{3-20}$ cyclized alkyl with an attached phenyl group substituted with K, $C_{1-20}$ alkyl with an OH group attached to the alkyl, —$CH_2CH_2CH_2OCH_3$, and $C_{1-5}$ alkyl with an attached phenyl and a hydroxyl attached to the $C_{1-5}$ alkyl.

8. The method of claim 1 wherein epoxide carbons 2 and 3 have stereochemistry selected from the group consisting of cis; trans; R,R; S,S; R,S; and S,R.

9. The method of claim 1, wherein said composition is substantially optically pure.

10. The method of claim 1, wherien said composition is racemic.

11. The method of claim 9, wherein said composition substantially comprises a single optical isomer.

12. A method of alleviation or stabilization of nerve degeneration in a mammal, wherein the nerve degeneration results from one or more of the following conditions: the presence of metabolic derangements, diabetes, uremia, central or peripheral ischemia, genetic susceptibility to nerve degeneration, and exposure to a neurotic agent, comprising:

administering to a mammal a threpeutically effective amount of a compound selected from the group consisting of:

(a) Cbz-Ala-Ala-NHN($CH_2$COOEt)-(trans)-EP-COOEt,
(b) PhPr-Val-Ala-AAsp-(2R,3R)-EP-COO$CH_2$Ph,
(c) PhPr-Val-Ala-AAsp-(2S,3S)-EP-COO$CH_2$Ph,
(d) PhPr-Val-Ala-AAsp-(trans)-EP-COO$CH_2$Ph,
(e) PhPr-Val-Ala-AAsp-(trans)-EP-$CH_2CH_2$Ph,
(f) Cbz-Ile-Glu-Thr-AAsp-(2S,3S)-EP-COOEt,
(g) Cbz-Ile-Glu-Thr-AAsp-(2R,3R)-EP-COOEt,
(h) Cbz-Leu-Glu-Thr-AAsp-(2S,3S)-EP-COOEt,
(i) Cbz-Leu-Glu-Thr-AAsp-(2R,3R)-EP-COOEt,
(j) Cbz-Asp-Glu-Val-AAsp-(2S,3S)-EP-COOEt,
(k) Cbz-Asp-Glu-Val-AAsp-(2R,3R)-EP-COOEt,
(l) Cbz-Glu-Val-AAsp-(2S,3S)-EP-COOEt,
(m) PhPr-Val-Ala-AAsp-(2S,3S)-EP-CON($CH_2CH_2CH_2CH_3$)$_2$,
(n) PhPr-Val-Ala-AAsp-(2S,3S)-EP-CON($CH_2$Ph)$_2$,
(o) Cbz-Leu-Glu-Thr-AAsp-(2S,3S)-EP-CON($CH_2$Ph)$_2$,
(p) Cbz-Ile-Glu-Thr-AAsp-(2S,3S)-EP-CON($CH_2$Ph)$_2$,
(q) Cbz-Leu-Glu-Thr-AAsp-(2S,3S)-EP-CON($CH_3$)$CH_2$Ph,
(r) PhPr-Val-Ala-AAsp-(2S,3S)-EP-CON($CH_3$)$CH_2$Ph,
(s) Cbz-Ile-Glu-Thr-AAsp-(2S,3S)-EP-CON($CH_3$)$CH_2$Ph,
(t) Cbz-Val-AAsp-(S,S)-EP-COOEt,
(u) Cbz-Val-AAsp-(S,S)-EP-COOH,
(v) Cbz-Val-AAsp-(trans)-EP-$CH_2CH_2$Ph,
(w) Cbz-Val-AAsp-(trans)-EP-Ph-4-Cl,
(x) PhPr-Val-Ala-AAsp-(S,S)-EP-COOEt,
(y) PhPr-Val-Ala-AAsp-(R,R)-EP-COOEt,
(z) PhPr-Val-Ala-AAsp-(S,S)-EP-COO$CH_2CH_2$Ph,
(aa) PhPr-Val-Ala-AAsp-(S,S)-EP-CONH$CH_2CH_3$,
(bb) PhPr-Val-Ala-AAsp-(S,S)-EP-CONH$CH_2$Ph,
(cc) PhPr-Val-Ala-AAsp-(R,R)-EP-CONH$CH_2$Ph,
(dd) PhPr-Val-Ala-AAsp-(S,S)-EP-CONH$CH_2CH_2$Ph,
(ee) PhPr-Val-Ala-AAsp-(R,R)-EP-CONH$CH_2CH_2$Ph,
(ff) PhPr-Val-Ala-AAsp-(S,S)-EP-CONH$CH_2$CH(OH)Ph,
(gg) PhPr-Val-Ala-AAsp-(R,R)-EP-CONH$CH_2$CH(OH)Ph,
(hh) PhPr-Val-Ala-AAsp-(S,S)-EP-CO-Ala-NH$CH_2$Ph,
(ii) PhPr-Val-Ala-AAsp-(R,R)-EP-CO-Ala-NH$CH_2$Ph,
(jj) PhPr-Val-Ala-AAsp-(S,S)-EP-CO-Leu-$NH_2$,
(kk) PhPr-Val-Ala-AAsp-(R,R)-EP-CO-Leu-N—$H_2$, (ll) PhPr-Val-Ala-AAsp-(S,S)-EP-CO-Phe-NH$_2$,
(mm) PhPr-Val-Ala-AAsp-(R,R)-EP-CO-Phe-NH$_2$,
(nn) PhPr-Val-Ala-AAsp-(S,S)-EP-CO-Tyr-NH$_2$,
(oo) Cbz-Glu-Val-AAsp-(R,R)-EP-CO-Phe-NH$_2$,
(pp) Cbz-Glu-Val-AAsp-(S,S)-EP-CONHCH$_2$CH$_2$Ph,
(qq) Cbz-Asp-Glu-Val-AAsp-(S,S)-EP-CO-Phe-NH$_2$,
(rr) Cbz-Asp-Glu-Val-AAsp-(S,S)-EP-CONHCH$_2$Ph,
(ss) Cbz-Asp-Glu-Val-AAsp-(S,S)-EP-COOCH$_2$Ph,
(tt) Cbz-Leu-Glu-Thr-AAsp-(S,S)-EP-CONHCH$_2$CH$_2$Ph,
(uu) Cbz-Leu-Glu-Thr-AAsp-(S,S)-EP-CO-Ala-NHCH$_2$Ph,
(vv) Cbz-Ile-Glu-Thr-AAsp-(S,S)-EP-CO-Ala-NHCH$_2$Ph, (ww)
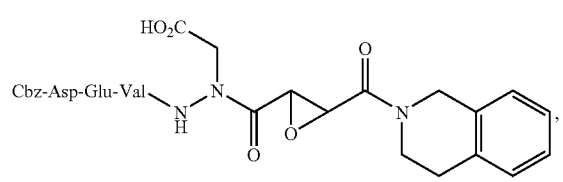

(xx)
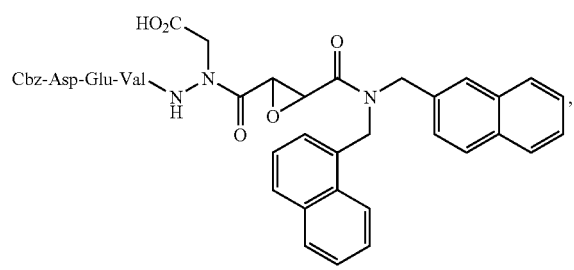

(yy)
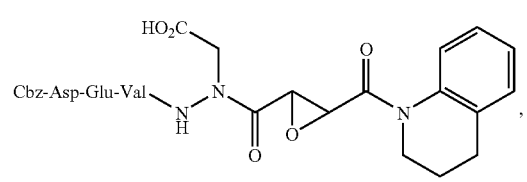

(zz)
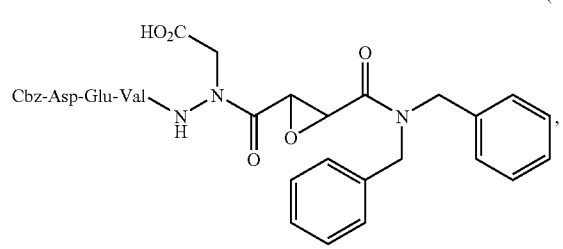

(aaa)
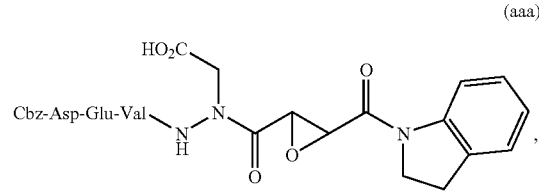

(bbb)
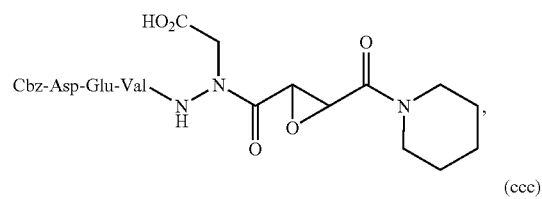

(ccc)
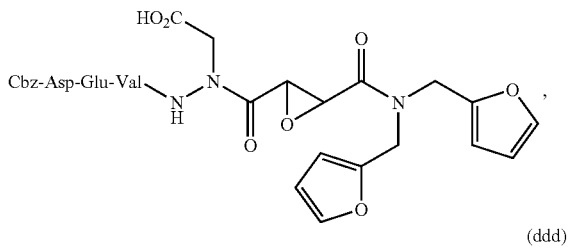

(ddd)
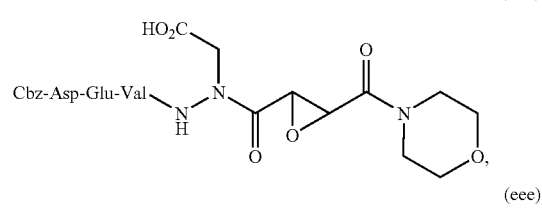

(eee)
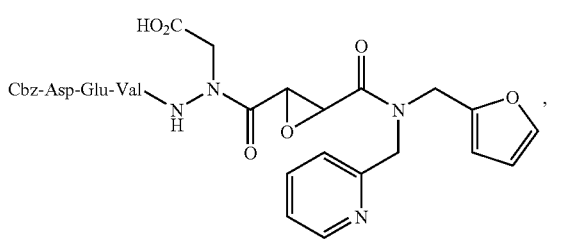

(fff)
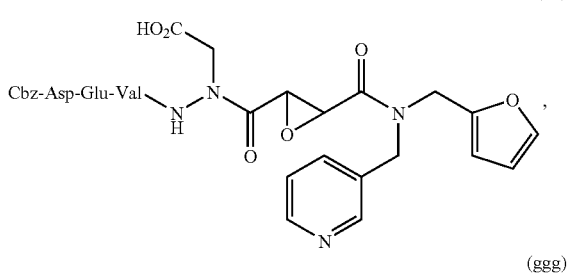

(ggg)
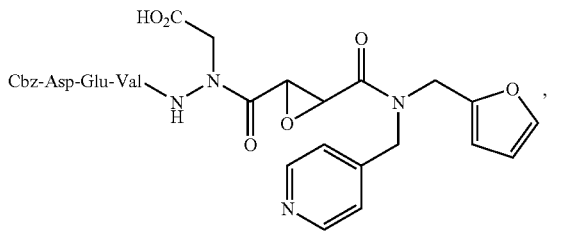

(hhh) Cbz-Leu-Glu-Thr-AAsp-(S,S)-EP-COOCH$_2$Ph,
(iii) Cbz-Ile-Glu-Thr-AAsp-(S,S)-EP-COOCH$_2$Ph,
(jjj) Cbz-Ile-Glu-Thr-AAsp-(R,R)-EP-COOCH$_2$Ph,
(kkk) Cbz-Ile-Glu-Thr-AAsp-(R,R)-EP-CONHCH$_2$Ph,
and a pharmaceutically acceptable salt thereof.

13. A method of alleviation or stabilization of nerve degeneration in a mammal wherein the nerve degeneration results from one or more of the following conditions: the presence of metabolic derangements, diabetes, uremia, central or peripheral ischemia, genetic susceptibility to nerve degeneration, and exposure to a neurotoxic agent, comprising:
administering to a mammal a therapeutically effective amount of a compound having the chemical formula Cbz-Asp-Glu-Val-AAsp-EP-COOEt.

14. A method of treatment of nerve degeneration in a mammal wherein the nerve degeneration results from one or more of the following conditions: the presence of metabolic derangements, diabetes, uremia, central or peripheral ischemia, genetic susceptibility to nerve degeneration, and exposure to a neurotoxic agent, comprising:
administering to a mammal a therapeutically effective amount of a compound having the chemical formula Cbz-Asp-Glu-Val-AAsp-EP-COOCH$_2$C$_6$H$_5$.

15. The method of claim 1 wherein said nerve degeneration results from one or more of the following conditions: stroke, Alzheimer's disease, Parkinson's disease, multiple sclerosis, neuropathies, Huntington's disease, dentatorubropallidoluysian atrophy, spinocerebellar atrophy, spinal bulbar muscular atrophy, nerve degeneration associated with diabetes, nerve degeneration associated with uremia, nerve degeneration associated with a metabolic derangement, amyotrophic lateral sclerosis, a motor neuron disease, genetic susceptibility to nerve degeneration, and exposure to a neurotoxic agent.

16. The method of claim 1, wherein said nerve degeneration is selected from the group consisting of chronic degeneration of motor and or sensory neurons, idiopathic peripheral neuropathies, peripheral neuropathies due to genetic mutations, peripheral neuropathies associated with diabetes, uremia, rheumatologic diseases, liver diseases, or infections, axonal degeneration secondary to primary demyelinating disorders, inflammatory demyelinating neuropathies, multiple sclerosis, and chronic spinal cord degenerations.

17. The method of claim 1 wherein said nerve degeneration is the result of a neurotoxic agent.

18. The method of claim 1, wherein the nerve degeneration is induced by an anti-cancer agent.

19. The method of claim 17 wherein said neurotoxic agent comprises an agent causing microtubule stabilization or disruption.

20. The method of claim 19, wherein said microtubule stabilizing agent comprises paclitaxel.

21. The method of claim 1 wherein said nerve degeneration is inhibited by administration of the compound of claim 1 prior to or simultaneous with administration of an anticancer drug.

22. The method of claim 1, further comprising administering a therapeutically effective amount of a calpain inhibitor to the patient.

23. The method of claim 22 wherein said calpain inhibitor comprises a peptide alpha-keto amide.

24. The method of claim 22 wherein said calpain inhibitor is Z-Leu-Abu-CONH-(CH$_2$)$_3$-4-morpholinyl (AK295).

25. The method of claim 22 wherein said calpain inhibitor is selected from the group consisting of:
Z-Leu-Nva-CONHCH$_2$-2-pyridyl,
Z-Leu-Abu-CONHCH$_2$CH(OH)C$_6$F$_5$,
Z-Leu-Phe-CONH(CH$_2$)$_2$Ph,
Z-Leu-Abu-CONHCH$_2$CH(OH)C$_6$H$_4$-3-OC$_6$H$_4$(3-CF$_3$),
Z-Leu-Abu-CONHCH$_2$CH(OH)C$_6$H$_4$(4-OCH$_2$Ph),
Z-Leu-Abu-CONHCH$_2$CH(OH)C$_6$H$_4$(4-OPh),
Z-Leu-Phe-CONHCH$_2$-2-quinolinyl,
Z-Leu-Abu-CONH(CH$_2$)$_2$C$_6$H$_4$(3-OCH3),
Z-Leu-Abu-CONH(CH$_2$)$_2$C$_6$H$_4$(4-OCH3),
Z-Leu-Abu-CONHCH$_2$CH(OH)-1-C$_{10}$H$_7$,
Z-Leu-Phe-CONH(CH$_2$)$_3$-4-morpholinyl,
Z-Leu-Abu-CONH(CH$_2$)$_2$C$_6$H$_4$(2-OCH$_3$),
Z-Leu-Abu-CONHCH$_2$-2-quinolinyl,
Z-Leu-Abu-CONH(CH$_2$)$_3$-4-morpholinyl (AK295),
Z-Leu-Abu-CONH(CH$_2$)$_2$-2-(N-methylpyrrole),
Z-Leu-Phe-CONHCH$_2$CH(OH)C$_6$H$_4$-3-OC$_6$H$_4$(3-CF$_3$),
Z-Leu-Abu-CONH(CH$_2$)$_2$C$_6$H$_5$,
Z-Leu-Phe-CONH-Et,
Z-Leu-Abu-CONHCH$_2$CH(OC$_2$H$_5$)$_2$,
Z-Leu-Phe-CONHCH$_2$CH(OH)C$_6$H$_4$(4-OPh),
Z-Leu-Phe-CONHCH$_2$CH(OH)C$_6$H$_4$(4-OCH$_2$Ph),
Z-Leu-Abu-CONHCH$_2$C$_6$H$_5$,
Z-Leu-Phe-CONH(CH$_2$)$_2$NH-biotinyl,
Z-Leu-Phe-CONH(CH$_2$)$_3$-2-tetrahydroisoquinolinyl,
Z-Leu-Abu-CONHCH$_2$CH(OH)C$_6$H$_3$(3,4-(OCH$_2$Ph)$_2$),
Z-Leu-Abu-CONHCH$_2$CH(OH)C$_6$H$_4$(4-OCH$_3$),
Z-Leu-Nva-CONH(CH$_2$)$_3$-4-morpholinyl,
Z-Leu-Abu-CONHCH$_2$-1-isoquinolinyl,
Z-Leu-Abu-CONHEt,
Z-Leu-Abu-CONHCH$_2$CH(OH)C$_6$H$_4$-3-OC$_6$H$_3$(3,4-Cl$_2$),
Z-Leu-Abu-CONHMe,
Z-Leu-Abu-CONH(CH$_2$)$_3$-1-imidazolyl,
Z-Leu-Abu-CONH(CH$_2$)$_2$-3-indolyl,
Z-Leu-Abu-CONH(CH$_2$)$_3$-2-tetrahydroisoquinolinyl,
Z-Leu-Abu-CONHCH$_2$-2-tetrahydrofuryl,
Z-Leu-Abu-CONHCH$_2$CH(OH)C$_6$H$_4$(4-N(CH$_3$)$_2$),
Z-Leu-Phe-CONH-n-Pr,
Z-Leu-Abu-CONHCH$_2$CH(OH)-2-C$_{10}$H$_7$,
Z-Leu-Phe-CONH-Me,
Z-Leu-Abu-CON HCH$_2$CH(OH)C$_6$H$_4$(3-CF$_3$),
Z-Leu-Abu-CONH(CH$_2$)$_3$-1-tetrahydroquinolinyl,
Z-Leu-Abu-CON H(CH$_2$)$_2$C$_6$H$_4$(4-OH),
Z-Leu-Abu-CONHCH$_2$CH(OH)C$_6$H$_2$(3,4,5-(OCH$_3$)$_3$),
Z-Leu-Phe-CONH(CH$_2$)$_3$-1-tetrahydroquinolinyl,
Z-Leu-Abu-CONH(CH$_2$)$_2$-2-pyridyl,
Z-Leu-Abu-CONHCH$_2$—C$_6$H$_7$(1,3,3-(CH$_3$)$_3$-5-OH),
Z-Leu-Phe-CONHCH$_2$CH(OH)C$_6$H$_4$(3-CF3),
Z-Leu-Phe-CONHCH$_2$CH(OH)C$_6$H$_3$(3,4-(OCH$_2$Ph)$_2$),
Z-Leu-Abu-CONH(CH$_2$)$_5$OH,
Z-Leu-Abu-CONHCH$_2$CH(OCH$_3$)$_2$,
Z-Leu-Phe-CONHCH$_2$CH(OH)C$_6$H$_4$-3-OC$_6$H$_3$(3,4-Cl$_2$),
Z-Leu-Phe-CONHCH$_2$CH(OH)C$_6$H$_4$(3-OPh),
Z-Leu-Phe-CONHCH$_2$CH(OH)C$_6$H$_4$(4-N(CH$_3$)$_2$),
Z-Leu-Abu-CONHCH$_2$-2-pyridyl,
Z-Leu-Abu-CONH(CH$_2$)$_2$O(CH$_2$)$_2$OH,
Z-Leu-Phe-CONHCH$_2$-2-pyridyl,
Z-Leu-Abu-CONH(CH$_2$)$_2$NH-biotinyl,
Z-Leu-Abu-CONHCH$_2$-C$_6$H$_{11}$,
Z-Leu-Phe-CONHCH$_2$CH(OH)C$_6$F$_5$,
Z-Leu-Abu-CONHCH$_2$-2-furyl,
Z-Leu-Abu-CONH(CH$_2$)$_3$C$_6$H$_5$,
Z-Leu-Abu-CONH(CH$_2$)$_2$OH,
Z-Leu-Abu-CONHCH$_2$CH(OH)C$_6$H$_4$(3-OPh),
Z-Leu-Abu-CONH(CH$_2$)$_2$-4-morpholinyl,
Z-Leu-Abu-CONHCH$_2$CH(OH)Ph,
Z-Leu-Abu-CONHCH$_2$-4-pyridyl,
Z-Leu-Abu-CONH(CH$_2$)$_3$-1-pyrrolidine-2-one,
Z-Leu-Phe-CONHCH$_2$CH(OH)Ph,
Z-Leu-Abu-CONHCH$_2$C$_6$H$_3$(3,5-(OCH$_3$)$_2$),
Z-Leu-Nva-CONHCH$_2$CH(OH)Ph,
Z-Leu-Abu-CONHCH$_2$-8-caffeinyl,
Z-Leu-Abu-n-Pr,
Z-Leu-Abu-CONHCH$_2$-3-pyridyl, and
Z-Leu-Phe-CONHCH$_2$Ph.

26. The method of claim 22 wherein said calpain inhibitor is selected from the group with the formula:

$M^1$-$AA^2$-$AA^1$-CO—$NR_3R_4$ a pharmaceutically acceptable salt or prodrug thereof, wherein $M^1$ is selected from the group consisting of H, $NH_2$—CO—, $NH_2$—CS—, $NH_2$—$SO_2$—, X—NH—CO—, $X_2$N—CO—, X—NH—CS—, $X_2$N—CS—, X—NH—$SO_2$—, $X_2$N—$SO_2$—, X—CO—, X—CS—, X—, Y—$SO_2$—, Y—O—CO—, Y—O—CS—, morpholine-CO—, and biotinyl;

X is selected from the group consisting of H, $C_{1-10}$ alkyl, $C_{3-15}$ cyclized alkyl, $C_{1-10}$ fluoroalkyl, $C_{1-10}$ alkyl substituted with J, $C_{1-10}$ fluoroalkyl substituted with J, 1-adamantyl, 9-fluorenyl, phenyl, phenyl monosubstituted with K, phenyl disubstituted with K, phenyl trisubstituted with K, naphthyl, naphthyl monosubstituted with K, naphthyl disubstituted with K, naphthyl trisubstituted with K, $C_{1-10}$ fluoroalkyl with an attached phenyl group, $C_{1-10}$ alkyl with an attached phenyl group, $C_{1-10}$ alkyl with two attached phenyl groups, $C_{1-10}$ alkyl with an attached phenyl group substituted with K, $C_{1-10}$ alkyl with two attached phenyl groups substituted with K, $C_{1-10}$ alkyl with an attached naphthyl group, $C_{1-10}$ alkyl with an attached naphthyl group substituted with K, $C_{1-10}$ alkyl with an attached phenoxy group, and $C_{1-10}$ alkyl with an attached phenoxy group substituted with K on the phenoxy group, and $C_{1-10}$ alkyl monosubstituted with $M^2$;

Y is selected from the group consisting of $C_{1-10}$ alkyl, $C_{3-15}$ cyclized alkyl, $C_{1-10}$ fluoroalkyl, $C_{1-10}$ alkyl substituted with J, $C_{1-10}$ fluoroalkyl substituted with J, 1-admantyl, 9-fluorenyl, phenyl, phenyl monosubstituted with K, phenyl disubstituted with K, phenyl trisubstituted with K, naphthyl, naphthyl monosubstituted with K, naphthyl disubstituted with K, naphthyl trisubstituted with K, $C_{1-10}$ fluoroalkyl with an attached phenyl group, $C_{1-10}$ alkyl with an attached phenyl group, $C_{1-10}$ alkyl with two attached phenyl groups, $C_{1-10}$ alkyl with an attached phenyl group substituted with K, $C_{1-10}$ alkyl with two attached phenyl groups substituted with K, $C_{1-10}$ alkyl with an attached naphthyl group, $C_{1-10}$ alkyl with an attached naphthyl group substituted with K, $C_{1-10}$ alkyl with an attached phenoxy group, and $C_{1-10}$ alkyl with an attached phenoxy group substituted with K on the phenoxy group, $M^2$, and $C_{1-10}$ alkyl monosubstituted with $M^2$;

$M^2$ is selected from the group consisting of 2-furyl, 2-tetrahydrofuryl, 2-pyridyl, 3-pyridyl, 4-pyridyl, 2-pyrazinyl, 2-quinolinyl, 1-tetrahydroquinolinyl, 1-isoquinolinyl, 2-tetrahydroisoquinolinyl, and —N($CH_2CH_2$)$_2$O;

J is selected from the group consisting of halogen, $CO_2$H, OH, CN, $NO_2$, $NH_2$, $C_{1-10}$ alkoxy, $C_{1-10}$ alkylamino, $C_{2-12}$ dialkylamino, $C_{1-10}$ alkyl-O—CO—, $C_{1-10}$ alkyl-O—CO—NH—, $C_{1-10}$ alkyl-S—, and —N($CH_2CH_2$)$_2$O;

K is selected from the group consisting of halogen, $C_{1-10}$ alkyl, $C_{1-10}$ perfluoroalkyl, $C_{1-10}$ alkoxy, phenoxy, $NO_2$, CN, OH, $CO_2$H, amino, $C_{1-10}$ alkylamino, $C_{2-12}$ dialkylamino, $C_{1-10}$ acyl, and $C_{1-10}$ alkoxy-CO—, and $C_{1-10}$ alkyl-S—, and —N($CH_2CH_2$)$_2$O;

$AA^1$ and $AA^2$ side chain blocked or unblocked amino acids with the L configuration, D configuration, or no chirality at the α-carbon selected from the group consisting of alanine, valine, leucine, isoleucine, pro line, methionine, methionine sulfoxide, phenylalanine, tryptophan, glycine, serine, threonine, cysteine, tyrosine, asparagine, glutamine, aspartic acid, glutamic acid, lysine, arginine, histidine, phenylglycine, beta-alanine, norleucine, norvaline, alpha-aminobutanoic acid, epsilon-aminocaproic acid, citrulline, hydroxyproline, ornithine, homoarginine, sarcosine, indoline 2-carboxylic acid, 2-azetidinecarboxylic acid, pipecolinic acid (2-piperidine carboxylic acid), O-methylserine, O-ethylserine, S-methylcysteine, S-ethylcysteine, S-benzylcysteine, $NH_2$—CH($CH_2CHEt_2$)—$CO_2$H, alpha-aminoheptanoic acid, $NH_2$—CH($CH_2$-1-naphthyl)-$CO_2$H, $NH_2$—CH($CH_2$-2-naphthyl)-$CO_2$H, $NH_2$—CH($CH_2$-cyclohexyl)-$CO_2$H, $NH_2$—CH($CH_2$-cyclopentyl)-$CO_2$H, $NH_2$—CH($CH_2$-cyclobutyl)-$CO_2$H, $NH_2$—CH($CH_2$-cyclopropyl)-$CO_2$H, trifluoroleucine, 4-fluorophenylalanine, lysine substituted on the epsilon nitrogen with a biotinyl group, hexafluoroleucine, and $NH_2$—$CHR^2$—$CO_2$H;

$R^2$ is selected from the group consisting of $C_{1-10}$ branched and unbranched alkyl, $C_{1-10}$ branched and unbranched cyclized alkyl, and $C_{1-10}$ branched and unbranched fluoroalkyl;

$R^3$ and $R^4$ are selected independently from the group consisting of a) $H_{1-20}$ alkyl, $C_{1-20}$ cyclized alkyl, $C_{1-20}$ alkyl with a phenyl group attached to the $C_{1-20}$ alkyl, $C_{1-20}$ cyclized alkyl with an attached phenyl group, $C_{1-20}$ alkyl with an attached phenyl group monosubstituted with K, $C_{1-20}$ alkyl with an attached phenyl group disubstituted with K, $C_{1-20}$ alkyl with an attached phenyl group trisubstituted with K, $C_{1-20}$ cyclized alkyl with an attached phenyl group monosubstituted with K, $C_{1-10}$ alkyl with a morpholine [—N($CH_2CH_2$)O] ring attached through nitrogen to the alkyl, $C_{1-10}$ alkyl with a piperidine ring attached through nitrogen to the alkyl, $C_{1-10}$ alkyl with a pyrrolidine ring attached through nitrogen to the alkyl, $C_{1-20}$ alkyl with an OH group attached to the alkyl, —$CH_2CH_2OCH_2CH_2$OH, $C_{1-10}$ with an attached 4-pyridyl group, $C_{1-10}$ with an attached 3-pyridyl group, $C_{1-10}$ with an attached 2-pyridyl group, $C_{1-10}$ with an attached cyclohexyl group, —NH—$CH_2CH_2$-(4-hydroxyphenyl), —NH—$CH_2CH_2$-(3-indolyl);

b) —$CH_2CH(OH)$—$R^5$, and c) —$(CH_2)_n$—$R^7$;

$R^5$ is selected from the group consisting of phenyl, phenyl monosubstituted with J, phenyl disubstituted with J, phenyl trisubstituted with J, pentafluorophenyl,

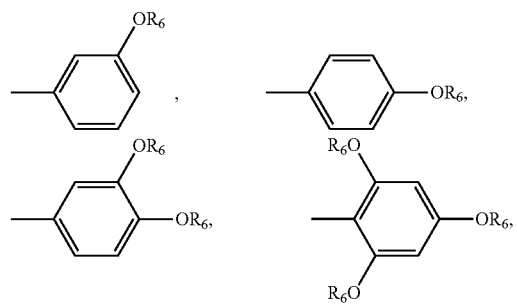

1-naphthyl, 1-naphthyl monosubstituted with J, 1-naphthyl disubstituted with J, 2-naphthyl, 2-naphthyl monosubstituted with J, 2-naphthyl disubstituted with J, 2-pyridyl, 2-quinolinyl, and 1-isoquinolinyl;

R⁶ is selected from the group consisting of $C_{1-4}$ alkyl, $C_{1-4}$ alkyl substituted with phenyl, phenyl, and phenyl substituted with J;

n=1-6;

R⁷ is selected from the group consisting of 2-furyl, 2-furyl monosubstituted with J, 2-pyridyl, 2-pyridyl monosubstituted with J, 3-pyridyl, 3-pyridyl monosubstituted with J, 4-pyridyl, 4-pyridyl monosubstituted with J, 2-quinolinyl, 2-quinolinyl monosubstituted with J, 1-isoquinolinyl, 1-isoquinolinyl monosubstituted with J,

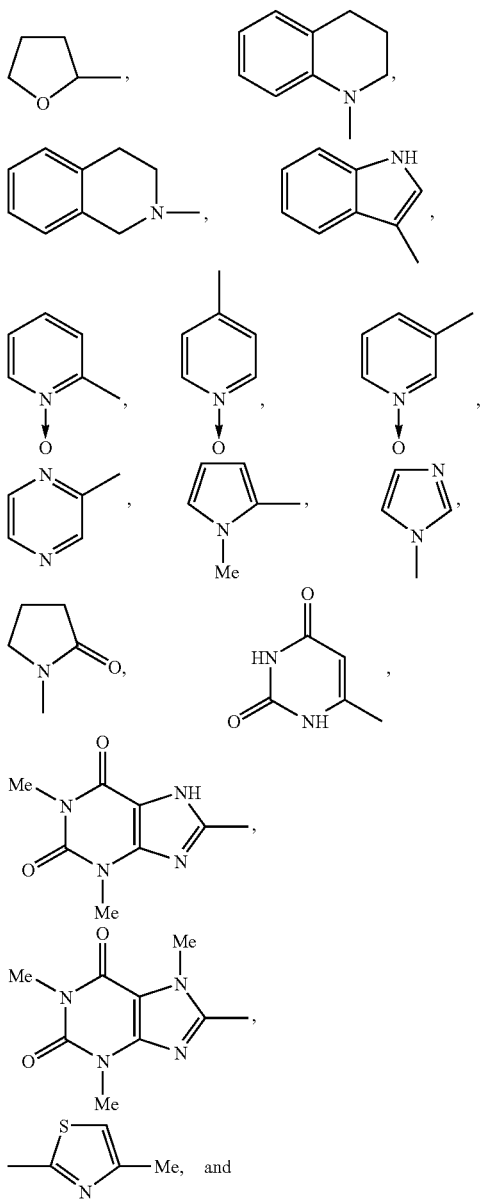

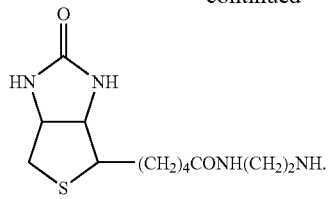

27. A method of alleviation or stabilization of nerve degeneration in a mammal comprising:
    administering to a mammal therapeutically effective amounts of a combination of a calpain inhibitor and a caspase inhibitor;
    wherein the caspase iinhibitor comprises either Cbz-Asp-Glu-Val-AAsp-EP-COOEt or Cbz-Asp-Glu-Val-AAsp-EP-COOCH₂C₆H₅, or both and wherein the inhibitor comprises Z-Leu-Abu- CONH-(CH₂)₃-4-morpholinyl (AK295).

28. A method of alleviation or stabilization of nerve degeneration in a mammal, comprising: administering to a mammal therapeutically effective amounts of a combination of a calpain inhibitor and a caspase inhibitor wherein the caspase inhibitor comprises Cbz-Asp-Glu-Val-AAsp-EP-COOEt and wherein the calpain inhibitor comprises Z-Leu-Abu-CONH-(CH₂)₃-4-morpholinyl (AK295).

29. The method of claim 12, further comprising administering a therapeutically effective amount of a calpain inhibitor to the patient.

30. The method of claim 13, further comprising administering a therapeutically effective amount of a calpain inhibitor to the patient.

31. The method of claim 14, further comprising administering a therapeutically effective amount of a calpain inhibitor to the patient.

32. The method of claim 15, further comprising administering a therapeutically effective amount of a calpain inhibitor to the patient.

33. The method of claim 16, further comprising administering a therapeutically effective amount of a calpain inhibitor to the patient.

34. The method of claim 17, further comprising administering a therapeutically effective amount of a calpain inhibitor to the patient.

35. The method of claim 18, further comprising administering a therapeutically effective amount of a calpain inhibitor to the patient.

36. The method of claim 19, further comprising administering a therapeutically effective amount of a calpain inhibitor to the patient.

37. The method of claim 20, further comprising administering a therapeutically effective amount of a calpain inhibitor to the patient.

38. The method of claim 21, wherein a calpain inhibitor is administered prior to or simultaneously with the anticancer drug.

* * * * *

UNITED STATES PATENT AND TRADEMARK OFFICE
CERTIFICATE OF CORRECTION

Page 1 of 1

PATENT NO. : 8,013,014 B2
APPLICATION NO. : 11/338147
DATED : September 6, 2011
INVENTOR(S) : James C. Powers and Jonathan D. Glass It is certified that error appears in the above-identified patent and that said Letters Patent is hereby corrected as shown below:

Title Page, Item (73) Assignee should read:

--(73) Assignees: Georgia Tech Research Corporation, Atlanta, GA (US);
Emory University, Atlanta, GA (US)--

Signed and Sealed this
Fifth Day of June, 2012

David J. Kappos
*Director of the United States Patent and Trademark Office*